(12) United States Patent
Snoeck et al.

(10) Patent No.: US 11,739,299 B2
(45) Date of Patent: Aug. 29, 2023

(54) LUNG AND AIRWAY PROGENITORS GENERATED FROM HUMAN PLURIPOTENT STEM CELLS AND RELATED TREATMENTS

(71) Applicant: The Trustees of Columbia University in the City of New York, New York, NY (US)

(72) Inventors: Hans-Willem Snoeck, New York, NY (US); Ya-Wen Chen, New York, NY (US)

(73) Assignee: The Trustees of Columbia University in the City of New York, New York, NY (US)

(*) Notice: Subject to any disclaimer, the term of this patent is extended or adjusted under 35 U.S.C. 154(b) by 198 days.

(21) Appl. No.: 17/088,090

(22) Filed: Nov. 3, 2020

(65) Prior Publication Data

US 2021/0115408 A1 Apr. 22, 2021

Related U.S. Application Data

(63) Continuation of application No. PCT/US2019/031130, filed on May 7, 2019.

(60) Provisional application No. 62/667,859, filed on May 7, 2018.

(51) Int. Cl.
*C12N 5/071* (2010.01)

(52) U.S. Cl.
CPC ........ *C12N 5/0689* (2013.01); *C12N 2501/11* (2013.01); *C12N 2501/117* (2013.01); *C12N 2501/119* (2013.01); *C12N 2501/155* (2013.01); *C12N 2501/33* (2013.01); *C12N 2501/727* (2013.01); *C12N 2501/999* (2013.01); *C12N 2506/02* (2013.01); *C12N 2506/45* (2013.01)

(58) Field of Classification Search
None
See application file for complete search history.

(56) References Cited

U.S. PATENT DOCUMENTS

| | | | |
|---|---|---|---|
| 9,234,170 B2 | 1/2016 | Snoeck et al. | |
| 9,719,067 B2* | 8/2017 | Snoeck | C12N 5/0688 |
| 9,988,606 B2 | 6/2018 | Snoeck et al. | |
| 2014/0329318 A1 | 11/2014 | Rajagopal et al. | |
| 2017/0022507 A1 | 1/2017 | Reyon et al. | |
| 2018/0112186 A1 | 4/2018 | Gotoh et al. | |

FOREIGN PATENT DOCUMENTS

| | | | |
|---|---|---|---|
| WO | WO 18/176044 * | 9/2018 | C12N 5/071 |

OTHER PUBLICATIONS

Butler et al, American Journal of Respiratory and Critical Care Medicine, Jul. 15, 2016, vol. 194, No. 2 pp. 156-168. (Year: 2016).*
Dye et al, eLIFE, 2015, 4:e05098, 25 pages (Year: 2015).*
Franks et al, NHLBI Workshop Summaries, Proc Am Thorac Soc, 2008, vol. 5, pp. 763-766. (Year: 2008).*
Huang et al, Nature Biotechnology, 2014, vol. 32, No. 1. pp 84-91 and Supplement (Year: 2014).*
Miller et al, Stem Cell Reports, Jan. 2018, vol. 10, pp. 101-119. (Year: 2018).*
Murry et al., Differentiation of embryonic stem cells to clinically relevant populations: lessons from embryonic development. Cell, 2008, 132, 661-680.
Hanna et al., Pluripotency and cellular reprogramming: facts, hypotheses, unresolved issues. Cell, 2010, 143, 508-525.
Takahashi et al., Induction of pluripotent stem cells from mouse embryonic and adult fibroblast cultures by defined factors. Cell (2006) 126, 663-676.
Yamanaka, S. A fresh look at iPS cells. Cell, 2009, 137, 13-17.
Okita et al., Induced pluripotent stem cells: opportunities and challenges. Philos Trans R Soc Lond B Biol Sci (2011) 366, 2198-2207.
Park et al. Reprogramming of human somatic cells to pluripotency with defined factors. Nature (2008) 451, 141-146.
Yu et al. Induced pluripotent stem cell lines derived from human somatic cells. Science (2007) 318, 1917-1920.
Chen et al. A three-dimensional model of human lung development and disease from pluripotent stem cells. Nature Cell Biology (2017) 19, 542-549.
Orens et al., General overview of lung transplantation and review of organ allocation. Proc Am Thorac Soc (2009) 6, 13-19.
Morrisey et al., Preparing for the first breath: genetic and cellular mechanisms in lung development. Dev Cell (2010) 18, 8-23.
Nikolic et al., Human embryonic lung epithelial tips are multipotent progenitors that can be expanded in vitro as long-term self-renewing organoids. eLife 6, doi:10.7554/eLife.26575 (2017).
Llames et al. Feeder Layer Cell Actions and Applications. Tissue Engineering: Part B (Aug. 1, 2015) vol. 21, No. 4, pp. 345-353, p. 348, col. 1, para 3—col. 2, para 1-3.
International Search Report and Written Opinion of PCT/US19/31130, dated Jul. 25, 2019.
Gjorevski et al, Designer matrices for intestinal stem cell and organoid culture, Nature, 2016, 539(7630):560-564.
DiMarco et al., Protein-engineered scaffolds for in vitro 3D culture of primary adult intestinal organoids, Biomater Sci. 2015, 3(10):1376-85.
Hagen et al., Expression and Characterization of GSK-3 Mutants and Their Effect on beta-Catenin Phosphorylation in Intact Cells, (2002), J. Biol. Chem., 277(26):23330-23335.
Evans et al. Establishment in culture of pluripotential cells from mouse embryos, (1981) Nature 292:154-156.
Matsui et al. Effect of Steel factor and leukemia inhibitory factor on murine primordial germ cells in culture, (1991) Nature 353:750-2.
Thomson et al., Isolation of a primate embryonic stem cell line, (1995) Proc. Natl. Acad. Sci. USA. 92:7844-8.
Thomson et al., Embryonic Stem Cell Lines Derived from Human Blastocysts, (1998) Science 282:1145-1147.

(Continued)

*Primary Examiner* — Allison M Fox
(74) *Attorney, Agent, or Firm* — Leason Ellis LLP

(57) ABSTRACT

The present disclosure provides methods for generating lung progenitor cells, and populations of cells made using the methods. The lung progenitors and related compositions can be used as therapeutic treatments for various pulmonary disorders or related injuries.

18 Claims, 12 Drawing Sheets

(56) References Cited

OTHER PUBLICATIONS

Shamblott et al., Derivation of pluripotent stem cells from cultured human primordial germ cells, (1998) Proc. Natl. Acad. Sci. USA 95:13726-31.
Dimos JT et al. (2008) Induced pluripotent stem cells generated from patients with ALS can be differentiated into motor neurons. Science 321: 1218-1221.
Luo et al., Generation of induced pluripotent stem cells from skin fibroblasts of a patient with olivopontocerebellar atrophy, Tohoku J. Exp. Med. 2012, 226(2): 151-9.
Robinton et al., The promise of induced pluripotent stem cells in research and therapy. Nature 481, 295-305 (2012).
Petersen, T. H. et al. Tissue-engineered lungs for in vivo implantation. Science 329, 538-541 (2010).
Noble et al., Pulmonary fibrosis: patterns and perpetrators. J Clin Invest 122, 2756-2762 (2012).
Ryu, J. H. et al. Idiopathic pulmonary fibrosis: evolving concepts. Mayo Clinic proceedings 89, 1130-1142 (2014).
Pierson et al. Pulmonary fibrosis in hermansky-pudlak syndrome, a case report and review. Respiration; international review of thoracic diseases 73, 382-395 (2006).
Richeldi, L. et al. Efficacy and safety of nintedanib in idiopathic pulmonary fibrosis. The New England journal of medicine 370, 2071-2082 (2014).
McCurry, K. R. et al. Lung transplantation in the United States, 1998-2007. Am J Transplant 9, 942-958 (2009).
Steele et al., Molecular mechanisms in progressive idiopathic pulmonary fibrosis. Annual review of medicine 64, 265-276 (2013).
Mulugeta et al., Lost after translation: insights from pulmonary surfactant for understanding the role of alveolar epithelial dysfunction and cellular quality control in fibrotic lung disease. American journal of physiology. Lung cellular and molecular physiology 309, L507-525 (2015).
Zhang et al., A variant in the promoter of MUC5B and idiopathic pulmonary fibrosis. The New England journal of medicine 364, 1576-1577 (2011).
Fingerlin, T. E. et al. Genome-wide association study identifies multiple susceptibility loci for pulmonary fibrosis. Nat Genet 45, 613-620 (2013).
Seibold, M. A. et al. A common MUC5B promoter polymorphism and pulmonary fibrosis. The New England journal of medicine 364, 1503-1512 (2011).
Yang et al., MUC5B and Idiopathic Pulmonary Fibrosis. Ann Am Thorac Soc 12 Suppl 2, S193-199 (2015).
Loyd, J. E. Pulmonary fibrosis in families. American journal of respiratory cell and molecular biology 29, S47-50 (2003).
Whitsett et al., Diseases of pulmonary surfactant homeostasis. Annual review of pathology 10, 371-393 (2015).
Wang, Y. et al. Genetic defects in surfactant protein A2 are associated with pulmonary fibrosis and lung cancer. American journal of human genetics 84, 52-59 (2009).
Lawson, W. E. et al. Genetic mutations in surfactant protein C are a rare cause of sporadic cases of IPF. Thorax 59, 977-980 (2004).
Thomas, A. Q. et al. Heterozygosity for a surfactant protein C gene mutation associated with usual interstitial pneumonitis and cellular nonspecific interstitial pneumonitis in one kindred. Am J Respir Crit Care Med 165, 1322-1328 (2002).
Lawson, W. E. et al. Endoplasmic reticulum stress enhances fibrotic remodeling in the lungs. Proc Natl Acad Sci U S A 108, 10562-10567 (2011).
Korfei, M. et al. Epithelial endoplasmic reticulum stress and apoptosis in sporadic idiopathic pulmonary fibrosis. Am J Respir Crit Care Med 178, 838-846 (2008).
Tanjore et al., Emerging evidence for endoplasmic reticulum stress in the pathogenesis of idiopathic pulmonary fibrosis. American journal of physiology. Lung cellular and molecular physiology 302, L721-729 (2012).
Hawkins, A. et al. A non-BRICHOS SFTPC mutant (SP-CI73T) linked to interstitial lung disease promotes a late block in macroautophagy disrupting cellular proteostasis and mitophagy. American journal of physiology. Lung cellular and molecular physiology 308, L33-47 (2015).
Araya, J. et al. Insufficient autophagy in idiopathic pulmonary fibrosis. American journal of physiology. Lung cellular and molecular physiology 304, L56-69 (2013).
Margaritopoulos, G. A. et al. Self-eating: friend or foe? The emerging role of autophagy in idiopathic pulmonary fibrosis. BioMed research international 2013, 420497 (2013).
Patel, A. S. et al. Autophagy in idiopathic pulmonary fibrosis. PLoS One 7, e41394 (2012).
Bueno, M. et al. PINK1 deficiency impairs mitochondrial homeostasis and promotes lung fibrosis. J Clin Invest, 2015;125(2):521-538.
Armanios, M. Y. et al. Telomerase mutations in families with idiopathic pulmonary fibrosis. The New England journal of medicine 356, 1317-1326 (2007).
Alder, J. K. et al. Short telomeres are a risk factor for idiopathic pulmonary fibrosis. Proc Natl Acad Sci U S A 105, 13051-13056 (2008).
Alder, J. K. et al. Ancestral mutation in telomerase causes defects in repeat addition processivity and manifests as familial pulmonary fibrosis. PLoS genetics 7, e1001352 (2011).
Alder, J. K. et al. Exome sequencing identifies mutant TINF2 in a family with pulmonary fibrosis. Chest, 2015; 147(5): 1361-1368.
Armanios, M. Telomerase mutations and the pulmonary fibrosis-bone marrow failure syndrome complex. The New England journal of medicine 367(4): 384 (2012).
Armanios, M. Telomerase and idiopathic pulmonary fibrosis. Mutation research 730, 52-58 (2012).
Stuart, B. D. et al. Exome sequencing links mutations in PARN and RTEL1 with familial pulmonary fibrosis and telomere shortening. Nat Genet 47, 512-517 (2015).
Desai, T. J., Brownfield, D. G. & Krasnow, M. A. Alveolar progenitor and stem cells in lung development, renewal and cancer. Nature 507, 190-194 (2014).
Rock, J. R. et al. Multiple stromal populations contribute to pulmonary fibrosis without evidence for epithelial to mesenchymal transition. Proc Natl Acad Sci U S A 108, E1475-1483 (2011).
Barkauskas, C. E. et al. Type 2 alveolar cells are stem cells in adult lung. J Clin Invest, 2013;123(7):3025-3036.
Alder, J. K. et al. Telomere dysfunction causes alveolar stem cell failure. Proc Natl Acad Sci U S A 112, 5099-5104 (2015).
Young, L. R. et al. The alveolar epithelium determines susceptibility to lung fibrosis in Hermansky-Pudlak syndrome. Am J Respir Crit Care Med 186, 1014-1024 (2012).
Mahavadi, P., Guenther, A. & Gochuico, B. R. Hermansky-Pudlak syndrome interstitial pneumonia: it's the epithelium, stupid! Am J Respir Crit Care Med 186, 939-940 (2012).
Crapo, J. D. Morphologic changes in pulmonary oxygen toxicity. Annu Rev Physiol 48, 721-731 (1986).
Mantell et al., Signal transduction pathways in hyperoxia-induced lung cell death. Mol Genet Metab 71, 359-370 (2000).
Tanaka, A. et al. Hyperoxia-induced LC3B interacts with the Fas apoptotic pathway in epithelial cell death. Am J Respir Cell Mol Biol 46, 507-514 (2012).
Kazzaz, J. A. et al. Cellular oxygen toxicity. Oxidant injury without apoptosis. J Biol Chem 271, 15182-15186 (1996).
Barazzone et al. Oxygen toxicity in mouse lung: pathways to cell death. Am J Respir Cell Mol Biol 19, 573-581 (1998).
Petrache, I. et al. Mitogen-activated protein kinase pathway mediates hyperoxia-induced apoptosis in cultured macrophage cells. Am J Physiol 277, L589-595 (1999).
McGrath-Morrow, S. A. & Stahl, J. Apoptosis in neonatal murine lung exposed to hyperoxia. Am J Respir Cell Mol Biol 25, 150-155 (2001).
O'Reilly, M. A. et al. The cyclin-dependent kinase inhibitor p21 protects the lung from oxidative stress. Am J Respir Cell Mol Biol 24, 703-710 (2001).

(56) References Cited

OTHER PUBLICATIONS

De Paepe, M. E. et al. Hyperoxia-induced apoptosis and Fas/FasL expression in lung epithelial cells. Am J Physiol Lung Cell Mol Physiol 289, L647-659 (2005).
Pagano, A. et al. Poly(ADP-ribose)polymerase activation mediates lung epithelial cell death in vitro but is not essential in hyperoxia-induced lung injury. Am J Respir Cell Mol Biol 33, 555-564 (2005).
Beck, J. M. et al. Pneumocystis pneumonia increases the susceptibility of mice to sublethal hyperoxia. Infect Immun 71, 5970-5978 (2003).
Alphonse, R. S. et al. Existence, functional impairment, and lung repair potential of endothelial colony-forming cells in oxygen-induced arrested alveolar growth. Circulation 129, 2144-2157 (2014).
Rawlins et al. Lung development and repair: contribution of the ciliated lineage. Proc Natl Acad Sci U S A 104, 410-417 (2007).
Borthwick et al. Evidence for stem-cell niches in the tracheal epithelium. Am J Respir Cell Mol Biol 24, 662-670 (2001).
O'Koren et al. Loss of basal cells precedes bronchiolitis obliterans-like pathological changes in a murine model of chlorine gas inhalation. Am J Respir Cell Mol Biol 49, 788-797 (2013).
Guha, A. et al. Neuroepithelial body microenvironment is a niche for a distinct subset of Clara-like precursors in the developing airways. Proc Natl Acad Sci U S A 109, 12592-12597 (2012).
Guha, A. et al. Analysis of Notch signaling-dependent gene expression in developing airways reveals diversity of Clara cells PLoS One 9, e88848 (2014).
Song, H. et al. Functional characterization of pulmonary neuroendocrine cells in lung development, injury, and tumorigenesis. Proc Natl Acad Sci U S A 109, 17531-17536 (2012).
Rock, J. R. et al. Notch-dependent differentiation of adult airway basal stem cells. Cell Stem Cell 8, 639-648 (2011).
Rosen et al. Preconditioning allows engraftment of mouse and human embryonic lung cells, enabling lung repair in mice. Nat Med 21, 869-879 (2015).
Verhoeven et al. Pulse-oximetry accurately predicts lung pathology and the immune response during influenza infection. Virology 390, 151-156 (2009).
Bot, A. et al. Cellular mechanisms involved in protection and recovery from influenza virus infection in immunodeficient mice. J Virol 70, 5668-5672 (1996).
Huang, S. X. et al. The in vitro generation of lung and airway progenitor cells from human pluripotent stem cells. Nature protocols 10, 413-425 (2015).
Green, M. D. et al. Generation of anterior foregut endoderm from human embryonic and induced pluripotent stem cells. Nature biotechnology 29, 267-272 (2011).
Firth, A. L. et al. Generation of multiciliated cells in functional airway epithelia from human induced pluripotent stem cells. Proc Natl Acad Sci U S A 111, E1723-1730 (2014).
Gotoh, S. et al. Generation of alveolar epithelial spheroids via isolated progenitor cells from human pluripotent stem cells. Stem cell reports 3, 394-403 (2014).
Konishi, S. et al. Directed Induction of Functional Multi-ciliated Cells in Proximal Airway Epithelial Spheroids from Human Pluripotent Stem Cells. Stem cell reports 6, 18-25 (2016).
Wong, A. P. et al. Directed differentiation of human pluripotent stem cells into mature airway epithelia expressing functional CFTRTR protein. Nature biotechnology 30, 876-882 (2012).
Mou, H. et al. Generation of Multipotent Lung and Airway Progenitors from Mouse ESCs and Patient-Specific Cystic Fibrosis iPSCs. Cell Stem Cell 10, 385-397 (2012).
Matute-Bello, G., Frevert, C. W. & Martin, T. R. Animal models of acute lung injury. American journal of physiology. Lung cellular and molecular physiology 295, L379-399 (2008).
Dorrello, N. V. et al. Functional vascularized lung grafts for lung bioengineering. Sci Adv 3, e1700521, doi:10.1126/sciadv.1700521 (2017).
Tata, A. et al. Myoepithelial Cells of Submucosal Glands Can Function as Reserve Stem Cells to Regenerate Airways after Injury. Cell Stem Cell 22, 668-683 e666, (2018).
Xie, Y. et al. Mucociliary Transport in Healthy and Cystic Fibrosis Pig Airways. Ann Am Thorac Soc 15, S171-S176 (2018).
McCarron, A., Donnelley, M. & Parsons, D. Airway disease phenotypes in animal models of cystic fibrosis. Respiratory research 19, 54 (2018).
Anjali Jacob, et al.: "Differentiation of Human Pluripotent Stem Cells into Functional Lung Alveolar Epithelial Cells", Cell Stem Cell 21, 1-17, 2017.
Lancaster et al., Organogenesis in a dish: modeling development and disease using organoid technologies. Science 345, 1247125 (2014).
Fatehullah, A., Tan, S. H. & Barker, N. Organoids as an in vitro model of human development and disease. Nat Cell Biol 18, 246-254 (2016).
Clevers, H. Modeling Development and Disease with Organoids. Cell 165, 1586-1597 (2016).
King, T. E., Jr. et al. A phase 3 trial of pirfenidone in patients with idiopathic pulmonary fibrosis. The New England journal of medicine 370, 2083-2092 (2014).
Dye, B. R. et al. A bioengineered niche promotes in vivo engraftment and maturation of pluripotent stem cell derived human lung organoids. Elite 5, doi:10.7554/eLife.19732 (2016).
Seward et al., Hermansky-Pudlak syndrome: health care throughout life. Pediatrics 132, 153-160 (2013).
Whitsett et al. Alveolar surfactant homeostasis and the pathogenesis of pulmonary disease. Annual review of medicine 61, 105-119 (2010).
Ott, H. C. et al. Regeneration and orthotopic transplantation of a bioartificial lung. Nat Med 16, 927-933 (2010).
Takahashi, K. et al. Induction of pluripotent stem cells from adult human fibroblasts by defined factors. Cell 131, 861-872 (2007).
Rock, J. R. & Hogan, B. L. Epithelial progenitor cells in lung development, maintenance, repair, and disease. Annu Rev Cell Dev Biol 27, 493-512 (2011).
Macchiarini, P. et al. Clinical transplantation of a tissue-engineered airway. Lancet 372, 2023-2030 (2008).
Laurance, J. "British boy receives trachea transplant built with his own stem cells." BMJ 340, c1633 (2010).
Sheridan et al. Effect of peripheral-blood progenitor cells mobilised by filgrastim (G-CSF) on platelet recovery after high-dose chemotherapy. Lancet 339, 640-644 (1992).
Delaere et al. Tracheal allotransplantation after withdrawal of immunosuppressive therapy. The New England journal of medicine 362, 138-145 (2010).
Delaere et al. Learning curve in tracheal allotransplantation. Am J Transplant 12, 2538-2545 (2012).
Delaere, P. R. Tracheal transplantation. Current opinion in pulmonary medicine 18, 313-320 (2012).
Rawlins et al., Ciliated epithelial cell lifespan in the mouse trachea and lung. American journal of physiology. Lung cellular and molecular physiology 295, L231-234 (2008).
Giangreco et al. Terminal bronchioles harbor a unique airway stem cell population that localizes to the bronchoalveolar duct junction. The American journal of pathology 161, 173-182 (2002).
Hong et al. Clara cell secretory protein-expressing cells of the airway neuroepithelial body microenvironment include a label-retaining subset and are critical for epithelial renewal after progenitor cell depletion. American journal of respiratory cell and molecular biology 24, 671-681 (2001).
Rawlins, E. L. et al. The role of Scgb1a1+ Clara cells in the long-term maintenance and repair of lung airway, but not alveolar, epithelium. Cell Stem Cell 4, 525-534 (2009).
Rock, J. R. et al. Basal cells as stem cells of the mouse trachea and human airway epithelium. Proc Natl Acad Sci U S A 106, 12771-12775 (2009).
Hegab, A. E. et al. Novel stem/progenitor cell population from murine tracheal submucosal gland ducts with multipotent regenerative potential. Stem Cells 29, 1283-1293 (2011).
Lynch, T. J. et al. Submucosal Gland Myoepithelial Cells Are Reserve Stem Cells That Can Regenerate Mouse Tracheal Epithelium. Cell Stem Cell, doi:10.1016/j.stem.2018.03.017 (2018).
Tata, P. R. et al. Dedifferentiation of committed epithelial cells into stem cells in vivo. Nature 503, 218-223 (2013).

(56) References Cited

OTHER PUBLICATIONS

Beers, M. F. & Morrisey, E. E. The three R's of lung health and disease: repair, remodeling, and regeneration. J Clin Invest 121, 2065-2073 (2011).

Barkauskas, C. E. et al. Type 2 alveolar cells are stem cells in adult lung. J Clin Invest 123, 3025-3036 (2013).

Jain, R. et al. Plasticity of Hopx(+) type I alveolar cells to regenerate type II cells in the lung. Nature communications 6, 6727 (2015).

Kumar, P. A. et al. Distal airway stem cells yield alveoli in vitro and during lung regeneration following H1N1 influenza infection. Cell 147, 525-538 (2011).

Vaughan et al. Lineage-negative progenitors mobilize to regenerate lung epithelium after major injury. Nature 517, 621-625 (2015).

Zuo, W. et al. p63(+)Krt5(+) distal airway stem cells are essential for lung regeneration. Nature 517, 616-620 (2015).

Yang, Y. et al. Spatial-Temporal Lineage Restrictions of Embryonic p63(+) Progenitors Establish Distinct Stem Cell Pools in Adult Airways. Dev Cell 44, 752-761, e754 (2018).

Plopper et al. The non-human primate as a model for studying COPD and asthma. Pulmonary pharmacology & therapeutics 21, 755-766 (2008).

Smith et al., Normal development of the lung and premature birth. Paediatric respiratory reviews 11, 135-142 (2010).

Krasteva et al., "Tasting" the airway lining fluid. Histochemistry and cell biology (2012).

Rawlins, E. L. & Hogan, B. L. Intercellular growth factor signaling and the development of mouse tracheal submucosal glands. Dev Dyn 233, 1378-1385 (2005).

Herriges, M. & Morrisey, E. E. Lung development: orchestrating the generation and regeneration of a complex organ. Development 141, 502-513 (2014).

Warburton, D. et al. Lung organogenesis. Current topics in developmental biology 90, 73-158 (2010).

Herring et al. Growth of alveoli during postnatal development in humans based on stereological estimation. American journal of physiology. Lung cellular and molecular physiology 307, L338-344 (2014).

McMullan, R. et al. Keratinocyte differentiation is regulated by the Rho and ROCK signaling pathway. Current biology : CB 13, 2185-2189 (2003).

Chapman et al. Human keratinocytes are efficiently immortalized by a Rho kinase inhibitor. J Clin Invest 120, 2619-2626 (2010).

Liu, X. et al. ROCK inhibitor and feeder cells induce the conditional reprogramming of epithelial cells. The American journal of pathology 180, 599-607 (2012).

Wang, X. et al. Cloning and variation of ground state intestinal stem cells. Nature 522, 173-178 (2015).

Mou, H. et al. Dual SMAD Signaling Inhibition Enables Long-Term Expansion of Diverse Epithelial Basal Cells. Cell Stem Cell 19, 217-231 (2016).

Que et al. Morphogenesis of the trachea and esophagus: current players and new roles for noggin and Bmps, Differentiation, 74, 422-437 (2006).

Que, J. et al. Multiple dose-dependent roles for Sox2 in the patterning and differentiation of anterior foregut endoderm. Development 134, 2521-2531 (2007).

Liu et al., Differential gene expression in the distal tip endoderm of the embryonic mouse lung. Gene Expression Patterns, 2, 229-233 (2002).

Rawlins et al. The Id2+ distal tip lung epithelium contains individual multipotent embryonic progenitor cells. Development 136, 3741-3745 (2009).

Treutlein, B. et al. Reconstructing lineage hierarchies of the distal lung epithelium using single-cell RNA-seq. Nature 509, 371-375 (2014).

Frank, D. B. et al. Emergence of a Wave of Wnt Signaling that Regulates Lung Alveologenesis by Controlling Epithelial Self-Renewal and Differentiation. Cell reports 17, 2312-2325 (2016).

Swarr, D. T. & Morrisey, E. E. Lung endoderm morphogenesis: gasping for form and function. Annu Rev Cell Dev Biol 31, 553-573 (2015).

Miller, A. J. et al. In Vitro Induction and In Vivo Engraftment of Lung Bud Tip Progenitor Cells Derived from Human Pluripotent Stem Cells. Stem Cell Reports 10, 101-119 (2018).

Nichane et al. Isolation and 3D expansion of multipotent Sox9(+) mouse lung progenitors. Nature methods 14, 1205-1212 (2017).

McCauley, K. B. et al. Efficient Derivation of Functional Human Airway Epithelium from Pluripotent Stem Cells via Temporal Regulation of Wnt Signaling. Cell Stem Cell 20, 844-857 (2017).

Crapo et al., Structural and biochemical changes in rat lungs occurring during exposures to lethal and adaptive doses of oxygen. The American review of respiratory disease 122, 123-143 (1980).

Ciancanelli, M.J. et al. Life-threatening influenza and impaired interferon amplification in human IRF7 deficiency. Science (2015).

\* cited by examiner

LUNG AND AIRWAY PROGENITORS GENERATED FROM HUMAN PLURIPOTENT STEM CELLS AND RELATED TREATMENTS

CROSS REFERENCE TO RELATED APPLICATION

This application claims priority to U.S. Provisional Application No. 62/667,859 filed on May 7, 2018, which is incorporated by reference herein in its entirety.

STATEMENT OF GOVERNMENTAL INTEREST

This invention was made with government support under HL120046 and HL134760 awarded by the National Institutes of Health. The government has certain rights in the invention.

FIELD OF THE INVENTION

Embodiments of the present invention are directed to various methods for generating lung progenitor cells, stable culture systems of these cells, and to populations of cells made using these methods. In certain embodiments, the lung progenitors can be used as therapeutic treatments for various pulmonary disorders or related injuries.

BACKGROUND OF THE INVENTION

Cellular therapies for lung disease aim at replacing the cells that replenish the airway or lung epithelium after injury and during physiological wear and tear. The basal homeostatic turnover in the lung is very low[57], but the launching of ample regenerative capacity after injury hints at the existence of a physiologically capable stem cell population[48,58,59]. The strongest evidence for regenerative activity, and the most rigorous insight into the potential of some stem and progenitor cell populations in the lung in vivo comes from lineage tracing experiments. These have shown that in postnatal mouse bronchioli, club cells could give rise to ciliated cells[60]. In the trachea, however, Scgb1a1 (CC-10 or CCSP)-expressing club-like cells can give rise to ciliated cells, but do not possess extensive self-renewal capacity, and are replenished from a Scgb1a1-negative precursor. Nevertheless, after $SO_2$ injury, surviving tracheal club cells do contribute to repair[60]. In the trachea, most regenerative capacity is derived from the cytokeratin $(Krt)5^+p63^+$ basal cells, which make up 30% of the epithelium and express Ngfr and CD49f (integrin α6)[61]. Submucosal gland ducts also contain regenerative activity from ductal cells[62]. More recent studies, however, have shown that myoepithelial cells in submucosal glands can replace BCs, and ultimately all surface epithelium after severe airway injury[63]. Furthermore, it has been shown that extensive plasticity may exist in the airway, as club cells can replenish the BC compartment after selective depletion of the latter[64]. Taken together, the airway has multiple layers of regenerative potential.

A similar principle applies to the distal lung, where a subset of type 2 alveolar epithelial cells (ATII cells) can function as stem cells, although regeneration by ATI cells has also been demonstrated[65-67]. After severe injury, a population of KRT5+ cells (distal stem cells, DSCs), resembling BCs, migrates distally and participates in fibrotic emergency repair[68-70]. For the origin of these cells, it has been suggested that they are derived from the LNEPs (lineage-negative epithelial precursors) that are $Sox2^+$ $Itgfb4^+Krt5^-p63^-$ in the distal lung or from $p63^+Krt5^+$ distal airway cells. More recent findings indicate that they originate from pool of p63+Krt5− cells in the intrapulmonary airways[71].

Lung and airway originate from buds on the ventral anterior foregut endoderm (AFE) and are specified by the surrounding mesoderm. The lung buds develop through a stereotyped branching process into stalks with proliferating progenitors at the tips (pseudoglandular stage)[3]. During the canalicular stage, cell cycle activity decreases in the stalks, and specialization of the airway epithelium occurs with the emergence of basal, goblet, club, ciliated, and other cell types[87-88]. In the saccular stage the canaliculi widen distally into primitive alveoli[3,76,77]. Alveoli contain alveolar epithelial type I (ATI), which are essential for gas exchange, and type II (ATII) cells, which produce surfactant, critical for the maintenance of alveolar integrity by reducing surface tension[3,43,76]. During the saccular stage, cells expressing markers of both ATI and ATII cells are found at the tips. These may resolve into ATI or ATII cells and have been called bipotential progenitors[35,67,89]. Alveolar expansion and secondary septation continue postnatally[78,90].

Two pools of multipotent cells have been identified in the developing mouse lung. Early during lung specification, a population of $p63^+Krt^-$ cells is present that can give rise to both distal and proximal epithelium later in life. Around E10.5, these cells become restricted to proximal fates in trachea and extrapulmonary airways, and at E13.5 begin to occupy the basal layers of the maturing pseudostratified epithelium and subsequently express Krt5, marker of mature BCs'. At the same time, distal tip progenitors (DTPs) arise at the tips of the branching tubules that are precursors of intrapulmonary airway and alveolar epithelial cells during development[88,91,92].

Diseases that are amenable to cellular therapies encompass both airway and distal lung disease. Cystic fibrosis (CF) affects multiple organs; however, thanks to advances in treatment and prevention of complications, its pulmonary manifestations are the main cause of morbidity and mortality. As CF predominantly affects airways, cellular therapy using stem cell-derived, patient-specific and/or genetically corrected cells can provide an effective treatment and even a definitive cure. Cellular therapies are particularly useful for patients for whom current and future corrector and therapies are ineffective because they lack expression of cystic fibrosis transmembrane conductance regulator (CFTR). In addition, patients for whom pharmacological therapies are less effective might become candidates as well.

Among distal lung diseases, many affect the function of type II alveolar epithelial cells. Replacing those with stem cell-derived, patient-specific and genetically corrected cells may provide a cure. One such distal lung disease is idiopathic pulmonary fibrosis (IPF). The notion that defects in ATII cells underlie IPF is further supported by the fact that patients with Hermansky-Pudlak Syndrome (HPS) show a high incidence of IPF, also called HPS-associated interstitial pneumonia (HPSIP).[10] HPSIP is histologically, clinically, and prognostically very similar to IPF, and also does not respond to immune suppressive therapy.[39-42] A key feature of HPS are abnormal ("giant") lamellar bodies in ATII cells, where surfactant is stored, secreted and recycled. HPS is caused by abnormal biogenesis and trafficking of lysosome-related organelles (LROs) and characterized by pigmentation abnormalities and bleeding diathesis associated with dysfunction of melanosomes and platelet delta granules, which are, similar to LBs, LROs. Several congenital interstitial lung diseases in children are also caused by mutation in genes essential for ATII cells. Examples include ABCA3, SFTPB and SFTPC mutations[16,43]. Provided that diseased ATII cells could be removed from the lung, cellular replacement therapy by engrafting with progenitor cells or ATII cells derived from these may provide improvement or even cure. The lung progenitor cells described herein can be used to treat such conditions.

Because of their relatively simple structure, some clinical successes have been achieved with engineered trachea and large airways[49,56]. Thus, tissue engineering strategies could be further developed for regenerative medicine for lung and airway diseases. The use of the correct cells that are able to differentiate into airway epithelium is important. The lung progenitor cells described herein can be used in such tissue engineering methods.

Regenerative medicine holds promise for new treatment options. Novel approaches for cell replacement therapy for lung disease are urgently needed. New methods and treatments based on the ability to generate lung tissue from human pluripotent stem cells (PSCs) would fundamentally change the outlook of pulmonary and related medicine.

SUMMARY

The present disclosure provides for a method for generating lung progenitor cells. The method may comprise the following steps: (a) producing anterior foregut endoderm cells from mammalian pluripotent stem cells (PSCs); (b) culturing the anterior foregut endoderm cells in a suspension culture to generate at least one lung bud organoid (LBO); (c) embedding the LBO within a 3D matrix; (d) culturing the embedded LBO to form branched LBO (BLBO), and (e) dissociating the LBO or BLBO and culturing the dissociated LBO or BLBO on feeder cells in a culture medium.

The culture medium may comprise an inhibitor of Rho kinase (ROCK). In one embodiment, the inhibitor of ROCK is Y27632.

In the culture medium, the inhibitor of ROCK may be at a concentration ranging from about 0.1 µM to about 100 µM, from about 1 µM to about 50 µM, from about 0.5 µM to about 25 µM, from about 1 µM to about 20 µM, from about 1 µM to about 10 µM, from about 5 µM to about 15 µM, from about 5 µM to about 10 µM, about 5 µM, or about 10 µM.

The culture medium may comprise a glycogen synthase kinase (GSK) inhibitor. In one embodiment, the GSK inhibitor is CHIR99021.

In the culture medium, the GSK inhibitor may be at a concentration ranging from about 0.1 µM to about 100 µM, from about 1 µM to about 50 µM, from about 0.5 µM to about 25 µM, from about 1 µM to about 20 µM, from about 1 µM to about 10 µM, from about 5 µM to about 15 µM, from about 5 µM to about 10 µM, about 5 µM, about 10 µM, or about 3 µM.

The culture medium may comprise one or more of FGF7, FGF10, bone morphogenic protein 4 (BMP4), retinoic acid, and combinations thereof. In one embodiment, one or more of FGF7, FGF10, and BMP4 is/are at a concentration of about 10 ng/ml. In one embodiment, retinoic acid is at a concentration of about 50 nM.

The culture medium may comprise one or more of insulin, EGF, hydrocortisone, cholera toxin, and combinations thereof.

In one embodiment, in step (e), the dissociated BLBO is first cultured in a first culture medium comprising an inhibitor of ROCK (e.g., Y27632), a GSK inhibitor (e.g., CHIR99021), FGF7, FGF10, BMP4 and/or retinoic acid, and then cultured in a second culture medium comprising an inhibitor of ROCK (e.g., Y27632), insulin, EGF, hydrocortisone and/or cholera toxin.

In one embodiment, the 3D matrix may be MATRIGEL® (e.g., a solubilized basement membrane preparation from the Engelbreth-Holm-Swarm (EHS) mouse sarcoma).

The feeder cells may be fibroblasts. In one embodiment, the fibroblasts are irradiated 3T3 cells (e.g., 3T3-J2 cells).

In one embodiment, in step (e), the LBO or BLBO is dissociated at a time point ranging from about day 20 to about day 180, or from about day 25 to about day 150, counting from the beginning of the method.

In one embodiment, in step (e), the LBO or BLBO may be dissociated to single cells or cell clusters.

The mammalian pluripotent stem cells (PSCs) may be human pluripotent stem cells (hPSCs).

The mammalian pluripotent stem cells (PSCs) may be embryonic stem cells (ESCs) and/or induced pluripotent stem cells (iPSCs).

The present disclosure also provides for lung progenitor cells generated by the present methods, or a cell population comprising the present lung progenitor cells generated by the present methods.

In certain embodiments, at least or about 20%, at least or about 30%, at least or about 40%, at least or about 50%, at least or about 60%, at least or about 70%, at least or about 80%, at least or about 90%, of the cell population expresses NKX2.1, SOX2, SOX9, or combinations thereof. In one embodiment, at least or about 70% of the cell population expresses NKX2.1, SOX2, SOX9, or combinations thereof.

In certain embodiments, at least or about 20%, at least or about 30%, at least or about 40%, at least or about 50%, at least or about 60%, at least or about 70%, at least or about 80%, at least or about 90%, of the cell population expresses KRT5, P63, ITGB4, NGFR, or combinations thereof. In one embodiment, at least or about 30% of the cell population expresses KRT5, P63, ITGB4, NGFR, or combinations thereof.

Also encompassed by the present disclosure is a method of treating a pulmonary disorder or injury in a subject in need thereof. The method may comprise administering to the subject a therapeutically effective amount of the present lung progenitor cells.

The pulmonary disorder or injury may include, but is not limited to, cystic fibrosis; emphysema; chronic obstructive pulmonary disease (COPD); pulmonary fibrosis; idiopathic pulmonary fibrosis; Hermansky-Pudlak Syndrome; hypersensitivity pneumonitis; sarcoidosis; asbestosis; autoimmune-mediated interstitial lung disease; pulmonary hypertension; lung cancer; acute lung injury (adult respiratory distress syndrome); respiratory distress syndrome of prematurity, chronic lung disease of prematurity (bronchopulmonary dysplasia); surfactant protein B deficiency, surfactant protein C deficiency, ABCA3 deficiency; ciliopathies; congenital diaphragmatic hernia; pulmonary alveolar proteinosis; pulmonary hypoplasia; lung injury, and combinations thereof.

The pulmonary disorder or injury may be an interstitial lung disease or a congenital surfactant deficiency.

The lung progenitor cells may be non-syngeneic with the subject. The lung progenitor cells may be syngeneic with the subject. The lung progenitor cells may be allogeneic or xenogeneic with the subject.

The present disclosure provides for a biological scaffold comprising the present lung progenitor cells.

In one embodiment, step (b) may comprise culturing the cells in a normoxic incubator.

The present disclosure provides for a method of treating a pulmonary disorder or injury in a subject in need thereof. The method may comprise engrafting a therapeutically effective amount of the present lung progenitor cells into the lung, airway or nasal cavity of the subject.

The engrafted cells may integrate into epithelium.

BRIEF DESCRIPTION OF THE DRAWINGS

FIG. 2A: Morphology of branching Matrigel organoids from which condition A and condition B cells are derived. FIG. 2B: bright field images condition A and condition B cells. FIG. 2C: Immunofluorescence of markers expressed in condition A cells (pDTPs). FIG. 2D: Immunofluorescence of markers expressed in condition B cells (BC-like cells). The lower panel shows analysis of NGFR by flow cytometry. DTP: distal tip progenitor.

FIG. 9a: human cells in distal lung and in SMGs 6 months after administration of condition A/pDTPs. FIG. 9b: Presence of human cells in SMGs 6 months after administration of condition B cells. FIG. 9c: Expression of αSMA and SOX9 in condition B cells. SMG: submucosal gland.

DETAILED DESCRIPTION

Figure 1:
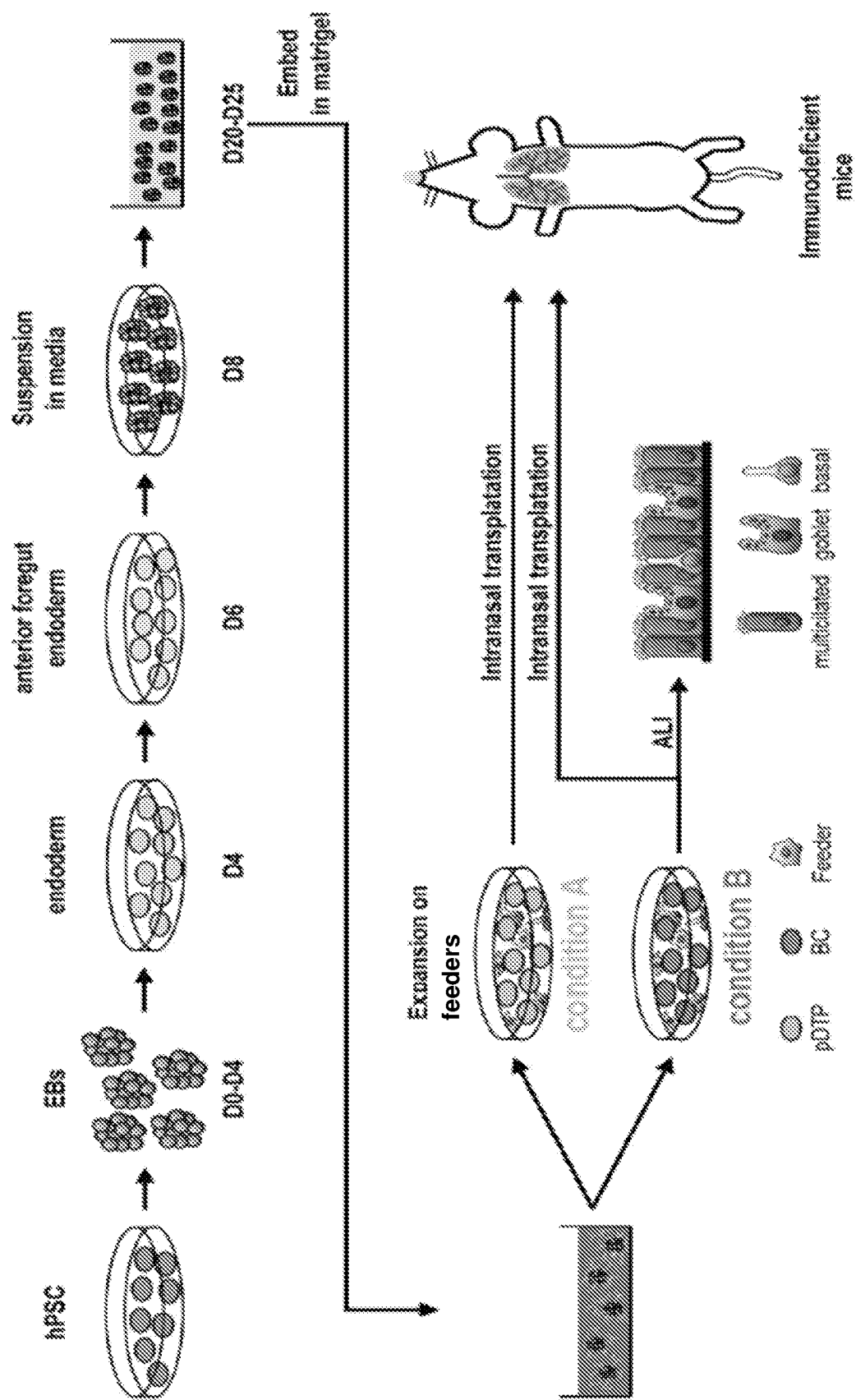
FIG. 1 shows a schematic representation of the experimental protocol for isolating and culturing the novel cell populations described herein. Day 25 lung bud organoids (LBOs) or branching organoids derived from these after plating in Matrigel were dissociated and cultured in condition A or condition B. Expanding cells were analyzed for phenotype and for function using in vivo and in vitro assays.

The present disclosure provides for a method for generating lung progenitor cells. The method may comprise the following steps: (a) producing anterior foregut endoderm cells from mammalian pluripotent stem cells (PSCs); (b) culturing the anterior foregut endoderm cells in a suspension culture to generate at least one lung bud organoid (LBO); (c) embedding the LBO within a 3D matrix; (d) culturing the embedded LBO to form branched LBO (BLBO), and (e) dissociating the LBO or BLBO and culturing the dissociated LBO or BLBO on feeder cells in a culture medium.

The present disclosure provides for cells derived from human pluripotent stem cells (hPSCs), and methods for generating these cells. The ability to generate lung tissue from human pluripotent stem cells (hPSCs) would fundamentally change the outlook of pulmonary medicine. hPSCs may comprise embryonic stem cells (ES) and/or induced pluripotent stem (iPS) cells. Derived from the inner cell mass of the blastocyst, embryonic stem cells (ESCs) can be maintained in a pluripotent state in vitro and have the potential to generate every cell type in the organism. iPSCs are generated by reprogramming somatic cells to a pluripotent state similar to ESCs, and are therefore patient-specific.

Non-limiting examples of pluripotent stem cells (PSCs) include ESCs and iPSCs. Directed differentiation of PSCs into specific lineages involved recapitulating to the extent possible development in vitro.

The present methods and cells may be used to treat a pulmonary disorder or injury. In one embodiment, the pulmonary disorder or injury is an airway lung disease and/or a distal lung disease. In another embodiment, the pulmonary disorder or injury is a non-malignant lung disease. In yet another embodiment, the pulmonary disorder or injury is an interstitial lung disease (including congenital interstitial lung diseases, etc.).

Step (a), producing anterior foregut endoderm cells from mammalian pluripotent stem cells (PSCs), may last for about 2 days to about 8 days, about 3 days to about 7 days, about 3 days to about 6 days, about 3 days, or about 6 days. Step (a) may be conducted, for example, at a time point ranging from day 3 to day 8, or from day 4 to day 6, counting from the beginning of the method.

Step (b), culturing the anterior foregut endoderm cells in a suspension culture to generate at least one lung bud organoid (LBO), may last for about 2 days to about 30 days, about 5 days to about 28 days, about 10 days to about 25 days, about 15 days to about 25 days, about 16 days to about 23 days, about 10 days to about 16 days, about 10 days to about 30 days, about 10 days to about 20 days, about 16 days, or about 23 days. Step (b) may be conducted, for example, at a time point ranging from day 8 to day 30, or from day 10 to day 25, counting from the beginning of the method.

Step (c), embedding the LBO within a 3D matrix, may be conducted at a time point ranging from day 20 to day 30, or day 25, counting from the beginning of the method.

Step (d), culturing the embedded LBO to form branched LBO (BLBO), may last for about 20 days to about 200 days, about 30 days to about 180 days, about 50 days to about 160 days, about 100 days to about 200 days, about 20 days to about 50 days, about 20 days to about 30 days, about 10 days to about 30 days, or about 10 days to about 20 days. Step (d) may be conducted, for example, at a time point ranging from day 20 to day 180, counting from the beginning of the method.

In step (e), the LBO or BLBO is dissociated at a time point ranging from about day 20 to about day 180, or from about day 25 to about day 150, counting from the beginning of the method. In step (e), the dissociated LBO or BLBO may be cultured on feeder cells in a culture medium for desired time periods, and may be passaged indefinitely.

The culture medium may comprise an inhibitor of Rho kinase (ROCK). In one embodiment, the inhibitor of ROCK is Y27632.

In the culture medium, the inhibitor of ROCK may be at a concentration ranging from about 0.1 µM to about 100 µM, from about 1 µM to about 50 µM, from about 0.5 µM to about 25 µM, from about 1 µM to about 20 µM, from about 1 µM to about 10 µM, from about 5 µM to about 15 µM, from about 5 µM to about 10 µM, about 5 µM, or about 10 µM.

The culture medium may comprise a glycogen synthase kinase (GSK) inhibitor. In one embodiment, the GSK inhibitor is CHIR99021.

In the culture medium, the GSK inhibitor may be at a concentration ranging from about 0.1 µM to about 100 µM, from about 1 µM to about 50 µM, from about 0.5 µM to about 25 µM, from about 1 µM to about 20 µM, from about 1 µM to about 10 µM, from about 5 µM to about 15 µM, from about 5 µM to about 10 µM, about 5 µM, about 10 µM, or about 3 µM.

The culture medium may comprise one or more of FGF7, FGF10, bone morphogenic protein 4 (BMP4), retinoic acid, and combinations thereof. In one embodiment, one or more of FGF7, FGF10, and BMP4 is/are at a concentration of about 10 ng/ml. In one embodiment, retinoic acid is at a concentration of about 50 nM.

The culture medium may comprise one or more of insulin, EGF, hydrocortisone, cholera toxin, and combinations thereof.

In one embodiment, in step (e), the dissociated LBO or BLBO is first cultured in a first culture medium comprising an inhibitor of ROCK (e.g., Y27632), a GSK inhibitor (e.g., CHIR99021), FGF7, FGF10, BMP4 and/or retinoic acid, and then cultured in a second culture medium comprising an inhibitor of ROCK (e.g., Y27632), insulin, EGF, hydrocortisone and/or cholera toxin.

In one embodiment, the 3D matrix may be matrigel.

The feeder cells may be fibroblasts. In one embodiment, the fibroblasts are irradiated 3T3 cells (e.g., 3T3-J2 cells).

In one embodiment, in step (e), the LBO or BLBO is dissociated at a time point ranging from about day 20 to about day 180, or from about day 25 to about day 150, counting from the beginning of the method.

In one embodiment, in step (e), the LBO or BLBO may be dissociated to single cells or cell clusters.

The mammalian pluripotent stem cells (PSCs) may be human pluripotent stem cells (hPSCs).

The mammalian pluripotent stem cells (PSCs) may be embryonic stem cells (ESCs) and/or induced pluripotent stem cells (iPSCs).

The present disclosure also provides for lung progenitor cells generated by the present methods, or a cell population comprising the present lung progenitor cells generated by the present methods.

In certain embodiments, at least or about 20%, at least or about 30%, at least or about 40%, at least or about 50%, at least or about 60%, at least or about 70%, at least or about 80%, at least or about 90%, of the cell population expresses NKX2.1, SOX2, SOX9, or combinations thereof. In one embodiment, at least or about 70% of the cell population expresses NKX2.1, SOX2, SOX9, or combinations thereof.

In certain embodiments, at least or about 20%, at least or about 30%, at least or about 40%, at least or about 50%, at least or about 60%, at least or about 70%, at least or about 80%, at least or about 90%, of the cell population expresses KRT5, P63, ITGB4, NGFR, or combinations thereof. In one embodiment, at least or about 30% of the cell population expresses KRT5, P63, ITGB4, NGFR, or combinations thereof.

Also encompassed by the present disclosure is a method of treating a pulmonary disorder or injury in a subject in need thereof. The method may comprise administering to the subject a therapeutically effective amount of the present lung progenitor cells.

The present disclosure provides for a pharmaceutical composition comprising the present lung progenitor cells, cell population, and/or biological scaffold. The pharmaceutical composition may further comprise a pharmaceutically and/or physiologically acceptable vehicle or carrier, such as buffered saline or other buffers, e.g., HEPES, to maintain pH at appropriate physiological levels, and, optionally, other medicinal agents, pharmaceutical agents, stabilizing agents, buffers, carriers, adjuvants, diluents, etc. Exemplary physiologically acceptable carriers include sterile, pyrogen-free water and sterile, pyrogen-free phosphate buffered saline.

The present lung progenitor cells, cell population, biological scaffold, or pharmaceutical composition may be engrafted, transplanted, or implanted into a subject. The present lung progenitor cells, cell population, biological scaffold, or pharmaceutical composition may be administered to the subject by routes including, but not limited to, intranasal, direct delivery to a desired tissue/organ (e.g., the lung, airway or nasal cavity of a subject), oral, inhalation, intratracheal, intravenous, intramuscular, subcutaneous, intradermal, and other parental routes of administration. Additionally, routes of administration may be combined, if desired.

The lung progenitor cells may be non-syngeneic with the subject. The lung progenitor cells may be syngeneic with the subject. The lung progenitor cells may be allogeneic or xenogeneic with the subject.

The present disclosure provides for a biological scaffold comprising the present lung progenitor cells.

In one embodiment, step (b) may comprise culturing the cells in a normoxic incubator.

The present disclosure provides for a method of treating a pulmonary disorder or injury in a subject in need thereof. The method may comprise engrafting a therapeutically effective amount of the present lung progenitor cells into the lung, airway or nasal cavity of the subject.

The engrafted cells may integrate into epithelium.

The pulmonary disorder or injury may be an interstitial lung disease or a congenital surfactant deficiency.

Non-limiting examples of pulmonary disorders or injuries include, cystic fibrosis; emphysema; chronic obstructive pulmonary disease (COPD); interstitial lung diseases including pulmonary fibrosis, idiopathic pulmonary fibrosis (IPF), Hermansky-Pudlak Syndrome (HPS), hypersensitivity pneumonitis, sarcoidosis, asbestosis, autoimmune-mediated interstitial lung disease; pulmonary hypertension; lung cancer; acute lung injury (adult respiratory distress syndrome); respiratory distress syndrome of prematurity, chronic lung disease of prematurity (bronchopulmonary dysplasia); congenital surfactant deficiencies, including surfactant protein B deficiency, surfactant protein C deficiency, ABCA3 deficiency; ciliopathies; congenital diaphragmatic hernia; pulmonary alveolar proteinosis; pulmonary hypoplasia; lung injury, and combinations thereof. The pulmonary disorder or injury may be HPS-associated interstitial pneumonia (HP-SIP).

The 3D (three-dimensional) matrix may include one or more extracellular matrix (ECM) proteins. The 3D matrix may include, but are not limited to, matrigel, fibronectin, collagen (e.g., collagen I, collagen IV, etc.), collagen derivatives, gelatin, laminin, collagen IV, heparan sulfate proteoglycans, entactin/nidogen, cellulose, cellulose derivatives, cellulose polymers, proteoglycans, heparin sulfate, chondroitin sulfate, keratin sulfates, hyaluronic acid, elastin, fibrin, chitosan, alginate, vinculin, agar, agarose, hyaluronic acid, and combinations thereof. The 3D matrix may comprise one or more polymers including, but not limited to: polyethylene-imine and dextran sulfate, poly(vinylsiloxane) ecopolymerepoly-ethyleneimine, phosphorylcholine, poly(ethylene glycol), poly(lactic-glycolic acid), poly(lactic acid), polyhydroxyvalerte and copolymers, polyhydroxybutyrate and copolymers, polydiaxanone, polyanhydrides, polypeptides, poly(orthoesters), polyesters, and combinations thereof. the 3D matrix may comprise one or more matrices described in Gjorevsky et al, Nature, 2016, 539 (7630):560-564 and DiMarco et al., Biomater Sci. 2015, 3(10):1376-85.

In one embodiment, the 3D matrix may comprise a gelatinous extracellular protein mixture secreted by Engelbreth-Holm-Swarm (EHS) mouse sarcoma cells. In one embodiment, the 3D matrix may comprise Matrigel. Matrigel may comprise laminin, collagen IV, heparan sulfate proteoglycans, entactin/nidogen, TGF-beta, epidermal growth factor, insulin-like growth factor, fibroblast growth factor, and tissue plasminogen activator, additional proteins, or combinations thereof.

In certain embodiments, the iPSC cells may be from a subject having at least one mutation in a lung disease-associated gene, and the iPSC cells have been genetically altered to correct the gene mutation. In one embodiment, the iPSCs may be genetically altered via the CRISPR/Cas system.

The organoid, cell aggregates, or cell clusters may be dissociated by an enzymatic treatment. For example, the enzyme(s) may comprise at least one protease. The organoid, cell aggregates, or cell clusters may be dissociated by dispase, accutase, trypsin, and/or collagenase (e.g., collagenase I, II, III, and IV, etc.).

The dissociated LBO or BLBO may be plated on feeder cells in a culture medium. In certain embodiments, the ratio of the number of cells from dissociated LBO or BLBO to the number of feeder cells may range from about 1:1 to about 1:100, from about 1:1 to about 1:80, 1:1 to about 1:60, from about 1:1 to about 1:50, from about 1:1 to about 1:30, from about 1:1 to about 1:20, from about 1:1 to about 1:15, from about 1:1 to about 1:10, from about 1:1 to about 1:5, from about 2:1 to about 1:2, from about 5:1 to about 1:20, from about 10:1 to about 1:50, from about 5:1 to about 1:100, from about 10:1 to about 1:1000, from about 15:1 to about 1:500, from about 10:1 to about 1:200, from about 5:1 to about 1:10, from about 6:1 to about 1:25, from about 5:1 to about 1:1, from about 1:1 to about 1:25, from about 3:1 to about 1:1, about 1:20, or about 1:10. In certain embodiments, the ratio of the number of cells from dissociated LBO or BLBO to the number of feeder cells is about 1:10.

In IPF, mutation in surfactant proteins (SFTP) A2[17] and in the Brichos domain of SPFTPC[18,19] result in an unfolded protein response in the endoplasmic reticulum (UPR$^{ER}$)[16,20] suggesting proteotoxic stress to ATII cells as a pathogenetic mechanism.[20] UPR$^{ER}$,[20-22] low autophagy,[23-26] mitochondrial dysfunction,[27] and apoptosis are also observed in sporadic IPF. 8 to 15% of patients with familial IPF have heterozygous mutations in the reverse transcriptase (hTERT) or RNA component (hTR) of telomerase, leading to accelerated age-associated telomere shortening.[28-33] Furthermore, several susceptibility loci have been identified through exome sequencing that affect telomere length.[34] The association between telomeropathy and IPF[28-33] suggests a role for ATII cells, as these can self-renew and replace damaged ATI cells to restore alveolar integrity after injury in the mouse.[35-37] Telomere dysfunction has recently been shown to cause failure of ATII as stem cells, and to increase susceptibility to bleomycin-induced toxicity in mice.[38]

We have previously described (WO2018/176044) directed differentiation of iPSCs into lung in 2D cultures[124-126]. Thus, definitive endoderm (DE), anterior foregut endoderm (AFE), ventral AFE and lung progenitors (LPs), are sequentially specified followed by further differentiation into a mixture of alveolar and airway cells[100,124,125,127-132]. Based on these 2D models, we reported a 3D model consisting of lung bud organoids generated in suspension from early AFE, that were endowed with the expression patterns associated with lung buds in vivo, followed by embedding in Matrigel[128], where branching morphogenesis with predominant generation of ATII cells ensued. Briefly, early during induction of a ventral lung fate from AFE, adherent structures formed that detached easily and expanded in suspension culture as clumps of cells in the presence of BMP4, FGF10, FGF7, retinoic acid (RA) and the GSK3β antagonist, CHIR99201, factors shown previously to be required for lung development[3,76]. Expression analysis revealed that these consisted of endoderm compatible with lung buds (FOXA1$^+$SOX2$^+$NKX2.1$^+$SHH$^+$) interspersed with mesodermal cells (PDGFRa$^+$TBX4$^+$CD90$^+$HOXA5$^+$GLI1$^+$HHIP$^+$PTCH$^+$). We therefore named these structures lung bid organoids or LBOs. After plating in Matrigel at d25 of suspension cultures, each LBO developed into a branching colony that kept expanding for up to 180 days. Expression analysis and structural features indicated that the branching structures reached the second trimester of human gestation[128]. The dilated tips contain predominantly ATII cells that could take-up and secrete surfactant proteins. Importantly for therapeutic treatments, this model recapitulates several features of human development.

Culture and expansion of native DTPs has been reported[92,98,99]. Nichane et al.[99] used isolated DTPs based on expression of a distal Sox9 reporter. Some cultures have reportedly been maintained for 9 months, but it is unclear to what extent function, gene expression and morphology were maintained. Nicholic et al. dissected distal tips from early stage fetal lungs and could obtain limited expansion of the cells in vitro. Miller et al. generated lung organoids that may contain DTPs. They report these could be replated which however showed spontaneous differentiation.

It would be highly desirable to be able to utilize in vitro generated lung tissue for regenerative purposes. Achieving the correct architecture and scale is enormously challenging however. Alternatively, epithelium in lung and airways could be replaced with cells capable of regenerating all epithelial cells in the lung, including fetal and postnatal lung progenitor populations.

During fetal lung development, lung buds develop through a stereotyped branching process of stalks with proliferating progenitors at the tips (pseudoglandular stage). The proliferating cells at the tips of branching fetal lung at the pseudoglandular stage are of major interest, as these cells and their progeny are believed to give rise to all cells of the respiratory system. Generating this cell type from human pluripotent stem cells in unlimited quantities would be a major advance to the field, as they could theoretically be used to repopulate native lungs with healthy cells.

The present disclosure provides a method of generating, and expanding from, human pluripotent stem cells (hPSCs) cells that are close to distal tip progenitors. The distal tip progenitors arise during fetal lung development and are the precursors of all cells in fully mature lungs and airways.

In previous experiments, cells that are phenotypically very similar to distal tip cells were generated from lung bud organoids (LBO)-derived matrigel organoids. A 3D model of human lung development was described in WO2018-176044 and Chen et al. 2017, which includes suspension culture of lung bud organoids (LBOs) generated from early anterior foregut endoderm in vitro followed by embedding in a 3D matrix (e.g., Matrigel), where mesenchyme can develop and branching morphogenesis may ensue.

The present data and results illustrate for the first time, the ability to dissociate the organoids at various stages of development (e.g., ranging from day 25, the LBO suspension cultures stage, to day 150, the stage of fully developed branching colonies in Matrigel) and to culture those in 2D on feeder cells (e.g., 3T3-J2 cells) in the presence of a ROCK inhibitor (e.g., Y27632) and growth factors (e.g., the same growth factor combination that drives the development of branching organoids in Matrigel, such as the GSK3 inhibitor CHIR99021, FGF7, FGF10, retinoic acid and BMP4). These culturing conditions may result in proliferation cells that may grow in clusters. The cells may be passaged indefinitely in these conditions.

Figures 2A, 2B:
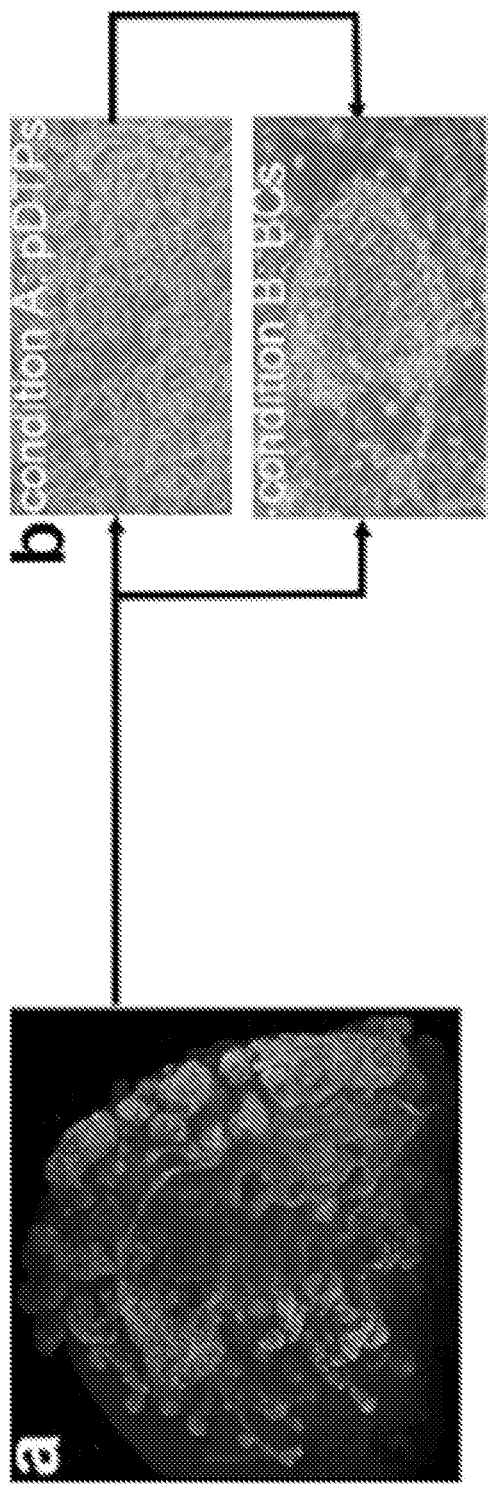
FIGS. 2A-2D are images showing morphology and marker expressions of condition A (pDTPs) and condition B cells expanded from lung bud organoids.

The present pluripotent stem cells may be substantially equivalent to distal tip progenitors (referred to as putative distal tip progenitors or pDTPs). In certain embodiments, the cells on the edges of the clusters express the basal cell marker, P63, are less proliferative than the cells within the clusters, that expressed SOX2, and SOX9, and are very highly proliferative as evaluated by ki67 staining (FIG. 2). In certain embodiments, transfer of the cells to culture conditions that are known to be conducive to the expansion of mature epithelial progenitors may result in a culture that is majority P63+, and with co-expression of KRT5, CD104, and NGFR similar to bona fide basal cells, the stem cells of the airway, and ocSMA and SOX9, markers of submucosal gland myoepithelial cells, precursors of basal cells. In air-liquid interface cultures (FIG. 3), ciliated and goblet cells may be generated.

These lung progenitors have been shown to be able to engraft the lungs, potentially serving as a regenerative therapy for treating various lung diseases, conditions, and injuries (See FIGS. 6-9, and further described below).

As described herein, two types of cells have been generated: condition A cells (putative distal tip progenitors or pDTPs, which are however heterogenous and also include P63+ cells) and condition B cells (basal cell-like and SMG myoepithelial-like).

These cells may be generated from human pluripotent stem cells, such as iPS and/or ES cells. In one embodiment, such cells may be generated from an expandable and patient-specific source.

In certain embodiments, lung progenitors may be generated and expanded from a patient-specific source (i.e., iPS cells), which can provide cell-based regenerative treatments for repopulating healthy lung tissue in diseased patient lungs.

The lung progenitor cells and expansion methods described herein provide the first methods for therapeutic treatment of lung epithelial diseases with human iPS cells that have the capacity to repopulate the lung airway cells.

In additional embodiments the lung progenitor cells described herein will also be useful for disease modeling and drug testing.

The cell culture medium may be a serum-free medium or a serum-containing medium.

Alternative approaches to achieve replacement of diseased lung and airways with stem cell-derived cells include the use of tissues reconstituted within decellularized lung matrices. The present lung progenitors may be used to seed a decellularized lung matrix. Rat lungs can be decellularized by perfusion with mild detergents, and repopulated with fetal or neonatal lung cell suspensions on the airway side and endothelial cells on the vascular side[2,44]. Although lung histology was not normal, there was some evidence for region-specific distribution of epithelial cells types. Furthermore, such repopulated, decellularized lungs could be ventilated ex vivo, and maintained gas exchange for up to 6 hours after orthotopic transplantation, although moderate bleeding, extensive thrombosis[2] and edema occurred[44]. While allogeneic matrices could be used, the cells seeded on these matrices preferably are autologous, and would therefore be derived from autologous postnatal lung stem cells or from cells differentiated from autologous induced pluripotent state cells (iPSCs)[45-47](FIG. 1). The present methods can generate sufficient numbers of autologous, iPSC-derived cells for seeding of decellularized lung matrices with the appropriate maturity, variety and ratio of epithelial cells normally found in the lung. Furthermore, the present methods and cells can ensure that planar polarity is established correctly so that all cilia beat coordinately. This is important for proper mucociliary function in the regenerated tissue. Finally, the present methods and cells can ensure that the regionally distinct postnatal stem and progenitor cells are included to endow the graft with endogenous regenerative capacity[48].

Inhibitor of Rho Kinase (ROCK)

The inhibitor of ROCK (or ROCK inhibitor) may be any agent that decreases the level and/or activity of ROCK. The ROCK inhibitors can be small organic or inorganic molecules; saccharides; oligosaccharides; polysaccharides; biological macromolecules, e.g., peptides, proteins, and peptide analogs and derivatives; peptidomimetics; nucleic acids and nucleic acid analogs and derivatives (including but not limited to microRNAs, siRNAs, shRNAs, antisense RNAs, a ribozymes, and aptamers); an extract made from biological materials such as bacteria, plants, fungi, or animal cells; animal tissues; naturally occurring or synthetic compositions; and any combinations thereof.

ROCK inhibitors include, but are not limited to, a small organic molecule ROCK inhibitor selected from the group consisting of N-[(1S)-2-hydroxy-1-phenylethyl]-N'-[4-(4-pyridinyl)phenyl]-urea (AS1892802), fasudil hydrochloride (also known as HA 1077), N-[3-[[2-(4-amino-1,2,5-oxadiazol-3-yl)-1-ethyl-1H-imidazo[4,5-c]pyridin-6-yl]oxy]phenyl]-4-[2-(4-morpholinyl)ethoxy]benzamide (GSK269962), 4-[4-(Trifluoromethyl)phenyl]-N-(6-Fluoro-1H-indazol-5-yl)-2-methyl-6-oxo-1,4,5,6-tetrahydro-3-pyridinecarboxamide (GSK 429286), (5)-(+)-2-Methyl-1-[(4-methyl-5-isoquinolinyl)sulfonyl]-hexahydro-1H-1,4-diazepine dihydrochloride (H 1152 dihydrochloride), (S)-(+)-4-Glycyl-2-methyl-1-[(4-methyl-5-isoquinolinyl)sulfonyl]-hexahydro-1H-1,4-diazepine dihydrochloride (glycyl-H 1152 dihydrochloride), N-[(3-Hydroxyphenyl)methyl]-N'-[4-(4-pyridinyl)-2-thiazolyl]urea dihydrochloride (RKI 1447 dihydrochloride), (3S)-1-[[2-(4-Amino-1,2,5-oxadiazol-3-yl)-1-ethyl-1H-imidazo[4,5-c]pyridin-7-yl]carbonyl]-3-pyrrolidinamine dihydrochloride (SB772077B dihydrochloride), N-[2-[2-(Dimethylamino)ethoxy]-4-(1H-pyrazol-4-yl)phenyl-2,3-dihydro-1,4-benzodioxin-2-carboxamide dihydrochloride (SR 3677 dihydrochloride), and trans-4-[(1R)-1-Aminoethyl]-N-4-pyridinylcyclohexanecarboxamide dihydrochloride (Y-27632 dihydrochloride), N-Benzyl[2-(pyrimidin-4-yl)amino]thiazole-4-carboxamide (Thiazovivin), a isoquinolinesulfonamide compound (Rho Kinase Inhibitor), N-(4-Pyridyl)-N'-(2,4,6-trichlorophenyl) urea (Rho Kinase Inhibitor II), 3-(4-Pyridyl)-1H-indole (Rho Kinase Inhibitor III, Rockout), and 4-pyrazoleboronic acid pinacol ester; a Rock antibody commercially available from Santa Cruz Biotechnology selected from the group consisting of Rock-1 (B1), Rock-1 (C-19), Rock-1 (H-11), Rock-1 (G-6), Rock-1 (H-85), Rock-1 (K-18), Rock-2 (C-20), Rock-2 (D-2), Rock-2 (D-11), Rock-2 (N-19), Rock-2 (H-85), Rock-2 (30-J); a ROCK CRISPR/Cas9 knockout plasmid selected from the group consisting of Rock-1 CRISPR/Cas9 KO plasmid (h), Rock-2 CRISPR/Cas9 KO plasmid (h), Rock-1 CRISPR/Cas9 KO plasmid (m), Rock-2 CRISPR/Cas9 KO plasmid (m); a ROCK siRNA, shRNA plasmid and/or shRNA lentiviral particle gene silencer selected from the group consisting of Rock-1 siRNA (h): sc-29473, Rock-1 siRNA (m): sc-36432, Rock-1 siRNA (r): sc-72179, Rock-2 siRNA (h): sc-29474, Rock-2 siRNA (m): sc-36433, Rock-2 siRNA (r): se-108088.

In certain embodiments, the ROCK inhibitor decreases the level and/or activity of ROCK in cells or cell culture medium by at least or about 5%, at least or about 10%, at least or about 20%, at least or about 30%, at least or about 40%, at least or about 50%, at least or about 60%, at least or about 70%, at least or about 80%, at least or about 90%, or at least or about 95%. In one embodiment, a ROCK inhibitor may completely inhibit the level and/or activity of ROCK in the cells or cell culture medium.

The ROCK inhibitor may be Y27632 ((1R,4r)-4-((R)-1-aminoethyl)-N-(pyridin-4-yl)cyclohexanecarboxamide). Y27632 may have the following structure.

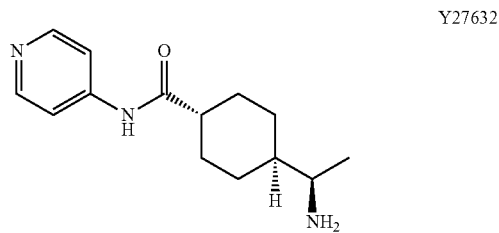 [SMILES: C[C@@H](N)[C@H]1CC[C@H](C(=O)Nc2ccncc2)CC1]

Y27632

In certain embodiments, the ROCK inhibitor (e.g., Y27632 or any agent described herein) is used at a concentration ranging from about 1 μM to about 30 μM, e.g., at least or about 1 μM, at least or about 2 μM, at least or about 3 μM, at least or about 4 μM, at least or about 5 μM, at least or about 6 μM, at least or about 7 μM, at least or about 8 μM, at least or about 9 μM, at least or about 10 μM, at least or about 11 μM, at least or about 12 μM, at least or about 13 μM, at least or about 14 μM, at least or about 15 μM, at least or about 16 μM, at least or about 17 μM, at least or about 18 μM, at least or about 19 μM, at least or about 20 μM, at least or about 21 μM, at least or about 22 μM, at least or about 23 μM, at least or about 24 μM, at least or about 25 μM, at least or about 26 μM, at least or about 27 μM, at least or about 28 μM, at least or about 29 μM, or at least or about 30 μM, or higher concentrations. In another embodiment, the ROCK inhibitor is used at a concentration ranging from about 0.1 μM to about 1 μM, e.g., at least or about 0.1 μM, at least or about 0.2 μM, at least or about 0.3 μM, at least or about 0.4 μM, at least or about 0.5 μM, at least or about 0.6 μM, at least or about 0.7 μM, at least or about 0.8 μM, at least or about 0.9 μM, or at least or about 1 μM.

An effective amount of the ROCK inhibitor (e.g., Y27632 or any agent described herein) for use in the present methods can be, for example, between about 0.1 μM and about 110 μM. In some aspects, an effective amount of ROCK inhibitor (e.g., Y27632 or any agent described herein) is 10 μM.

Growth Factors and Other Factors

The cell culture medium may comprise one or more factors selected from the group consisting of Wnt ligands, Wnt signaling activators (or Wnt agonists), BMPs, epidermal growth factors (EGFs), fibroblast growth factors (FGFs), and retinoic acid.

The cell culture medium may comprise one or more agonists of the Wnt signaling, FGF signaling, BMP signaling, and EGF signaling pathways. For example, the cell culture medium may comprise 1 or more, 2 or more, 3 or more, 4 or more, 5 or more, 6 or more, 7 or more, 8 or more, 9 or more, or 10 or more, agonists of the Wnt signaling, FGF signaling, BMP signaling, and EGF signaling pathways.

The cell culture medium may comprise at least one growth factor. In certain embodiments, the grow factor comprises an agonist (or activator) of the Wnt signaling. The "Wnt signaling activator" or "Wnt signaling agonist" as used herein refers to a substance that activates the Wnt signaling pathway. Examples of the Wnt signaling activator include glycogen synthase kinase (GSK) inhibitors such as GSK3 inhibitors. In some embodiments, activation of Wnt/beta-catenin signaling is achieved by inhibiting GSK3 phosphotransferase activity or GSK3 binding interactions. GSK3 inhibition can be achieved in a variety of ways including, but not limited to, providing small molecules that inhibit GSK3 phosphotransferase activity, RNA interference (RNAi such as small interfering RNAs or siRNAs, and short hairpin RNAs or shRNAs) against GSK3, and overexpression of dominant negative form of GSK3. Dominant negative forms of GSK3 are known in the art as described, e.g., in Hagen et al. (2002), J. Biol. Chem., 277(26):23330-23335, which describes a Gsk3 comprising a R96A mutation.

In some embodiments, GSK3 is inhibited by contacting a cell with a small molecule that inhibits GSK3 phosphotransferase activity or GSK3 binding interactions. Suitable small molecule Gsk3 inhibitors include, but are not limited to, CHIR99021, CHIR98014, BIO-acetoxime, 6-Bromoindirubin-3'-oxime (BIO), LiCl, SB 216763, SB 415286, AR A014418, Kenpaullone, 1-Azakenpaullone, Bis-7-indolyl-maleimide, TWS119, and any combinations thereof.

In certain embodiments, the GSK3 inhibitor (e.g., CHIR99021 or any agent described herein) is used at a concentration ranging from about 1 µM to about 100 µM, from about 1 µM to about 30 µM, from about 1 µM to about 20 µM, at least or about 1 µM, at least or about 2 µM, at least or about 3 µM, at least or about 4 µM, at least or about 5 µM, at least or about 6 µM, at least or about 7 µM, at least or about 8 µM, at least or about 9 µM, at least or about 10 µM, at least or about 11 µM, at least or about 12 µM, at least or about 13 µM, at least or about 14 µM, at least or about 15 µM, at least or about 16 µM, at least or about 17 µM, at least or about 18 µM, at least or about 19 µM, or at least or about 20 µM, or higher concentrations. In another embodiment, the small molecule GSK3 inhibitor is used at a concentration ranging from about 0.1 µM to about 1 µM, e.g., at least or about 0.1 µM, at least or about 0.2 µM, at least or about 0.3 µM, at least or about 0.4 µM, at least or about 0.5 µM, at least or about 0.6 µM, at least or about 0.7 µM, at least or about 0.8 µM, at least or about 0.9 µM, or at least or about 1 µM.

In other embodiments, GSK3 activity is inhibited by RNA interference knockdown of GSK3. For example, v expression levels can be knocked-down using commercially available siRNAs against v, e.g., SignalSilence® GSK-3alpha/beta siRNA (catalog #6301 from Cell Signaling Technology, Danvers, Mass.), or a retroviral vector with an inducible expression cassette for v, e.g., a commercially available Tet-inducible retroviral RNA interference (RNAi) system from Clontech (Mountain View, Calif., Catalog No. 630926), or a cumate-inducible system from Systems Biosciences, Inc. (Mountain View, Calif.), e.g., the SparQ® system, catalog no. QM200PA-2.

In some embodiments, an agonist of Wnt signaling is Wnt3a, which mediates canonical Wnt signaling; any inducer of canonical Wnt signaling can be used, for example, Wnt/beta-catenin pathway agonists glycogen synthase kinase 3 beta (GSK3b) inhibitors, or casein kinase 1 (CK1) inhibitors. Non-limiting examples of Wnt agonists include DNA encoding β-catenin (e.g., DNA encoding β-catenin, vectors encoding β-catenin, etc.), β-catenin polypeptides, one or more Wnt/β-catenin pathway agonists (e.g., selected from the group consisting of Wnt ligands, DSH/DVL-1, -2, -3, LRP6N, WNT3A, WNTSA, and WNT3A, 5A), one or more glycogen synthase kinase (GSK3β) inhibitors (e.g., lithium chloride (LiCl), Purvalanol A, olomoucine, alsterpaullone, kenpaullone, benzyl-2-methyl-1,2,4-thiadiazolidine-3,5-dione (TDZD-8), 2-thio(3-iodobenzyl)-5-(1-pyridyl)-[1,3,4]-oxadiazole (GSK3 inhibitor II), 2,4-dibenzyl-5-oxothiadiazolidine-3-thione (OTDZT), (2'Z, 3'E)-6-Bromoindirubin-3'-oxime (BIO), α-4-Dibromoacetophenone (i.e., Tau Protein Kinase I (TPK I) Inhibitor), 2-Chloro-1-(4,5-dibromo-thiophen-2-yl)-etha-none, N-(4-Methoxybenzyl)-N'-(5-nitro-1,3-thiazol-2-yl) urea (AR-A014418), indirubin-5-sulfonamide; indirubin-5-sulfonic acid (2-hydroxyethyl)-amide indirubin-3'-monoxime; 5-iodo-indirubin-3'-monoxime; 5-fluoroindirubin; 5,5'-dibromoindirubin; 5-nitroindirubin; 5-chloroindirubin; 5-methylindirubin, 5-bromoindirubin, 4-Benzyl-2-methyl-1,2,4-thiadiazolidine-3,5-dione (TDZD-8), 2-thio(3-iodobenzyl)-5-(1-pyridyl)[1,3,4]-oxadiazole (GSK3 inhibitor II), 2,4-Dibenzyl-5-oxothiadiazolidine-3-thione (OTDZT), (2'Z,3'E)-6-Bromoindirubin-3'-oxime (BIO), α-4-Dibromoacetophenone (i.e., Tau Protein Kinase I (TPK I) Inhibitor), 2-Chloro-1-(4,5-dibromo-thiophen-2-yl)-ethanone, (vi) N-(4-Methoxybenzyl)-N'-(5-nitro-1,3-thiazol-2-yl)urea (AR-A014418), H-KEAPPAPPQSpP-NH2 (L803) and Myr-N-GKEAPPAPPOSpP-NH2 (L803-mts)), one or more anti-sense RNA or siRNA that bind specifically to GSK3 (3 mRNA, one or more casein kinase 1 (CK1) inhibitors (e.g., antisense RNA or siRNA that binds specifically to CK1 mRNA), one or more protease inhibitors, one or more proteasome inhibitors. When Wnt3a is used in the methods described herein, Wnt3a is present in cultures at a concentration of about 1 ng/ml to 10 µg/ml, 10 ng/ml to 1 µg/ml, 10 ng/ml to 500 ng/ml, 10 ng/ml to 250 ng/ml, or 10 ng/ml to 100 ng/ml. In certain embodiments, Wnt3a is present in cultures at a concentration of about 25 ng/ml to 150 ng/ml, 50 ng/ml to 150 ng/ml or 75 ng/ml to 150 ng/ml. In further preferred embodiments, Wnt3a is present in cultures at a concentration of about 100 ng/ml.

The cell culture medium may comprise one or more agonists of FGF signaling, e.g., FGF7, FGF9, or FGF10. In some embodiments, other agonists of FGF signaling can be used, e.g., FGF1, FGF2, FGF3, FGF5, FGF6, FGF9, FGF11, FGF12, FGF13, FGF14, FGF15, FGF16, FGF17, FGF18, FGF19, FGF20, FGF21, FGF22, or FGF23. For example, FGF (e.g., FGF7 or FGF10 or any FGF as described herein) may be present in the culture medium at a concentration of about 1 ng/ml to 10 µg/ml, 10 ng/ml to 1 µg/ml, 10 ng/ml to 500 ng/ml, 10 ng/ml to 250 ng/ml, 10 ng/ml to 100 ng/ml, at least or about 1 ng/ml, at least or about 2 ng/ml, at least or about 3 ng/ml, at least or about 4 ng/ml, at least or about 5 ng/ml, at least or about 6 ng/ml, at least or about 7 ng/ml, at least or about 8 ng/ml, at least or about 9 ng/ml, at least or about 10 ng/ml, at least or about 11 ng/ml, at least or about 12 ng/ml, at least or about 13 ng/ml, at least or about 14 ng/ml, at least or about 15 ng/ml, at least or about 16 ng/ml, at least or about 17 ng/ml, at least or about 18 ng/ml, at least or about 19 ng/ml, at least or about 20 ng/ml, at least or about 25 ng/ml, at least or about 30 ng/ml, at least or about 35 ng/ml, at least or about 40 ng/ml, at least or about 45 ng/ml, at least or about 50 ng/ml, at least or about 55 ng/ml, at least or about 60 ng/ml, at least or about 65 ng/ml, at least or about 70 ng/ml, at least or about 75 ng/ml, at least or about 80 ng/ml, at least or about 85 ng/ml, at least or about 90 ng/ml, at least or about 95 ng/ml, or at least or about 100 ng/ml. In certain embodiments, FGF7 and/or FGF10 are present in the culture medium at a concentration of about 25 ng/ml to 150 ng/ml, 50 ng/ml to 150 ng/ml or 75 ng/ml to 150 ng/ml. In certain embodiments, FGF7 and/or FGF10 are present in the culture medium at a concentration of about 10 ng/ml.

The cell culture medium may comprise one or more agonists of the EGF signaling such as EGF. For use in the methods described herein, EGF is present in cultures at a concentration of about 0.1 ng/ml to 20 µg/ml, about 1 ng/ml to 10 µg/ml, 10 ng/ml to 1 µg/ml, 10 ng/ml to 500 ng/ml, 10 ng/ml to 250 ng/ml, or 10 ng/ml to 100 ng/ml. In preferred embodiments, EGF is present in cultures at a concentration of about 25 ng/ml to 150 ng/ml, 50 ng/ml to 150 ng/ml or 75 ng/ml to 150 ng/ml. In one embodiment, one or more EGFs is/are present in the culture medium at a concentration of about 0.1 ng/ml.

The cell culture medium may comprise one or more agonists of BMP signaling such as BMP1, BMP2, BMP3, BMP4, BMP5, BMP6, BMP7, BMP8, BMP9, BMP10, BMP11, BMP12, BMP13, BMP14, BMP15, BMP16, BMP17, BMP18, BMP19, or BMP20. In certain embodiments, any of BMP 2-7 is/are used. For use in the methods described herein, BMP may be present in cultures at a concentration of about 1 ng/ml to 10 µg/ml, 10 ng/ml to 1 µg/ml, 10 ng/ml to 500 ng/ml, 10 ng/ml to 250 ng/ml, or 10 ng/ml to 100 ng/ml. In preferred embodiments, BMP-4 is present in cultures at a concentration of about 25 ng/ml to 150 ng/ml, 50 ng/ml to 150 ng/ml or 75 ng/ml to 150 ng/ml. In certain embodiments, one or more BMP is/are present in cultures at a concentration of about 0.5 ng/ml, about 3 ng/ml, and/or about 10 ng/ml. For example, BMP (e.g., BMP4 or any BMP as described herein) may be present in the culture medium at a concentration of about 1 ng/ml to 10 µg/ml, 10 ng/ml to 1 µg/ml, 10 ng/ml to 500 ng/ml, 10 ng/ml to 250 ng/ml, 10 ng/ml to 100 ng/ml, at least or about 1 ng/ml, at least or about 2 ng/ml, at least or about 3 ng/ml, at least or about 4 ng/ml, at least or about 5 ng/ml, at least or about 6 ng/ml, at least or about 7 ng/ml, at least or about 8 ng/ml, at least or about 9 ng/ml, at least or about 10 ng/ml, at least or about 11 ng/ml, at least or about 12 ng/ml, at least or about 13 ng/ml, at least or about 14 ng/ml, at least or about 15 ng/ml, at least or about 16 ng/ml, at least or about 17 ng/ml, at least or about 18 ng/ml, at least or about 19 ng/ml, at least or about 20 ng/ml, at least or about 25 ng/ml, at least or about 30 ng/ml, at least or about 35 ng/ml, at least or about 40 ng/ml, at least or about 45 ng/ml, at least or about 50 ng/ml, at least or about 55 ng/ml, at least or about 60 ng/ml, at least or about 65 ng/ml, at least or about 70 ng/ml, at least or about 75 ng/ml, at least or about 80 ng/ml, at least or about 85 ng/ml, at least or about 90 ng/ml, at least or about 95 ng/ml, or at least or about 100 ng/ml. In certain embodiments, BMP (e.g., BMP4 or any BMP as described herein) is present in the culture medium at a concentration of about 25 ng/ml to 150 ng/ml, 50 ng/ml to 150 ng/ml or 75 ng/ml to 150 ng/ml. In certain embodiments, BMP (e.g., BMP4 or any BMP as described herein) is present in the culture medium at a concentration of about 10 ng/ml.

The cell culture medium may comprise retinoic acid. Retinoic acid may be all-trans retinoic acid, 9-cis retinoic acid, 13-cis retinoic acid, etc. In certain embodiments, retinoic acid is used at a concentration ranging from about 1 nM to about 100 nM, from about 20 nM to about 80 nM, from about 30 nM to about 60 nM, at least or about 10 nM, at least or about 20 µM, at least or about 30 nM, at least or about 40 nM, at least or about 50 nM, at least or about 60 nM, at least or about 70 nM, at least or about 80 nM, at least or about 90 nM, at least or about 100 nM, at least or about 15 nM, at least or about 25 nM, at least or about 35 nM, at least or about 45 nM, at least or about 55 nM, at least or about 65 nM, at least or about 75 nM, at least or about 85 nM, at least or about 95 nM, or at least or about 5 nM, or higher concentrations. In another embodiment, retinoic acid is used at a concentration ranging from about 40 nM to about 60 nM, e.g., at least or about 30 nM, at least or about 70 nM, at least or about 41 nM, at least or about 42 nM, at least or about 43 nM, at least or about 44 nM, at least or about 46 nM, at least or about 47 nM, at least or about 48 nM, or at least or about 49 nM.

Feeder Cells

As used herein, feeder cells are intended to mean supporting cell types used alone or in combination. The cell type may further be of human or other species (e.g., mouse) origin. The tissue from which the feeder cells may be derived include embryonic, fetal, neonatal, juvenile or adult tissue, and it further includes tissue derived from skin, including foreskin, umbilical cord, muscle, lung, epithelium, placenta, fallopian tube, glandula, stroma or breast. The feeder cells may be derived from cell types pertaining to fibroblasts, fibrocytes, myocytes, keratinocytes, endothelial cells and epithelial cells. Examples of specific cell types that may be used for deriving feeder cells include embryonic fibroblasts, extraembryonic endodermal cells, extraembryonic mesoderm cells, fetal fibroblasts and/or fibrocytes, fetal muscle cells, fetal skin cells, fetal lung cells, fetal endothelial cells, fetal epithelial cells, umbilical cord mesenchymal cells, placental fibroblasts and/or fibrocytes, placental endothelial cells.

The feeder cells may be fibroblasts, such as human foreskin fibroblasts (hFF) or mouse embryonic fibroblast (MEF) cells (e.g., 3T3 cells). The feeder cells may be SNL76/7 cells, and/or 10T1/2 cells.

The feeder cells may comprise irradiated cells such as irradiated fibroblasts. These feeder cells may be used after exposed to radiation or treated with a cell division inhibitor (such as mitomycin C) to stop the cell division.

The term "pluripotent stem cells (PSCs)" as used herein refers to pluripotent stem cells that may include embryonic stem cells (ESCs) and induced pluripotent stem cells (iPSCs). Derived from the inner cell mass of the blastocyst, ESCs can be maintained in a pluripotent state in vitro and have the potential to generate every cell type in the organism.[5] iPSCs are generated by reprogramming somatic cells to a pluripotent state similar to ESCs, and are therefore patient-specific. In a specific example, embryonic stem cells or iPS cells are undifferentiated pluripotent stem cells, expressing OCT4, SOX2, NANOG, and SSEA4. Human pluripotent stem cells can be referred to as hPSCs.

The cell may be a stem cell. A stem cell may refer to a totipotent, pluripotent, multipotent, oligopotent or unipotent cell that can undergo self-renewing cell division to give rise to phenotypically and genotypically identical daughter cells for an indefinite time and can ultimately differentiate into at least one final cell type. The term "stem cell" is to be understood as meaning a cell that can be derived from any source of tissue or organ and can replicate as undifferentiated or lineage committed cells and have the potential to differentiate into at least one, preferably multiple, cell lineages.

Examples of stem cells include totipotent, pluripotent, multipotent, oligopotent and unipotent stem cells (e.g., progenitor cells). Examples of pluripotent stem cells include embryonic stem cells, embryonic germ cells, embryonic carcinoma cells, and induced pluripotent stem cells (iPSCs). Non-limiting examples of stem cells include embryonic stem cells, fetal stem cells, and adult (or somatic) stem cells. Stem cells can be obtained commercially, or obtained/isolated directly from patients, or from any other suitable source.

Undifferentiated or partially differentiated precursor cells may also be used, such as embryonic germ cells, mesenchymal stem cells, multipotent adult stem cells, etc.

In one embodiment, the stem cell is human.

Embryonal stem cell (ES) has unlimited self-renewal and multipotent and/or pluripotent differentiation potential, thus possessing the capability of developing into any organ, tissue type or cell type. These cells can be derived from the inner cell mass of the blastocyst, or can be derived from the primordial germ cells from a post-implantation embryo (embryonal germ cells or EG cells). Evans et al. (1981) Nature 292:154-156; Matsui et al. (1991) Nature 353:750-2; Thomson et al. (1995) Proc. Natl. Acad. Sci. USA. 92:7844-8; Thomson et al. (1998) Science 282:1145-1147; and Shamblott et al. (1998) Proc. Natl. Acad. Sci. USA 95:13726-31.

"Induced pluripotent stem cells," commonly abbreviated as iPS cells or iPSCs, refer to a type of pluripotent stem cell artificially prepared from a non-pluripotent cell, typically an adult somatic cell, or terminally differentiated cell, such as a fibroblast, a hematopoietic cell, a myocyte, a neuron, an epidermal cell, or the like, by introducing certain factors, referred to as reprogramming factors. In one aspect, the iPSC is derived from a fibroblast cell. The cell may be an induced pluripotent stem cell (iPSC), e.g., derived from a fibroblast of a subject.

For example, patient fibroblast cells can be collected from the skin biopsy and transformed into iPS cells. Dimos J T et al. (2008) Induced pluripotent stem cells generated from patients with ALS can be differentiated into motor neurons. Science 321: 1218-1221; Nature Reviews Neurology 4, 582-583 (November 2008). Luo et al., Generation of induced pluripotent stem cells from skin fibroblasts of a patient with olivopontocerebellar atrophy, Tohoku J. Exp. Med. 2012, 226(2): 151-9.

The cell may be autologous or allogeneic to the subject who is administered the cell. The term "autologous" refers to any material derived from the same individual to whom it is later to be re-introduced into the same individual.

The term "allogeneic" refers to any material derived from a different animal of the same species as the individual to whom the material is introduced. Two or more individuals of the same species are said to be allogeneic to one another.

As used herein, "anterior foregut endoderm" (AFE) refers to endoderm that is anterior to the endoderm that gives rise to the liver. Anterior foregut endoderm may include, for example, pharyngeal endoderm or lung endoderm and other, more highly differentiated populations of endodermal cells. As embryonic tissues express characteristic sets of molecular markers, the various cell types encompassed by the term "anterior foregut endoderm" may exhibit different expression patterns of molecular markers. One of ordinary skill in the art will appreciate that "anterior foregut endoderm" gives rise to various tissues, e.g., tonsils, tympanic membrane, thyroid, parathyroid glands, thymus, trachea, esophagus, stomach, lung and larynx/pharynx. Anterior foregut endoderm expresses FOXA2, FOXA1, SOX2 and EPCAM and is negative for the distal endoderm marker CDX2.

As used herein, definitive endoderm (DE) is one of the three germ layers arising after gastrulation that give rise to the intestinal tract, liver, pancreas, stomach and all other organs derived from the AFE, as listed above. DE expresses the markers: FOXA2, FOXA1, cKIT, CXCR4, and EPCAM.

Lung bud organoid(s) (LBO(s)) may be derived from pluripotent stem cells (e.g., human pluripotent stem cells) in suspension and contain lung epithelial (expressing FOXA2, FOXA1, NKX2.1 and EPCAM) and/or mesenchymal progenitors (expressing PDGFRa, CD90, TBX4, and HOXA5). Lung bud organoids may generate branching colonies after embedding in a 3D matrix (e.g., Matrigel). LBOs may be spheroids when generated from anterior foregut cells in suspension cultures in vitro. LBOs may form between d20-d25 (day 20 to day 25) and may include folding structures inside organoids.

The term "branched LBO" (BLBO) as used herein refers to LBOs that possess structures relating to branching morphogenesis. As the BLBOs further develop they begin to show dilated tips which have the morphology of fetal alveolar structures.

The term "matrigel sandwich" as used herein refers to an arrangement of Matrigel and LBOs that allows for 3-dimensional growth of LBOs into BLBOs. In one specific example, the arrangement involves a bottom portion of solidified Matrigel, a mixed Matrigel/LBO middle section, and a top portion of solidified Matrigel, thereby resembling a sandwich configuration.

Different Progenitor Types According to Differentiation Protocol:

1. Embryonic stem cells or iPS cells: undifferentiated.
2. Definitive endoderm: FOXA2+, cKIT+, CXCR4+, EPCAM+ (epithelial marker).
3. Anterior foregut endoderm: FOXA2+, SOX2+, EPCAM+, CDX2−.
4. Ventral anterior foregut endoderm or lung progenitors: FOXA2+, NKX2.1+, EPCAM+.
5. Lung bud organoids: organoids derived in suspension, also FOXA2+NKX2.1+EPCAM+ (WO/2018/176044).
6. The lung bud organoids may generate branching colonies after plating in a 3D matrix (e.g., Matrigel) (WO/2018/176044).
7. Cells which will be particularly useful for therapeutic applications are described in this section. From either lung bud organoids or Matrigel branching organoids, cells can be grown after dissociation in either condition A or condition B. Cells from condition A can also be switched to B at any time and they will assume the phenotype associated with condition B. These phenotypes include:
   Condition A: putative distal tip progenitors: NKX2.1 (dim), SOX2+, SOX9+; some cells at the edge of colonies express KRT5 (dim) and P63. For reference, these cells are referred to herein as "lung progenitor cells" or "pDTPs".
   Condition B: virtually all cells become KRT5+, P63+, ITGA6+, NGFR+. This is the phenotype of basal cells or lung/airway progenitors. For reference, these cells are referred to herein as "lung progenitor cells" or "basal cell-like" or "BC-like" or "putative submucosal gland progenitors" (pSMGPs).

As used herein, a "prophylactically effective" amount is an amount of a substance effective to prevent or to delay the onset of a given pathological condition in a subject to which the substance is to be administered. A prophylactically effective amount refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

As used herein, a "therapeutically effective" amount is an amount of a substance effective to treat, ameliorate or lessen a symptom or cause of a given pathological condition in a subject suffering therefrom to which the substance is to be administered.

"Treating" or "treatment" of a state, disorder or condition includes: (1) preventing or delaying the appearance of clinical symptoms of the state, disorder, or condition developing in a person who may be afflicted with or predisposed to the state, disorder or condition but does not yet experience or display clinical symptoms of the state, disorder or condition; or (2) inhibiting the state, disorder or condition, i.e., arresting, reducing or delaying the development of the disease or a relapse thereof (in case of maintenance treatment) or at least one clinical symptom, sign, or test, thereof; or (3) relieving the disease, i.e., causing regression of the state, disorder or condition or at least one of its clinical or sub-clinical symptoms or signs. "Treat" or "treating" means to administer a therapeutic agent, such as a composition containing any compound or therapeutic agent of the present invention, internally or externally to a subject or patient having one or more disease symptoms, or being suspected of having a disease or being at elevated at risk of acquiring a disease, for which the agent has therapeutic activity. Typically, the agent is administered in an amount effective to alleviate one or more disease symptoms in the treated subject or population, whether by inducing the regression of or inhibiting the progression of such symptom(s) by any clinically measurable degree. The amount of a therapeutic agent that is effective to alleviate any particular disease symptom (also referred to as the "therapeutically effective amount") may vary according to factors such as the disease state, age, and weight of the patient, and the ability of the drug to elicit a desired response in the subject. Whether a disease symptom has been alleviated can be assessed by any clinical measurement typically used by physicians or other skilled healthcare providers to assess the severity or progression status of that symptom.

The benefit to a subject to be treated is either statistically significant or at least perceptible to the patient or to the physician.

"Activation," "stimulation," and "treatment," as it applies to cells or to receptors, may have the same meaning, e.g., activation, stimulation, or treatment of a cell or receptor with a ligand, unless indicated otherwise by the context or explicitly. "Ligand" encompasses natural and synthetic ligands, e.g., cytokines, cytokine variants, analogues, muteins, and binding compounds derived from antibodies. "Ligand" also encompasses small molecules, e.g., peptide mimetics of cytokines and peptide mimetics of antibodies. "Activation" can refer to cell activation as regulated by internal mechanisms as well as by external or environmental factors. "Response," e.g., of a cell, tissue, organ, or organism, encompasses a change in biochemical or physiological behavior, e.g., concentration, density, adhesion, or migration within a biological compartment, rate of gene expression, or state of differentiation, where the change is correlated with activation, stimulation, or treatment, or with internal mechanisms such as genetic programming.

"Activity" of a molecule may describe or refer to the binding of the molecule to a ligand or to a receptor, to catalytic activity; to the ability to stimulate gene expression or cell signaling, differentiation, or maturation; to antigenic activity, to the modulation of activities of other molecules, and the like. "Activity" of a molecule may also refer to activity in modulating or maintaining cell-to-cell interactions, e.g., adhesion, or activity in maintaining a structure of a cell, e.g., cell membranes or cytoskeleton. "Activity" can also mean specific activity, e.g., [catalytic activity]/[mg protein], or [immunological activity]/[mg protein], concentration in a biological compartment, or the like. "Activity" may refer to modulation of components of the innate or the adaptive immune systems.

"Administration" and "treatment," as it applies to an animal, human, experimental subject, cell, tissue, organ, or biological fluid, refers to contact of an exogenous pharmaceutical, therapeutic, diagnostic agent, or composition to the animal, human, subject, cell, tissue, organ, or biological fluid. "Administration" and "treatment" can refer, e.g., to therapeutic, pharmacokinetic, diagnostic, research, and experimental methods. Treatment of a cell encompasses contact of a reagent to the cell, as well as contact of a reagent to a fluid, where the fluid is in contact with the cell. "Administration" and "treatment" also means in vitro and ex vivo treatments, e.g., of a cell, by a reagent, diagnostic, binding compound, or by another cell.

The term "subject" includes any organism, preferably an animal, more preferably a mammal (e.g., rat, mouse, dog, cat, rabbit) and most preferably a human. Subjects, which may be treated according to the present disclosure, include all animals which may benefit from the present invention. Such subjects include mammals, preferably humans (infants, children, adolescents and/or adults), but can also be an animal such as dogs and cats, farm animals such as cows, pigs, sheep, horses, goats and the like, and laboratory animals (e.g., rats, mice, guinea pigs, and the like).

In one embodiment, the present composition is administered to a subject in accordance with the Physicians' Desk Reference 2003 (Thomson Healthcare; 57th edition (Nov. 1, 2002)).

Acceptable excipients, diluents, and carriers for therapeutic use are well known in the pharmaceutical art, and are described, for example, in Remington: The Science and Practice of Pharmacy. Lippincott Williams & Wilkins (A. R. Gennaro edit. 2005). The choice of pharmaceutical excipient, diluent, and carrier can be selected with regard to the intended route of administration and standard pharmaceutical practice.

As used herein, the phrase "pharmaceutically acceptable" refers to molecular entities and compositions that are "generally regarded as safe", e.g., that are physiologically tolerable and do not typically produce an allergic or similar untoward reaction, such as gastric upset, dizziness and the like, when administered to a human. Preferably, as used herein, the term "pharmaceutically acceptable" means approved by a regulatory agency of the Federal or a state government or listed in the U.S. Pharmacopoeia or other generally recognized pharmacopeias for use in animals, and more particularly in humans.

"Patient" or "subject" refers to mammals and includes human and veterinary subjects. Certain veterinary subjects may include avian species.

Kits

The present disclosure also provides kits comprising the present compositions, components, or combinations thereof in kit form. A kit may include one or more components including, but not limited to, any of the therapeutic compositions or screening or models of basal-like cell or putative distal tip progenitor lines, as discussed herein, optionally in association with one or more additional components including, a therapeutic agent, as discussed herein. The compositions and/or the therapeutic agent(s) can be formulated as a pure composition or in combination with a pharmaceutically acceptable carrier, in a pharmaceutical composition.

In one embodiment, a kit includes any of the therapeutic compositions or screening or models of basal-like cell or putative distal tip progenitor lines, each in a separate container (e.g., in a sterile glass or plastic vial). The kit can include a package insert including information concerning cell growth and maintenance, as well as buffers and/or growth factors in the kit.

To prepare pharmaceutical or sterile compositions of the compositions of the present invention, the compounds or cells, or similar compositions may be admixed with a pharmaceutically acceptable carrier or excipient. See, e.g., Remington's Pharmaceutical Sciences and U.S. Pharmacopeia: National Formulary, Mack Publishing Company, Easton, Pa. (1984).

Formulations of therapeutic and diagnostic agents may be prepared by mixing with acceptable carriers, excipients, or stabilizers in the form of, e.g., lyophilized powders, slurries, aqueous solutions or suspensions (see, e.g., Hardman, et al. (2001) Goodman and Gilman's The Pharmacological Basis of Therapeutics, McGraw-Hill, New York, N.Y.; Gennaro (2000) Remington: The Science and Practice of Pharmacy, Lippincott, Williams, and Wilkins, New York, N.Y.; Avis, et al. (eds.) (1993) Pharmaceutical Dosage Forms: Parenteral Medications, Marcel Dekker, NY; Lieberman, et al. (eds.) (1990) Pharmaceutical Dosage Forms: Tablets, Marcel Dekker, NY; Lieberman, et al. (eds.) (1990) Pharmaceutical Dosage Forms: Disperse Systems, Marcel Dekker, NY; Weiner and Kotkoskie (2000) Excipient Toxicity and Safety, Marcel Dekker, Inc., New York, N.Y.).

A "transplantable graft" refers to a biological material, such as cells, tissues and organs (in whole or in part) that can be administered to a subject. Transplantable grafts may be autografts, allografts, or xenografts of, for example, a biological material such as an organ, tissue, skin, bone, nerves, tendon, neurons, blood vessels, fat, cornea, pluripotent cells, differentiated cells or progenitor or stem cells cell populations (obtained or derived in vivo or in vitro), etc. In some embodiments, a transplantable graft is formed, for example, from cartilage, bone, extracellular matrix, or collagen matrices. Transplantable grafts may also be single cells, suspensions of cells and cells in tissues and organs that can be transplanted. Transplantable cells typically have a therapeutic function, for example, a function that is lacking or diminished in a recipient subject. Some non-limiting examples of transplantable cells are lung progenitor cells or basal-like cells capable of differentiating into lung airway cells. Transplantable cells can be cells that are unmodified, for example, cells obtained from a donor subject and usable in transplantation without any genetic or epigenetic modifications. In other embodiments, transplantable cells can be modified cells, for example, cells obtained from a subject having a genetic defect, in which the genetic defect has been corrected, or cells that are derived from reprogrammed cells, for example, differentiated cells derived from cells obtained from a subject.

"Transplantation" refers to the process of transferring (moving) a transplantable graft into a recipient subject (e.g., from a donor subject, from an in vitro source (e.g., differentiated autologous or heterologous native or induced pluripotent cells)) and/or from one bodily location to another bodily location in the same subject.

In an embodiment, the transplanted tissue is lung tissue. In an embodiment, the transplanted tissue is transplanted as a composition of "basal-like cells or lung progenitor cells".

The term "allogeneic" refers to any material derived from a different animal of the same species as the individual to whom the material is introduced. Two or more individuals are said to be allogeneic to one another when the genes at one or more loci are not identical.

The term "autologous" refers to any material derived from the same individual to whom it is later to be re-introduced into the same individual.

Standard methods in molecular biology are described Sambrook, Fritsch and Maniatis (1982 & 1989 2$^{nd}$ Edition, 2001 3$^{rd}$ Edition) Molecular Cloning, A Laboratory Manual, Cold Spring Harbor Laboratory Press, Cold Spring Harbor, N.Y.; Sambrook and Russell (2001) Molecular Cloning, 3$^{rd}$ ed., Cold Spring Harbor Laboratory Press, Cold Spring Harbor, N.Y.; Wu (1993) Recombinant DNA, Vol. 217, Academic Press, San Diego, Calif.). Standard methods also appear in Ausbel, et al. (2001) Current Protocols in Molecular Biology, Vols. 1-4, John Wiley and Sons, Inc. New York, N.Y., which describes cloning in bacterial cells and DNA mutagenesis (Vol. 1), cloning in mammalian cells and yeast (Vol. 2), glycoconjugates and protein expression (Vol. 3), and bioinformatics (Vol. 4).

Methods for protein purification including immunoprecipitation, chromatography, electrophoresis, centrifugation, and crystallization are described (Coligan, et al. (2000) Current Protocols in Protein Science, Vol. 1, John Wiley and Sons, Inc., New York). Chemical analysis, chemical modification, post-translational modification, production of fusion proteins, glycosylation of proteins are described (see, e.g., Coligan, et al. (2000) Current Protocols in Protein Science, Vol. 2, John Wiley and Sons, Inc., New York; Ausubel, et al. (2001) Current Protocols in Molecular Biology, Vol. 3, John Wiley and Sons, Inc., NY, NY, pp. 16.0.5-16.22.17; Sigma-Aldrich, Co. (2001) Products for Life Science Research, St. Louis, Mo.; pp. 45-89; Amersham Pharmacia Biotech (2001) BioDirectory, Piscataway, N.J., pp. 384-391). Production, purification, and fragmentation of polyclonal and monoclonal antibodies are described (Coligan, et al. (2001) Current Protocols in Immunology, Vol. 1, John Wiley and Sons, Inc., New York; Harlow and Lane (1999) Using Antibodies, Cold Spring Harbor Laboratory Press, Cold Spring Harbor, N.Y.; Harlow and Lane, supra). Standard techniques for characterizing ligand/receptor interactions are available (see, e.g., Coligan, et al. (2001) Current Protocols in Immunology, Vol. 4, John Wiley, Inc., New York).

Ex Vivo Expansion of Airway Progenitors

The present lung progenitor cells may be used for cellular replacement therapy for airway diseases as described herein (e.g., CF). The present lung progenitor cells may be propagated in vitro. Cells consistent with a BC phenotype could be expanded, e.g., using a specially formulated culture medium (such as Bronchial Epithelial Growth Medium, or BEGM). Previously, expansion was limited, and senescence typically ensued after a few passages. Generating sufficient numbers of functional cells for regenerative purposes was therefore previously impossible. McMullan et al. reported that inhibition of Rho kinase (ROCK) enhanced proliferation and prevented differentiation of keratinocytes. ROCK is a target of RhoA, a GTPase involved in regulation cell adhesion and actomyosin cytoskeleton dynamics.[79] Subsequently it was shown that culture on 3T3-J2 feeders in the presence of a small molecule ROCK inhibitor (Y-27632) led to stable expansion of human foreskin, ectocervix and vaginal keratinocytes[80], mammary and prostate epithelial cells, epithelial tumors,[81] human intestinal stem cells in adherent cultures[82], finally also in human BCs[83]. Similar to what was observed in other epithelia, senescence did not occur, the cells largely maintained a basal cell phenotype, and activated telomerase expression. The karyotype of the cells remained normal, while no evidence for increased copy number variation was observed, indicative of their genomic stability. Importantly, the cells were functional, as even late-passage cells could generate tracheospheres[61] containing mucus and ciliated cells, and formed ciliated cells in air-liquid interphase cultures. It has been shown that dual SMAD inhibition allowed extensive expansion in the absence of feeder, but did document critical telomere shortening[84].

Engraftment of Airway Progenitors

Engraftment of cells in lung and airway may need injury that at least partially eliminates resident epithelial cells and their progenitors. Different types of injury target different regions of lung. There are several approaches that may be used to induce injury. Bleomycin causes predominantly distal injury, and may also be used for assessing capacity to engraft proximally. Similarly, hyperoxia causes loss of alveolar and endothelial cells[101-113]. For airway injury, exposure to toxic gases ($SO_2$ or chlorine), which kills most luminal cells and reliably induces airway injury and regeneration by BCs,[61,84,114] and naphthalene, which selectively kills club cells, are most often used[58,61,115-119]. The DSCs identified by Zuo et al. and Vaughan et al.[69,79] are capable of contributing to repair of influenza-injured mouse lungs and differentiating into ATI, ATII, and secretory cells. In the Vaughan paper[69], engraftment was accomplished after intranasal administration. The mouse DTPs isolated by Nichane et al. could engraft with efficiency in bleomycin-treated mice.

In one embodiment, a xenogeneic model, the Nod.Scid.il2rg$^{-/-}$ (NSG) mouse, is uded. Engraftment of human cells in lungs of NSG mice is little explored. Nikolic et al[92] could achieve engraftment of bleomycin-treated NSG mice with expanded putative human fetal lung distal tip cells, but only followed up until 8 days and did not monitor differentiation. Rosen et al. used naphthalene combined with irradiation to engraft canalicular stage fetal lung cells in NSG mice through IV transfer[121]. Furthermore, although naphthalene only affects club cells, they observed engraftment of proximal and distal cells, as well as mesenchymal and endothelial cells. Finally, the Spence group reported the generation of DTPs from organoids reminiscent of our published lung bud organoids, that showed some engraftment potential in naphthalene-treated NSG mice.

The following examples of specific aspects for carrying out the present invention are offered for illustrative purposes only and are not intended to limit the scope of the present invention in any way.

Example 1 Generation of a Population Containing Putative Distal Tip Progenitors (pDTPs)

Figure 2C:
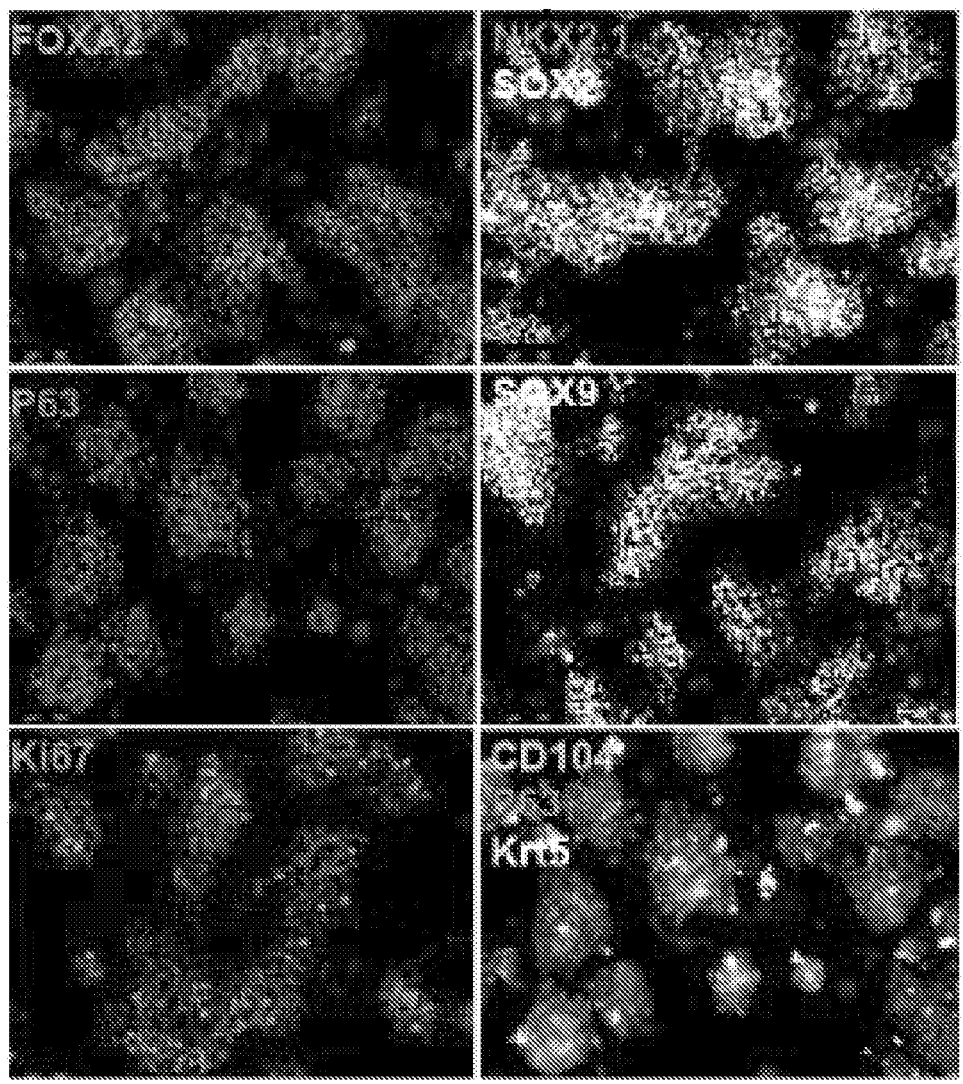

LBOs contained sporadic cells that expressed p63, but not KRT5, and might be similar to the early, multipotential (i.e., contributing to both proximal and distal lung) p63$^+$ progenitors identified by Yang et al. in mouse lung buds. Furthermore, during the Matrigel stage of these cultures, we identified SOX9$^+$ cells in the tips, while p63$^+$ were detectable but rare. We therefore explored whether cells in these organoids could be expanded as a continuous progenitor line corresponding to p63$^+$ progenitors or to DTPs[88,91,92,133]. Organoids at various stages of development were dissociated and cultured under a variety of conditions. In the presence of 3T3-J2 feeder cells, the GSK3 inhibitor, CHIR, FGF7, FGF10, BMP4, retinoic acid, and Rock inhibitor Y27632; (condition A, FIG. 2B), rapidly proliferating cells formed colonies expressing SOX2, SOX9 and low amounts of NKX2.1, with predominantly the centers of colonies staining for the proliferation marker Ki67 (FIG. 2C). Markers for mature lung or airway cells were not expressed. The phenotype of these cells may correspond to DTP in human fetal lung[92]. Cells at the periphery of the colonies proliferated less and expressed P63, while KRT5 was absent or lowly expressed. These data may suggest spontaneous differentiation from one population into the other, but could also indicate that these culture conditions support both early lung bud p63$^+$ and later SOX2±SOX9$^+$ distal progenitors. Both possibilities are furthermore not mutually exclusive. The cells have now been generated from one ES line and two iPS lines, passaged for 18 months, frozen and thawed. Similar cells were generated from developing organoids at any time between day 20 and day 180, and between day 25 and day 150. Cultures however were clearly heterogeneous. We will therefore refer to these cells for now as Condition A cells.

Culture and expansion of native DTPs has been reported using culture conditions that differ from presently described conditions[92,98,99]. Nichane et al.[99] used screen with cells isolated from mouse fetal lungs based on expression of a distal Sox reported to identify heparin, Fgf9, Fgf9, EGF, TGF-β inhibition (TGFbi), GSK3- and MAPKi in Matrigel, where cells could be passaged for 6 months. They reported that each of these factors was essential. They furthermore reported a 'community' effect, ie, cells could not be grown as single cells. Nicholic et al. dissected distal tips from early stage fetal lungs and could obtain limited expansion of the cells in the presence of EGF, FGF7, FGF9, TGFbi, GSK3i, Noggin and Rspondin (Rspo), also in Matrigel. Some cultures have reportedly been maintained for 9 months, but it is unclear to what extent function, gene expression and morphology were maintained. Nicholic et al grew and passaged their cells as clumps, not as single cell suspension. Miller et al. used isolated mouse distal tip cultures to identify conditions that maintained distal tip progenitors in vitro and tested this identified condition in maintaining isolated human fetal and hPSC-derived distal tip progenitors. They found that FGF7, CHIR, and RA are required to maintain the cultures. The hPSC-derived distal tip cultures were also maintained in Matrigel, required the presence of fetal bovine serum and passaged by mechanical shearing through a needle as clumps. They reported that the hPSC-derived bud tip-like cells survived in vitro for over 16 weeks, but that spontaneous differentiation occurs.

Commonalities with embodiments of present culture conditions are the use of GSK3i (CHIR) and FGFs. In contrast to previous methods, BMP4 (rather than Noggin, which is BMP inhibitor), as well as RI and RA were utilized in the present methods to obtain/generate the lung progenitor cells. Furthermore, while these conditions required MEF feeders, both other reports use Matrigel, or sometimes fetal bovine serum. The presently described approach is unique and these cells can be expanded as far as we can see now, indefinitely, as they are derived from hPSCS and can therefore be genetically corrected using CRISPR/Cas9, and as they can engraft in the lungs of immunodeficient mice (see below). These features and conditions have never been accomplished before.

Figure 2D:
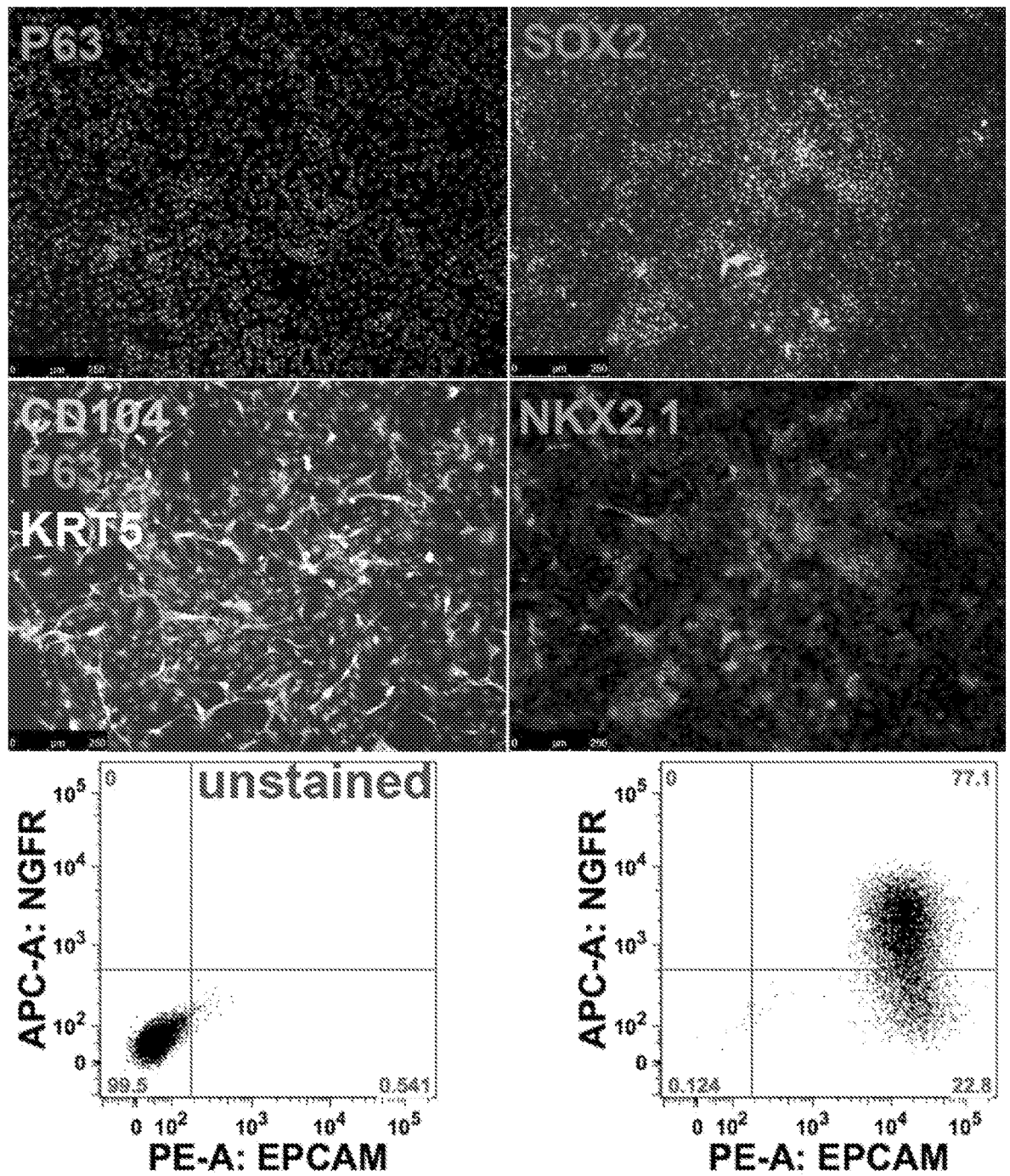

Example 2 Generation of Basal Cell-Like Cells (Lung Progenitors) from Condition a Cells When transferred to J2 feeders in the presence of EGF and RI (condition B, FIG. 2B), most cells began to express BC markers KRT5, ITGA6, P63 (FIG. 2D). A majority of the cells (>90%) also expressed NGFR after several passages (FIG. 2D). This is of particular interest, as NGFR is only expressed on postnatal BCs[61,125]. These BC-like cells cannot be maintained indefinitely, since their expansion begins to slow down after several passages. BC-like cells from condition B could not be maintained in condition A, indicating that condition B is not permissive for pDTPs.

Functional Studies
1. Air-Liquid Interphase Culture.

Figures 3A, 3B, 3C:
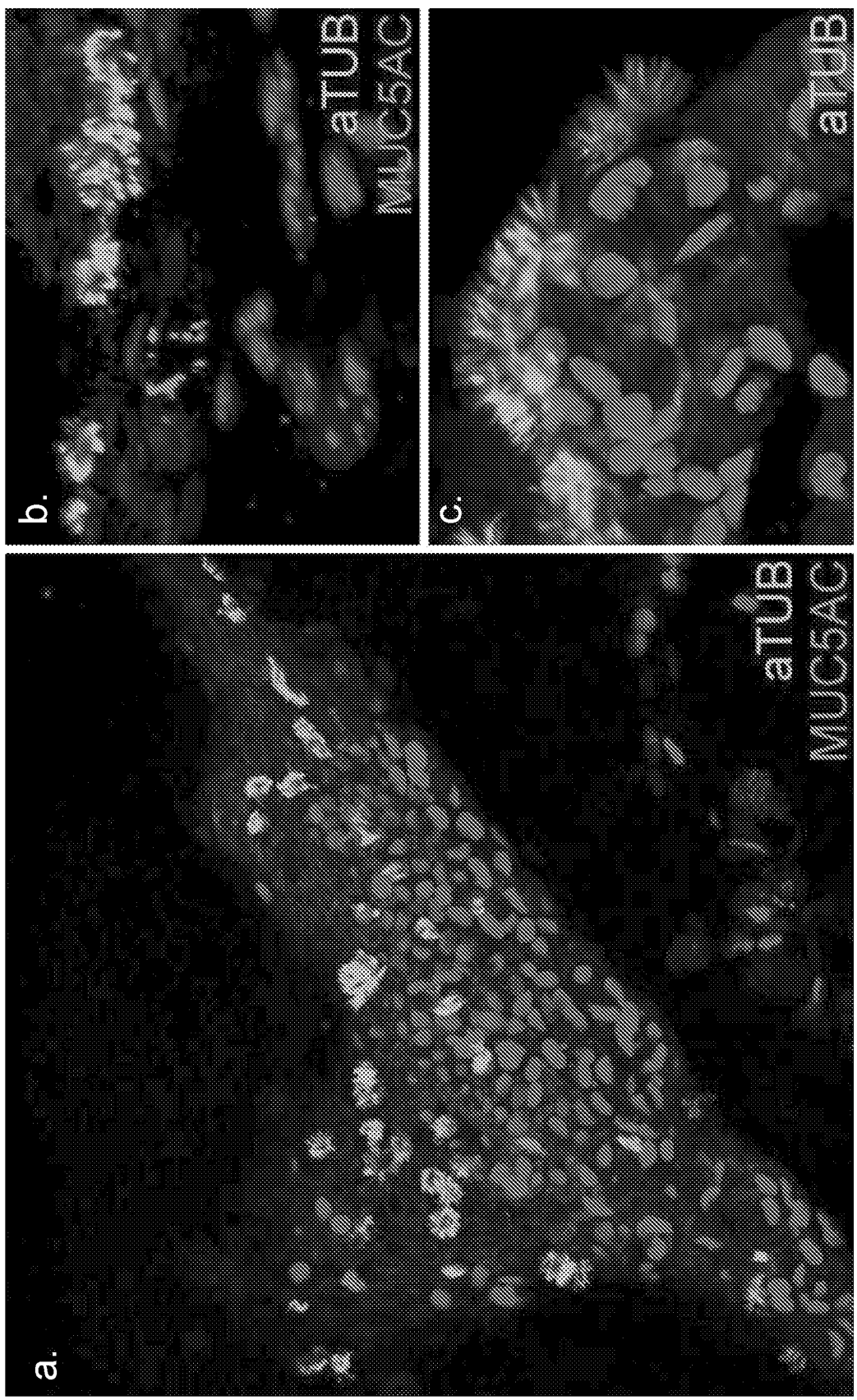
FIGS. 3A-3C are images of air liquid interphase cultures. Immunofluorescent staining of condition B, BC-like cells after 2 months of air-liquid interface cultures (FIGS. 3A-C).

To study airway potential, we performed air-liquid interphase (ALI) cultures. BC-like cells grew to confluence in condition B, and showed generation of ciliated and goblet cells, defining these cells as airway progenitors or BCs (FIG. 3A). Condition A cells never reached confluence, however, and did not express any airway markers (not shown).

2. Decellularized Trachea

Figures 4A, 4B, 4C:
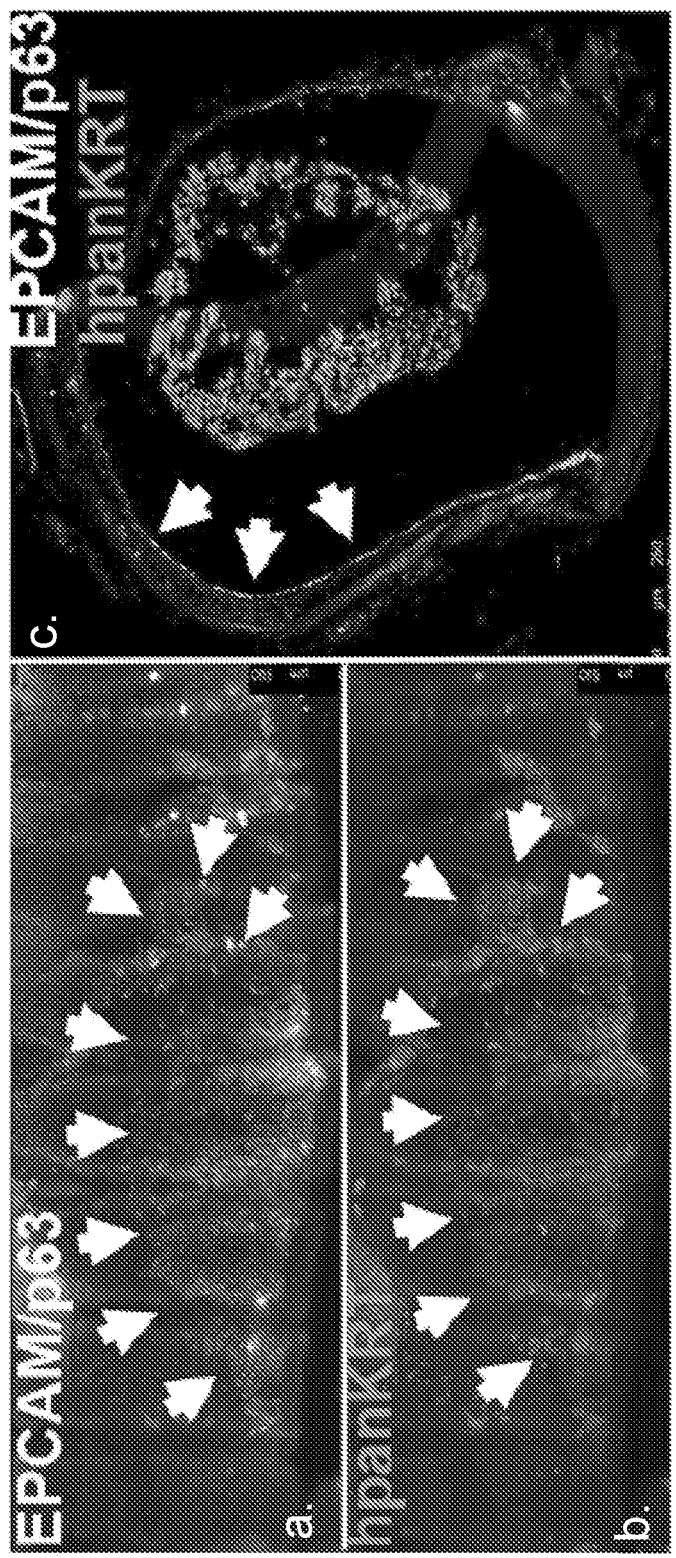
FIG. 4A-4C are images of engraftment of condition B, BC-like cells in de-epithelialized mouse tracheas ex vivo. Epithelial cells were removed by trypsin from immunodeficient mouse tracheas. Condition B cells were seeded onto the de-epithelialized tracheas. The tracheas were fixed 7 days post seeding and stained for human pan-keratin (hPanK FIG. 4B-C), P63, and human EPCAM (hEPCAM) (FIGS. 4A and C). Arrows mark the areas with human cell engraftment (FIG. 4A-C).

To further examine the potential of BC-like cells for regeneration of airway epithelium, we seeded the condition B cells on decellularized mouse tracheas from NSG mice embedded in agarose. One million condition B cells were incubated overnight. The trachea was washed the next day to remove unattached cells, and incubated in condition B media ex vivo for 7 days before analysis. Substantial engraftment with human cells (identified by human pankeratin, human EPCAM and human p63 antibodies) was observed (FIGS. 4A-4C). Longer incubation is now evaluated.

3. Rat Lung Bioreactor

Figures 5A, 5B, 5C:
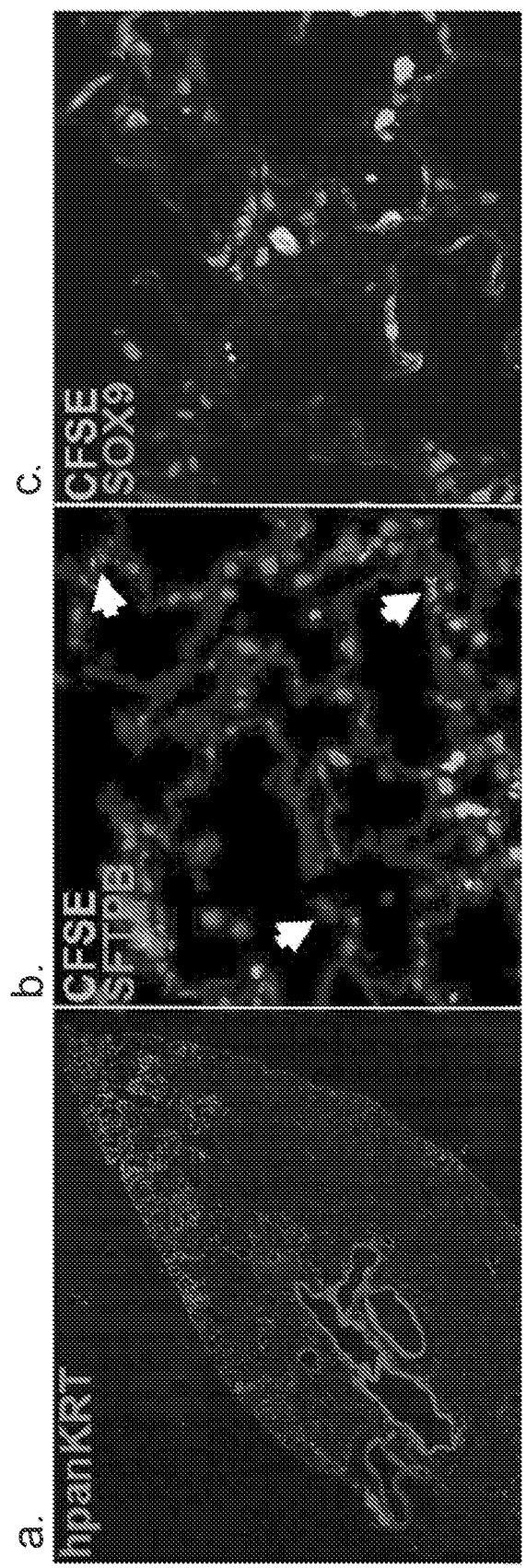
FIGS. 5A-5C are images showing attachment in rat lungs ex vivo. Epithelial cells were removed by detergent from lungs of nude rats. Condition A cells labeled with CFSE were transplanted intratracheally. The lungs were fixed 48 hours post transplantation, sectioned, and stained for human pankeratin (hpanKRT, FIG. 5A), SFTPB (FIG. 5B) and SOX9 (FIG. 5C).

We next seeded condition A cells in rat lung bioreactors. In this system, epithelium was removed as published by our group[8], a strategy that preserves the vasculature. $10^6$ pDTPs were instilled intratracheally, and rat lung was ventilated and perfused in a bioreactor. Human cells were identified by combined staining for human nuclei, human MHC class-I and human pankeratin (hpanKRT) (FIG. 5A), none of which stained host cells. Cell engraftment and flattening in the alveolar spaces, and co-expression of rare CFSE-labeled cells with markers of differentiation (SFTPB) were evident (FIG. 5B). SOX9 was mostly maintained on the engrafted cells. As SOX9 is downregulation during distal differentiation (FIG. 5C), these finding indicate very limited differentiation in this relatively short-term assays.

4. Bleomycin-Injured Lung of NSG Mice.

Figures 6A, 6B, 6C, 6D, 6E, 6F, 6G, 6H, 6I, 6J, 6K, 6L, 6M:
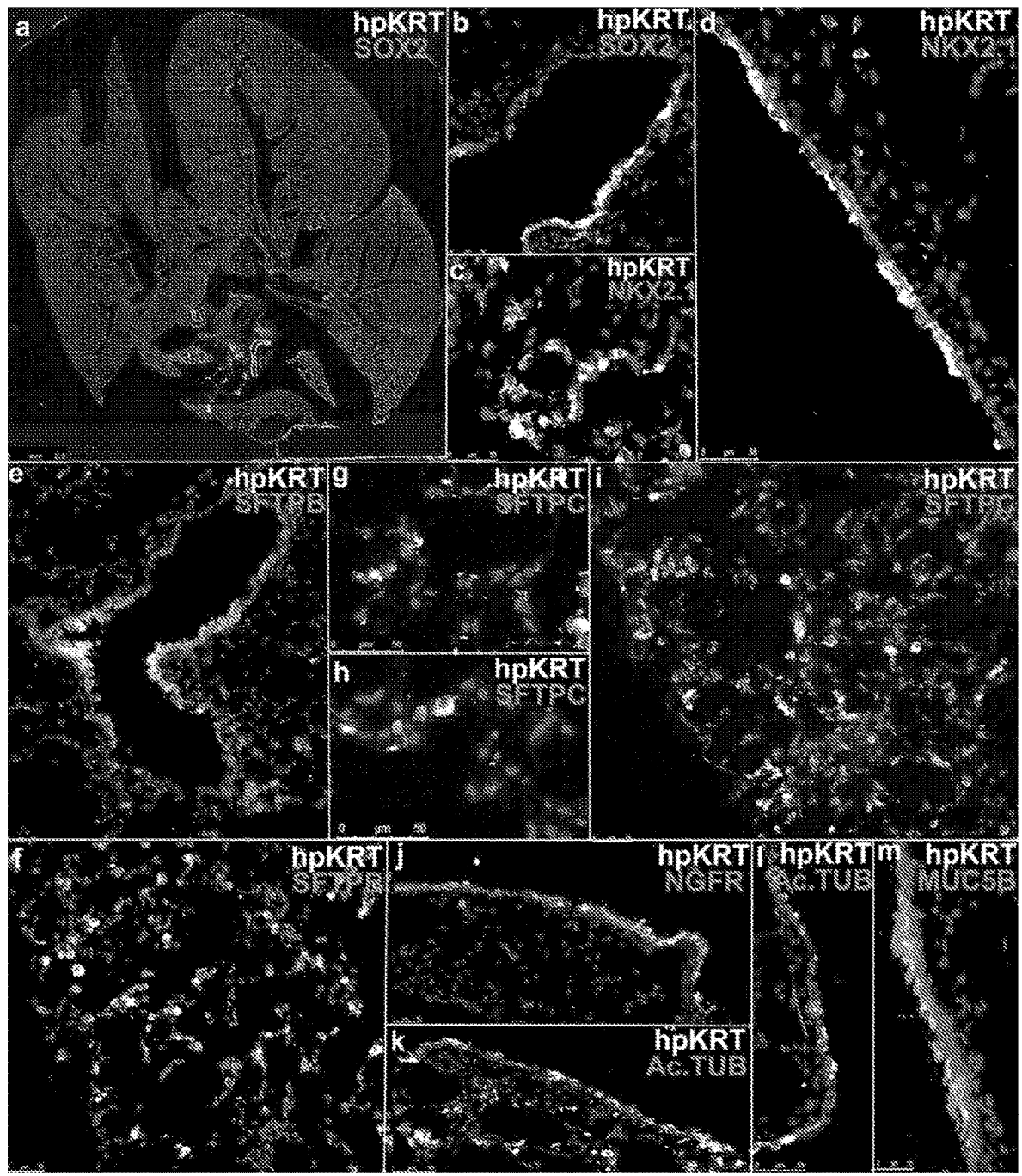
FIGS. 6A-6M are images showing engraftment of condition A (pDTP) cells in bleomycin-injured lungs of NSG mice in vivo. Lungs of NSG mice were injured by bleomycin. $10^6$ condition A cells were transplanted intranasally one day post-injury. Lungs were harvested, sectioned and stained for indicated markers after 3 weeks. Extensive presence of cell expressing human pankeratin was (hpKRT) detected, in particular in the periphery of the lungs (FIG. 6A). A variety of differentiation markers were observed to be co-expressed with hpanKRT, including SOX2 (airway, FIG. 6B), the lung marker NKX2.1 in alveoli (FIG. 6C) and airway (FIG. 6D), SFTPB (in airway club cells (FIG. 6E) and ATII cells (FIG. 6F)), SFTPC (ATII cells, FIG. 6G-I), NGFR (BCs, FIG. 6J), Ac.TUB (ciliated cells, FIGS. 6K-L), MUC5B (goblet cells, FIG. 6M). The grafted cells appeared morphologically well integrated in the epithelium.
Figure 7:
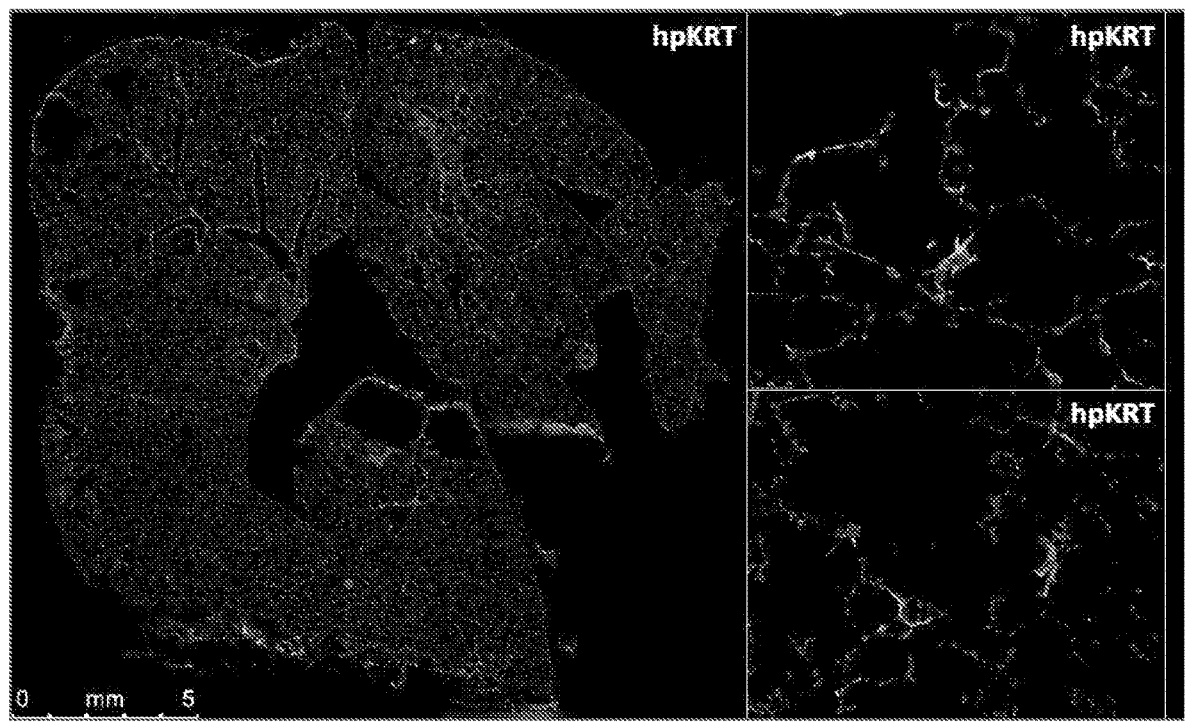
FIG. 7. Presence of hpKRT+ (white) cells in the lungs of NSG mice 6 months after treatment with bleomycin followed one day later by intranasal instillation of condition A (pDTP) cells.

Bleomycin causes widespread, predominantly distal injury. $10^6$ condition A or condition B cells were instilled intranasally in mice treated with 1.5 U/kg bleomycin 2 days prior. 3 weeks after administration of condition A cells, extensive presence of cell expressing human pankeratin (hpanKRT) was detected, in particular in the periphery of the lungs (FIG. 6A). A variety of differentiation markers were observed to be co-expressed with hpanKRT, including SOX2 (airway, FIG. 6B), the lung marker NKX2.1 in alveoli (FIG. 6C) and airway (FIG. 6D), SFTPB (in airway club cells (FIG. 6E) and ATII cells (FIG. 6F)), SFTPC (ATII CELLS, FIGS. 6G-I), NGFR (BCs, FIG. 6J), Ac.TUB (ciliated cells, FIGS. 6K-L), MUC5B (goblet cells, FIG. 6M). The grafted cells appeared morphologically well integrated in the epithelium. 6 months post-transplantation, human cells were still detectable (FIG. 7).

Figure 8:
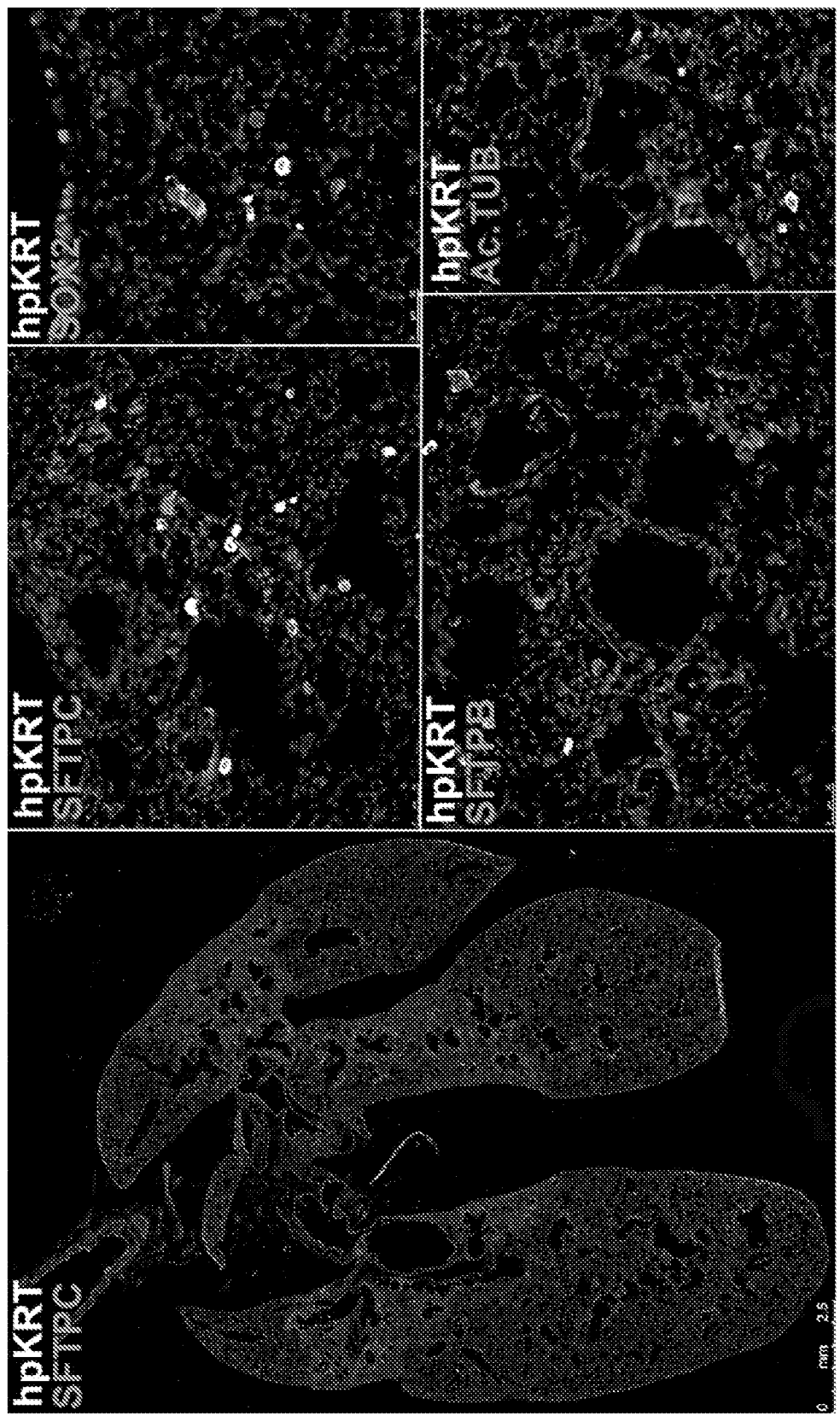
FIG. 8 includes images showing engraftment of condition B (BC-like) cells in bleomycin-injured lungs of NSG mice in vivo. Lungs of NSG mice were injured by bleomycin. $10^6$ condition B cells were transplanted intranasally one day post-injury. Lungs were harvested, sectioned and stained for indicated markers after 3 weeks. Sporadic cells were detected that were striking by their larger size, but they did not integrate in the epithelium and appeared to reside in air spaces. They did not express any differentiation markers. SOX2, which was already expressed by the cells, was detected.
Figures 9A, 9B, 9C:
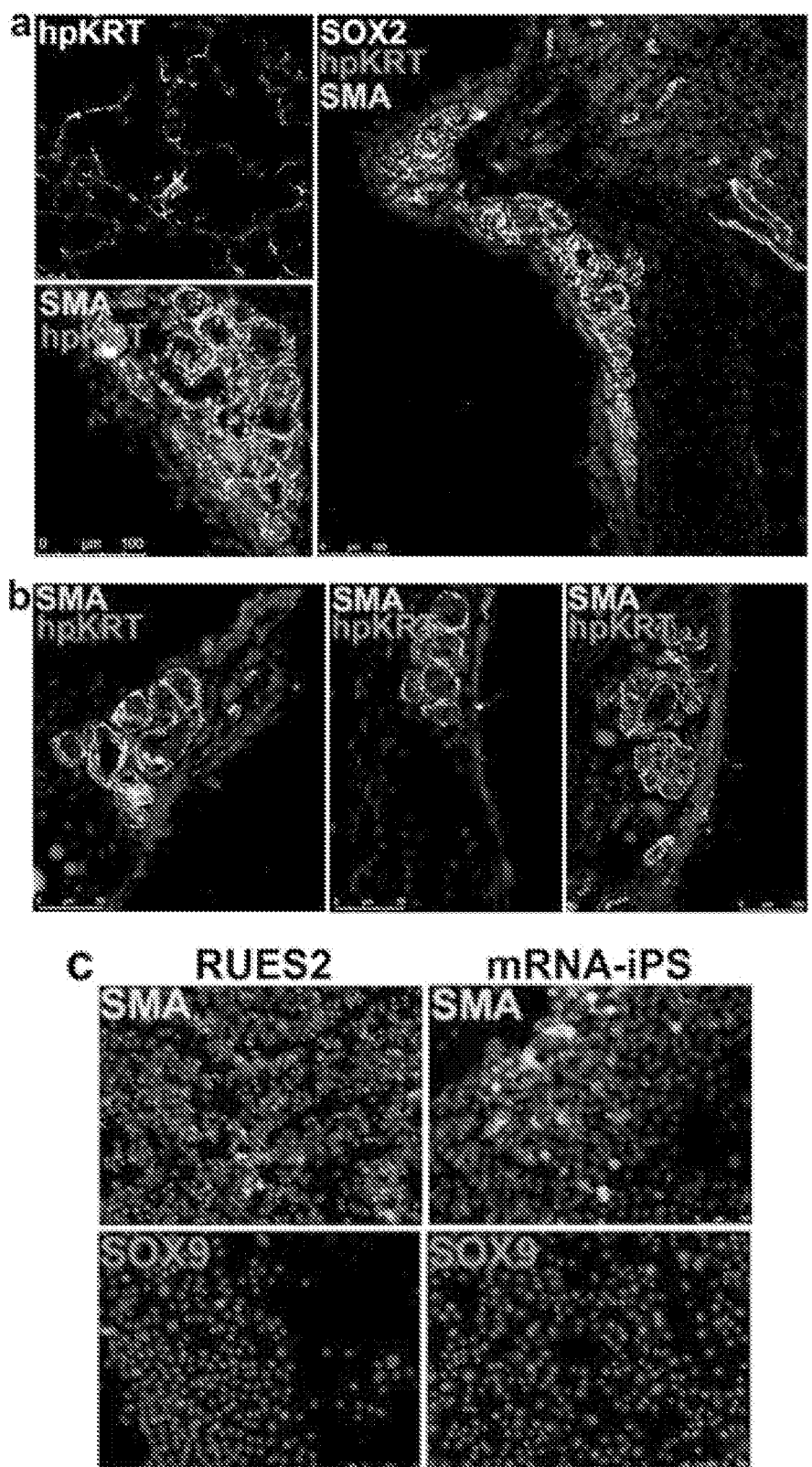
FIGS. 9A-9C. Engraftment of SMGs.

Condition B, BC-like cells, however, did not appreciably engraft in the short-term (3 weeks) (FIG. 8). Sporadic cells were detected that were striking by their larger size, but they did not integrate in the epithelium and appeared to reside in air spaces. They did not express any differentiation markers. SOX2, which was already expressed by the cells, was detected. Surprisingly, human cells were detected in the submucosal glands of the trachea 6 months post transplantation (FIGS. 9a-9c). Human cells could be seen extending into the epithelium of the trachea surrounding the engrafted submucosal glands (FIG. 9a, 9b). The cells in the submucosal glands expressed hpanKRT, αSMA and SOX2 and phenotypically and structurally resembled to submucosal gland myoepithelial cells in mice[1,2]. Furthermore, durable repopulation of submucosal glands was also found after transplantation of condition A cells. As these in vivo engraftment data suggested that at least some of the condition B cells have the potential to replace submucosal gland (SMG) myoepithelial cells and since that appear to be their only potential in vivo, we revisited their expression profiles by IF. IF revealed, in addition to p63, SOX2 and NGFR, expression of varying levels of SOX9 and SMA in a large fraction of the cells, derived from both RUES2 ESCs and iPSCs (FIG. 9c). The cells, or least a large fraction thereof, therefore have a phenotype consistent with that of SMG myoepithelial cells, a finding consistent with their capacity to engraft into SMGs. This is of major interest as submucosal myoepithelial cells have recently been shown to replenish the airway BC compartment after severe injury[2,3]. With respect to cellular therapy for CF, the prospect of replacing endogenous submucosal gland myoepithelial cells with genetically corrected cells would be very exciting, in particular since SMGs, which in humans are present throughout the cartilaginous airways have been suggested to play a major role in CF pathogenesis[4,5].

Summary

From hPSC-derived lung organoids, a population of cells could be generated and expanded that expresses the DTP markers, SOX2 and SOX9, and has the potential to remarkably efficiently provide multilineage engraftment in bleomycin injured lungs. This population was heterogeneous, as it also contained a subset of p63+ cells. The exact nature of the engrafting cells remains to be determined. Further research will have to indicate whether both populations possess equal or distinct engraftment and differentiation capacity. Modifications of the culture conditions need to be explored as well, in particular with the goal of growing the cells in feeder and/or Matrigel-independent fashion.

Figure 10:
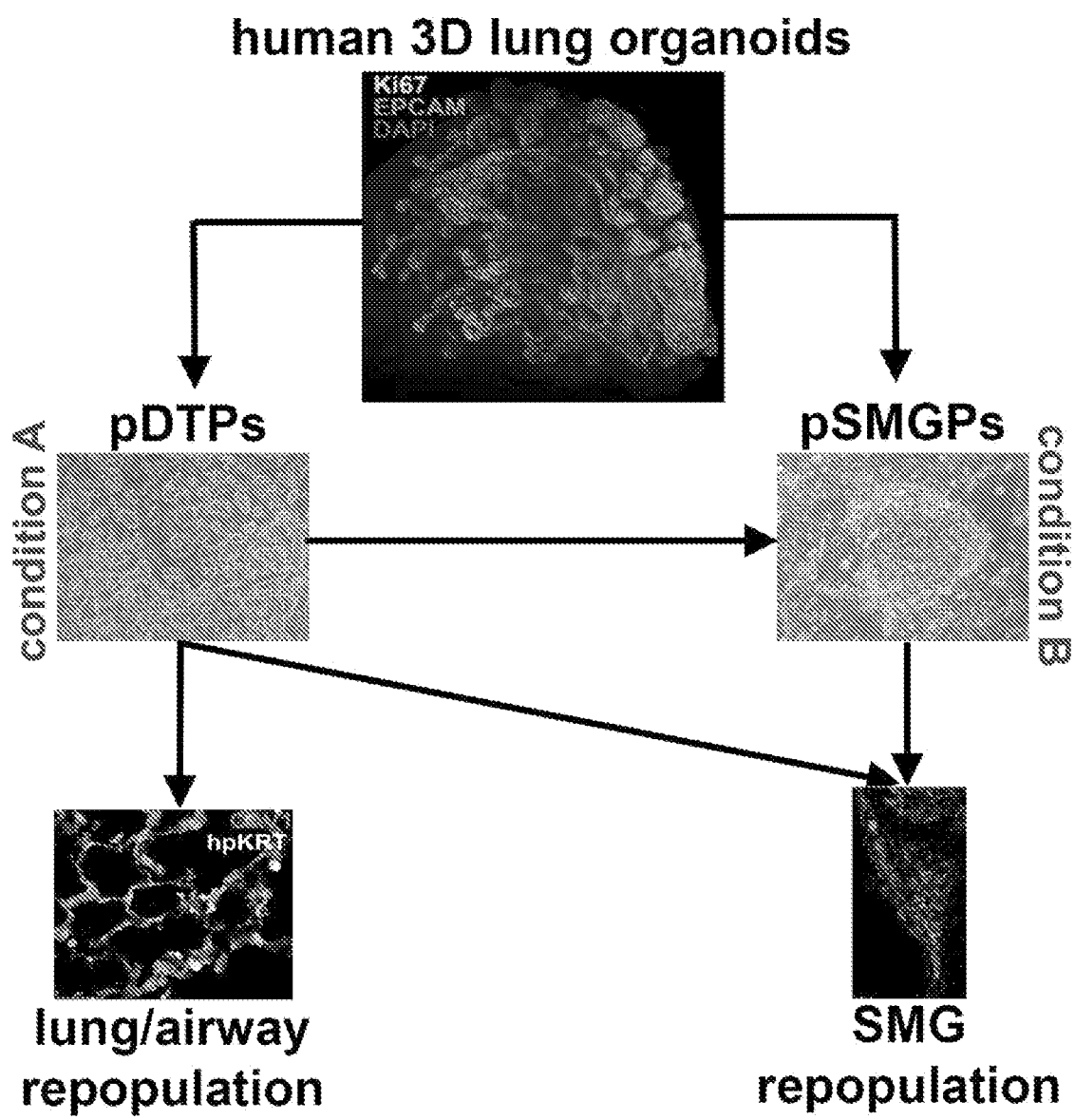
FIG. 10. Schematic overview of the derivation of the progenitor types generated from hPSC-derived lung organoids (e.g., condition A and condition B cells), and their in vivo potentials. pDTPs: putative distal tip progenitors. pSMGPs: putative submucosal gland progenitors.

From this putative pDTP population, a population of cells with the predominant phenotype of SMG myoepithelial cells, precursors of BCs that share several markers, such as KRT5, NGFR and P63 with BCs, could be derived. While these generated airway cells in ALI cultures, they could not efficiently engraft in the short-term. However, at later time points, both condition A and condition B cells repopulated SMGs. Thus, under certain scenarios, condition A cells may be the population of choice for regenerative medicine. It is however possible that in other injury models, the condition B cells may show engraftment as well. The condition A cells are the first cell population derived from hPSCs that can be expanded continuously, and is capable of efficient multilineage reconstitution of injured lungs (FIG. 10).

Methods

For condition A cells:
0. Lung bud organoids were generated based on previous protocol and dissociated at day 25, day 50, day 100, and day 150 by dispase.
1. The dissociated single/small clump cells were seeded on irradiated feeder cells (3T3-J2, feeder density >20,000 cell/cm$^2$) and maintained under Condition A medium.
2. Medium was changed every other day until the colonies formed.
3. When the culture reached to >80% confluence, the medium was removed by aspiration. Accutase was added to dissociate the cells into single cells.
4. The dissociated cells were collected and neutralized by stop medium.
5. Cells were centrifuged at 1,400 r.p.m. for 4 minutes.
6. Supernatant was removed by aspiration.

7. The pellet was resuspended by Condition A medium and replated at a ratio of 1:10 onto the irradiated feeder cells.
8. Medium was changed every other day until confluent and repeat subculture steps.

*The morphology of the condition A colonies will be stable after 3-5 passages.

| Condition A medium (CFKBRA + RI) | |
|---|---|
| SFD-based media | |
| CHIR99021 | 3 μM |
| FGF10 | 10 ng/ml |
| FGF7 | 10 ng/ml |
| BMP4 | 10 ng/ml |
| Retinoic acid | 50 nM |
| Y27632 | 10 μM |

For Condition B Cells:
Switching Method
1. Remove the Condition A medium from condition A cells and add Condition B medium into the well/plate.
2. Change medium every other day until the cells are confluent.
3. When the cells are confluent, remove the Condition B medium, wash the well/plate with PBS twice, and dissociate the cells with 0.05% trypsin.

*The feeder cells can be removed by differential trypsinization for less than 3 minutes.

4. The dissociated cells were collected and neutralized by stop medium.
5. Cells were centrifuged at 1,400 r.p.m. for 4 minutes.
6. Supernatant was removed by aspiration.
7. The pellet was resuspended by Condition B medium and replated at a ratio of 1:10 onto the irradiated feeder cells.
8. Medium was changed every other day until confluent and repeat subculture steps.

| Condition B medium | | | |
|---|---|---|---|
| DMEM high glucose | 500 ml | Y27632 | 5 μM |
| Ham's F12 | 185 ml | Pen-Strep | 1X |
| FBS | 50 ml | | |
| insulin (4 mg/ml) | 922.5 ul | | |
| EGF (0.125 ug/ml) | 738 ul | | |
| hydrocortisone (25 ug/ml) | 738 ul | | |
| cholera toxin (1 mg/ml) | 6.34 ul | | |

Trachea Protocol

Tracheas were isolated from NSG mice, cannulated with 22G needle, and embedded in 2% agarose. When the agarose had solidified, the needle was removed to create a channel on the luminal side of trachea. 0.25% of trypsin was warmed up to 37° C. and pumped into the channel with a speed of 0.1 ml/min for 15 mins followed by 5% FBS/IMEM media for 5 mins. One million of EPI cells in 10 μl EPI media was used to fill up the channel and incubated overnight. The trachea was washed by EPI media the next day to remove unattached cells. The whole trachea was incubated in EPI media ex vivo for 7 days before analysis. Media was changed every other day.

REFERENCES

1. Robinton, D. A. & Daley, G. Q. The promise of induced pluripotent stem cells in research and therapy. Nature 481, 295-305, doi:nature10761 10.1038/nature10761 (2012).
2. Petersen, T. H. et al. Tissue-engineered lungs for in vivo implantation. Science 329, 538-541, doi:science.1189345 10.1126/science.1189345 (2010).
3. Morrisey, E. E. & Hogan, B. L. Preparing for the first breath: genetic and cellular mechanisms in lung development. Dev Cell 18, 8-23, doi:S1534-5807(09)00527-9 [pii] 10.1016/j.devcel.2009.12.010 (2010).
4. Noble, P. W., Barkauskas, C. E. & Jiang, D. Pulmonary fibrosis: patterns and perpetrators. J Clin Invest 122, 2756-2762, doi:10.1172/JCI60323 (2012).
5. Ryu, J. H. et al. Idiopathic pulmonary fibrosis: evolving concepts. Mayo Clinic proceedings 89, 1130-1142, doi: 10.1016/j.mayocp.2014.03.016 (2014).
6. King, T. E., Jr. et al. A phase 3 trial of pirfenidone in patients with idiopathic pulmonary fibrosis. The New England journal of medicine 370, 2083-2092, doi: 10.1056/NEJMoa1402582 (2014).
7. Richeldi, L. et al. Efficacy and safety of nintedanib in idiopathic pulmonary fibrosis. The New England journal of medicine 370, 2071-2082, doi:10.1056/NEJ-Moa1402584 (2014).
8. McCurry, K. R. et al. Lung transplantation in the United States, 1998-2007. Am J Transplant 9, 942-958, doi: AJT2569 [pii]10.1111/j.1600-6143.2009.02569.x (2009).
9. Steele, M. P. & Schwartz, D. A. Molecular mechanisms in progressive idiopathic pulmonary fibrosis. Annual review of medicine 64, 265-276, doi:10.1146/annurev-med-042711-142004 (2013).
10. Mulugeta, S., Nureki, S. & Beers, M. F. Lost after translation: insights from pulmonary surfactant for understanding the role of alveolar epithelial dysfunction and cellular quality control in fibrotic lung disease. American journal of physiology. Lung cellular and molecular physiology 309, L507-525, doi:10.1152/ajplung.00139.2015 (2015).
11. Zhang, Y., Noth, I., Garcia, J. G. & Kaminski, N. A variant in the promoter of MUCSB and idiopathic pulmonary fibrosis. The New England journal of medicine 364, 1576-1577, doi:10.1056/NEJMc1013504 (2011).
12. Fingerlin, T. E. et al. Genome-wide association study identifies multiple susceptibility loci for pulmonary fibrosis. Nat Genet 45, 613-620, doi:10.1038/ng.2609 (2013).
13. Seibold, M. A. et al. A common MUCSB promoter polymorphism and pulmonary fibrosis. The New England journal of medicine 364, 1503-1512, doi:10.1056/NEJ-Moa1013660 (2011).
14. Yang, I. V., Fingerlin, T. E., Evans, C. M., Schwarz, M. I. & Schwartz, D. A. MUCSB and Idiopathic Pulmonary Fibrosis. Ann Am Thorac Soc 12 Suppl 2, S193-199, doi:10.1513/AnnalsATS.201503-110AW (2015).
15. Loyd, J. E. Pulmonary fibrosis in families American journal of respiratory cell and molecular biology 29, S47-50 (2003).
16. Whitsett, J. A., Wert, S. E. & Weaver, T. E. Diseases of pulmonary surfactant homeostasis. Annual review of pathology 10, 371-393, doi:10.1146/annurev-pathol-012513-104644 (2015).
17. Wang, Y. et al. Genetic defects in surfactant protein A2 are associated with pulmonary fibrosis and lung cancer. American journal of human genetics 84, 52-59, doi: 10.1016/j.ajhg.2008.11.010 (2009).
18. Lawson, W. E. et al. Genetic mutations in surfactant protein C are a rare cause of sporadic cases of IPF. Thorax 59, 977-980, doi:10.1136/thx.2004.026336 (2004).
19. Thomas, A. Q. et al. Heterozygosity for a surfactant protein C gene mutation associated with usual interstitial pneumonitis and cellular nonspecific interstitial pneumo- 19. ...nitis in one kindred. Am J Respir Crit Care Med 165, 1322-1328, doi:10.1164/rccm.200112-1230C (2002).
20. Lawson, W. E. et al. Endoplasmic reticulum stress enhances fibrotic remodeling in the lungs. Proc Natl Acad Sci USA 108, 10562-10567, doi:10.1073/pnas.1107559108 (2011).
21. Korfei, M. et al. Epithelial endoplasmic reticulum stress and apoptosis in sporadic idiopathic pulmonary fibrosis. Am J Respir Crit Care Med 178, 838-846, doi:10.1164/rccm.200802-3130C (2008).
22. Tanjore, H., Blackwell, T. S. & Lawson, W. E. Emerging evidence for endoplasmic reticulum stress in the pathogenesis of idiopathic pulmonary fibrosis. American journal of physiology. Lung cellular and molecular physiology 302, L721-729, doi:10.1152/ajplung.00410.2011 (2012).
23. Hawkins, A. et al. A non-BRICHOS SFTPC mutant (SP-CI73T) linked to interstitial lung disease promotes a late block in macroautophagy disrupting cellular proteostasis and mitophagy. American journal of physiology. Lung cellular and molecular physiology 308, L33-47, doi:10.1152/ajplung.00217.2014 (2015).
24. Araya, J. et al. Insufficient autophagy in idiopathic pulmonary fibrosis. American journal of physiology. Lung cellular and molecular physiology 304, L56-69, doi:10.1152/ajplung.00213.2012 (2013).
25. Margaritopoulos, G. A. et al. Self-eating: friend or foe? The emerging role of autophagy in idiopathic pulmonary fibrosis. BioMed research international 2013, 420497, doi:10.1155/2013/420497 (2013).
26. Patel, A. S. et al. Autophagy in idiopathic pulmonary fibrosis. PLoS One 7, e41394, doi:10.1371/journal.pone.0041394 (2012).
27. Bueno, M. et al. PINK1 deficiency impairs mitochondrial homeostasis and promotes lung fibrosis. J Clin Invest, doi:10.1172/JCI74942 (2014).
28. Armanios, M. Y. et al. Telomerase mutations in families with idiopathic pulmonary fibrosis. The New England journal of medicine 356, 1317-1326, doi:10.1056/NEJMoa066157 (2007).
29. Alder, J. K. et al. Short telomeres are a risk factor for idiopathic pulmonary fibrosis. Proc Natl Acad Sci USA 105, 13051-13056, doi:10.1073/pnas.0804280105 (2008).
30. Alder, J. K. et al. Ancestral mutation in telomerase causes defects in repeat addition processivity and manifests as familial pulmonary fibrosis. PLoS genetics 7, e1001352, doi:10.1371/journal.pgen.1001352 (2011).
31. Alder, J. K. et al. Exome sequencing identifies mutant TINF2 in a family with pulmonary fibrosis. Chest, doi:10.1378/chest.14-1947 (2014).
32. Armanios, M. Telomerase mutations and the pulmonary fibrosis-bone marrow failure syndrome complex. The New England journal of medicine 367, 384; author reply 384, doi:10.1056/NEJMc1206730#SA1 (2012).
33. Armanios, M. Telomerase and idiopathic pulmonary fibrosis. Mutation research 730, 52-58, doi:10.1016/j.mrfmmm 2011.10.013 (2012).
34. Stuart, B. D. et al. Exome sequencing links mutations in PARN and RTEL1 with familial pulmonary fibrosis and telomere shortening. Nat Genet 47, 512-517, doi:10.1038/ng.3278 (2015).
35. Desai, T. J., Brownfield, D. G. & Krasnow, M. A. Alveolar progenitor and stem cells in lung development, renewal and cancer. Nature 507, 190-194, doi:10.1038/nature12930 (2014).
36. Rock, J. R. et al. Multiple stromal populations contribute to pulmonary fibrosis without evidence for epithelial to mesenchymal transition. Proc Natl Acad Sci USA 108, E1475-1483, doi:10.1073/pnas.1117988108 (2011).
37. Barkauskas, C. E. et al. Type 2 alveolar cells are stem cells in adult lung. J Clin Invest, doi:10.1172/JCI68782 (2013).
38. Alder, J. K. et al. Telomere dysfunction causes alveolar stem cell failure. Proc Natl Acad Sci USA 112, 5099-5104, doi:10.1073/pnas.1504780112 (2015).
39. Young, L. R. et al. The alveolar epithelium determines susceptibility to lung fibrosis in Hermansky-Pudlak syndrome. Am J Respir Crit Care Med 186, 1014-1024, doi:10.1164/rccm.201207-12060C (2012).
40. Mahavadi, P., Guenther, A. & Gochuico, B. R. Hermansky-Pudlak syndrome interstitial pneumonia: it's the epithelium, stupid! Am J Respir Crit Care Med 186, 939-940, doi:10.1164/rccm.201210-1771ED (2012).
41. Pierson, D. M. et al. Pulmonary fibrosis in hermansky-pudlak syndrome. a case report and review. Respiration; international review of thoracic diseases 73, 382-395, doi:10.1159/000091609 (2006).
42. Seward, S. L., Jr. & Gahl, W. A. Hermansky-Pudlak syndrome: health care throughout life. Pediatrics 132, 153-160, doi:10.1542/peds.2012-4003 (2013).
43. Whitsett, J. A., Wert, S. E. & Weaver, T. E. Alveolar surfactant homeostasis and the pathogenesis of pulmonary disease. Annual review of medicine 61, 105-119, doi:10.1146/annurev.med.60.041807.123500 (2010).
44. Ott, H. C. et al. Regeneration and orthotopic transplantation of a bioartificial lung. Nat Med 16, 927-933, doi:nm.2193 [pii]10.1038/nm.2193 (2010).
45. Yamanaka, S. A fresh look at iPS cells. Cell 137, 13-17, doi:S0092-8674(09)00333-X [pii] 10.1016/j.cell.2009.03.034 (2009).
46. Takahashi, K. et al. Induction of pluripotent stem cells from adult human fibroblasts by defined factors. Cell 131, 861-872, doi:10.1016/j.cell.2007.11.019 (2007).
47. Yu, J. et al. Induced pluripotent stem cell lines derived from human somatic cells. Science 318, 1917-1920, doi: 1151526 [pii] 10.1126/science.1151526 (2007).
48. Rock, J. R. & Hogan, B. L. Epithelial progenitor cells in lung development, maintenance, repair, and disease. Annu Rev Cell Dev Biol 27, 493-512, doi:10.1146/annurev-cellbio-100109-104040 (2011).
49. Badylak, S. F., Weiss, D. J., Caplan, A. & Macchiarini, P. Engineered whole organs and complex tissues. Lancet 379, 943-952, doi:10.1016/S0140-6736(12)60073-7 (2012).
50. Macchiarini, P. et al. Clinical transplantation of a tissue-engineered airway. Lancet 372, 2023-2030, doi:S0140-6736(08)61598-6 [pii] 10.1016/S0140-6736(08)61598-6 (2008).
51. Laurance, J. British boy receives trachea transplant built with his own stem cells. BMJ 340, c1633 (2010).
52. Jungebluth, P. et al. Tracheobronchial transplantation with a stem-cell-seeded bioartificial nanocomposite: a proof-of-concept study. Lancet 378, 1997-2004, doi:Doi 10.1016/S0140-6736(11)61715-7 (2011).
53. Sheridan, W. P. et al. Effect of peripheral-blood progenitor cells mobilised by filgrastim (G-CSF) on platelet recovery after high-dose chemotherapy. Lancet 339, 640-644 (1992).
54. Delaere, P., Vranckx, J., Verleden, G., De Leyn, P. & Van Raemdonck, D. Tracheal allotransplantation after withdrawal of immunosuppressive therapy. The New England 55. Delaere, P. R. et al. Learning curve in tracheal allotransplantation. Am J Transplant 12, 2538-2545, doi:10.1111/j.1600-6143.2012.04125.x (2012).
56. Delaere, P. R. Tracheal transplantation. Current opinion in pulmonary medicine 18, 313-320, doi:10.1097/MCP.0b013e3283539673 (2012).
57. Rawlins, E. L. & Hogan, B. L. Ciliated epithelial cell lifespan in the mouse trachea and lung. American journal of physiology. Lung cellular and molecular physiology 295, L231-234, doi:90209.2008 [pii] 10.1152/ajplung.90209.2008 (2008).
58. Giangreco, A., Reynolds, S. D. & Stripp, B. R. Terminal bronchioles harbor a unique airway stem cell population that localizes to the bronchoalveolar duct junction. The American journal of pathology 161, 173-182, doi:S0002-9440(10)64169-7 [pii] 10.1016/S0002-9440(10)64169-7 (2002).
59. Hong, K. U., Reynolds, S. D., Giangreco, A., Hurley, C. M. & Stripp, B. R. Clara cell secretory protein-expressing cells of the airway neuroepithelial body microenvironment include a label-retaining subset and are critical for epithelial renewal after progenitor cell depletion. American journal of respiratory cell and molecular biology 24, 671-681 (2001).
60. Rawlins, E. L. et al. The role of Scgb1a1+Clara cells in the long-term maintenance and repair of lung airway, but not alveolar, epithelium. Cell Stem Cell 4, 525-534, doi:S1934-5909(09)00156-8 [pii] 10.1016/j.stem.2009.04.002 (2009).
61. Rock, J. R. et al. Basal cells as stem cells of the mouse trachea and human airway epithelium. Proc Natl Acad Sci USA 106, 12771-12775, doi:0906850106 [pii] 10.1073/pnas.0906850106 (2009).
62. Hegab, A. E. et al. Novel stem/progenitor cell population from murine tracheal submucosal gland ducts with multipotent regenerative potential. Stem Cells 29, 1283-1293, doi:10.1002/stem.680 (2011).
63. Lynch, T. J. et al. Submucosal Gland Myoepithelial Cells Are Reserve Stem Cells That Can Regenerate Mouse Tracheal Epithelium. Cell Stem Cell, doi:10.1016/j.stem.2018.03.017 (2018).
64. Tata, P. R. et al. Dedifferentiation of committed epithelial cells into stem cells in vivo. Nature 503, 218-223, doi:10.1038/nature12777 (2013).
65. Beers, M. F. & Morrisey, E. E. The three R's of lung health and disease: repair, remodeling, and regeneration. J Clin Invest 121, 2065-2073, doi:10.1172/JCI45961 (2011).
66. Barkauskas, C. E. et al. Type 2 alveolar cells are stem cells in adult lung. J Clin Invest 123, 3025-3036, doi:10.1172/JCI68782 (2013).
67. Jain, R. et al. Plasticity of Hopx(+) type I alveolar cells to regenerate type II cells in the lung. Nature communications 6, 6727, doi:10.1038/ncomms7727 (2015).
68. Kumar, P. A. et al. Distal airway stem cells yield alveoli in vitro and during lung regeneration following H1N1 influenza infection. Cell 147, 525-538, doi:S0092-8674(11)01173-1 [pii] 10.1016/j.cell.2011.10.001 (2011).
69. Vaughan, A. E. et al. Lineage-negative progenitors mobilize to regenerate lung epithelium after major injury. Nature 517, 621-625, doi:10.1038/nature14112 (2015).
70. Zuo, W. et al. p63(+) Krt5(+) distal airway stem cells are essential for lung regeneration. Nature 517, 616-620, doi:10.1038/nature13903 (2015).
71. Yang, Y. et al. Spatial-Temporal Lineage Restrictions of Embryonic p63(+) Progenitors Establish Distinct Stem Cell Pools in Adult Airways. Dev Cell 44, 752-761 e754, doi:10.1016/j.devcel.2018.03.001 (2018).
72. Plopper, C. G. & Hyde, D. M. The non-human primate as a model for studying COPD and asthma. Pulmonary pharmacology & therapeutics 21, 755-766, doi:10.1016/j.pupt.2008.01.008 (2008).
73. Smith, L. J., McKay, K. O., van Asperen, P. P., Selvadurai, H. & Fitzgerald, D. A. Normal development of the lung and premature birth. Paediatric respiratory reviews 11, 135-142, doi:10.1016/j.prrv.2009.12.006 (2010).
74. Krasteva, G. & Kummer, W. "Tasting" the airway lining fluid. Histochemistry and cell biology, doi:10.1007/s00418-012-0993-5 (2012).
75. Rawlins, E. L. & Hogan, B. L. Intercellular growth factor signaling and the development of mouse tracheal submucosal glands. Dev Dyn 233, 1378-1385, doi:10.1002/dvdy.20461 (2005).
76. Herriges, M. & Morrisey, E. E. Lung development: orchestrating the generation and regeneration of a complex organ. Development 141, 502-513, doi:10.1242/dev.098186 (2014).
77. Warburton, D. et al. Lung organogenesis. Current topics in developmental biology 90, 73-158, doi:10.1016/S0070-2153(10)90003-3 (2010).
78. Herring, M. J., Putney, L. F., Wyatt, G., Finkbeiner, W. E. & Hyde, D. M. Growth of alveoli during postnatal development in humans based on stereological estimation. American journal of physiology. Lung cellular and molecular physiology 307, L338-344, doi:10.1152/ajplung.00094.2014 (2014).
79. McMullan, R. et al. Keratinocyte differentiation is regulated by the Rho and ROCK signaling pathway. Current biology: CB 13, 2185-2189 (2003).
80. Chapman, S., Liu, X., Meyers, C., Schlegel, R. & McBride, A. A. Human keratinocytes are efficiently immortalized by a Rho kinase inhibitor. J Clin Invest 120, 2619-2626, doi:10.1172/JCI42297 (2010).
81. Liu, X. et al. ROCK inhibitor and feeder cells induce the conditional reprogramming of epithelial cells. The American journal of pathology 180, 599-607, doi:10.1016/j.ajpath.2011.10.036 (2012).
82. Wang, X. et al. Cloning and variation of ground state intestinal stem cells. Nature 522, 173-178, doi:10.1038/nature14484 (2015).
83. Butler, C. R. et al. Rapid Expansion of Human Epithelial Stem Cells Suitable for Airway Tissue Engineering. Am J Respir Crit Care Med 194, 156-168, doi:10.1164/rccm.201507-14140C (2016).
84. Mou, H. et al. Dual SMAD Signaling Inhibition Enables Long-Term Expansion of Diverse Epithelial Basal Cells. Cell Stem Cell 19, 217-231, doi:10.1016/j.stem.2016.05.012 (2016).
85. Que, J., Choi, M., Ziel, J. W., Klingensmith, J. & Hogan, B. L. Morphogenesis of the trachea and esophagus: current players and new roles for noggin and Bmps. Differentiation; research in biological diversity 74, 422-437, doi:10.1111/j.1432-0436.2006.00096.x (2006).
86. Que, J. et al. Multiple dose-dependent roles for Sox2 in the patterning and differentiation of anterior foregut endoderm. Development 134, 2521-2531, doi:10.1242/dev.003855 (2007).
87. Liu, Y. & Hogan, B. L. Differential gene expression in the distal tip endoderm of the embryonic mouse lung. Gene expression patterns: GEP 2, 229-233 (2002).

88. Rawlins, E. L., Clark, C. P., Xue, Y. & Hogan, B. L. The Id2+ distal tip lung epithelium contains individual multipotent embryonic progenitor cells. Development 136, 3741-3745, doi:10.1242/dev.037317 (2009).
89. Treutlein, B. et al. Reconstructing lineage hierarchies of the distal lung epithelium using single-cell RNA-seq. Nature 509, 371-375, doi:10.1038/nature13173 (2014).
90. Frank, D. B. et al. Emergence of a Wave of Wnt Signaling that Regulates Lung Alveologenesis by Controlling Epithelial Self-Renewal and Differentiation. Cell reports 17, 2312-2325, doi:10.1016/j.celrep.2016.11.001 (2016).
91. Swarr, D. T. & Morrisey, E. E. Lung endoderm morphogenesis: gasping for form and function. Annu Rev Cell Dev Biol 31, 553-573, doi:10.1146/annurev-cellbio-100814-125249 (2015).
92. Nikolic, M. Z. et al. Human embryonic lung epithelial tips are multipotent progenitors that can be expanded in vitro as long-term self-renewing organoids. eLife 6, doi:10.7554/eLife.26575 (2017).
93. Murry, C. E. & Keller, G. Differentiation of embryonic stem cells to clinically relevant populations: lessons from embryonic development. Cell 132, 661-680, doi:S0092-8674(08)00216-X [pii] 10.1016/j.cell.2008.02.008 (2008).
94. Hanna, J. H., Saha, K. & Jaenisch, R. Pluripotency and cellular reprogramming: facts, hypotheses, unresolved issues. Cell 143, 508-525, doi:10.1016/j.cell.2010.10.008 (2010).
95. Takahashi, K. & Yamanaka, S. Induction of pluripotent stem cells from mouse embryonic and adult fibroblast cultures by defined factors. Cell 126, 663-676, doi:S0092-8674(06)00976-7 [pii] 10.1016/j.cell.2006.07.024 (2006).
96. Okita, K. & Yamanaka, S. Induced pluripotent stem cells: opportunities and challenges. Philos Trans R Soc Lond B Biol Sci 366, 2198-2207, doi:10.1098/rstb.2011.0016 (2011).
97. Park, I. H. et al. Reprogramming of human somatic cells to pluripotency with defined factors. Nature 451, 141-146, doi:10.1038/nature06534 (2008).
98. Miller, A. J. et al. In Vitro Induction and In Vivo Engraftment of Lung Bud Tip Progenitor Cells Derived from Human Pluripotent Stem Cells. Stem Cell Reports 10, 101-119, doi:10.1016/j.stemcr.2017.11.012 (2018).
99. Nichane, M. et al. Isolation and 3D expansion of multipotent Sox9(+) mouse lung progenitors. Nature methods 14, 1205-1212, doi:10.1038/nmeth.4498 (2017).
100. McCauley, K. B. et al. Efficient Derivation of Functional Human Airway Epithelium from Pluripotent Stem Cells via Temporal Regulation of Wnt Signaling. Cell Stem Cell 20, 844-857 e846, doi:10.1016/j.stem.2017.03.001 (2017).
101. Crapo, J. D., Barry, B. E., Foscue, H. A. & Shelburne, J. Structural and biochemical changes in rat lungs occurring during exposures to lethal and adaptive doses of oxygen. The American review of respiratory disease 122, 123-143 (1980).
102. Crapo, J. D. Morphologic changes in pulmonary oxygen toxicity. Annu Rev Physiol 48, 721-731, doi:10.1146/annurev.ph.48.030186.003445 (1986).
103. Mantell, L. L. & Lee, P. J. Signal transduction pathways in hyperoxia-induced lung cell death. Mol Genet Metab 71, 359-370, doi:10.1006/mgme.2000.3046 (2000).
104. Tanaka, A. et al. Hyperoxia-induced LC3B interacts with the Fas apoptotic pathway in epithelial cell death. Am J Respir Cell Mol Biol 46, 507-514, doi:10.1165/rcmb.2009-0415OC (2012).
105. Kazzaz, J. A. et al. Cellular oxygen toxicity. Oxidant injury without apoptosis. J Biol Chem 271, 15182-15186 (1996).
106. Barazzone, C., Horowitz, S., Donati, Y. R., Rodriguez, I. & Piguet, P. F. Oxygen toxicity in mouse lung: pathways to cell death. Am J Respir Cell Mol Biol 19, 573-581, doi:10.1165/ajrcmb.19.4.3173 (1998).
107. Petrache, I. et al. Mitogen-activated protein kinase pathway mediates hyperoxia-induced apoptosis in cultured macrophage cells. Am J Physiol 277, L589-595 (1999).
108. McGrath-Morrow, S. A. & Stahl, J. Apoptosis in neonatal murine lung exposed to hyperoxia. Am J Respir Cell Mol Biol 25, 150-155, doi:10.1165/ajrcmb.25.2.4362 (2001).
109. O'Reilly, M. A. et al. The cyclin-dependent kinase inhibitor p21 protects the lung from oxidative stress. Am J Respir Cell Mol Biol 24, 703-710, doi:10.1165/ajrcmb.24.6.4355 (2001).
110. De Paepe, M. E. et al. Hyperoxia-induced apoptosis and Fas/FasL expression in lung epithelial cells. Am J Physiol Lung Cell Mol Physiol 289, L647-659, doi:10.1152/ajplung.00445.2004 (2005).
111. Pagano, A. et al. Poly(ADP-ribose)polymerase activation mediates lung epithelial cell death in vitro but is not essential in hyperoxia-induced lung injury. Am J Respir Cell Mol Biol 33, 555-564, doi:10.1165/rcmb.2004-0361OC (2005).
112. Beck, J. M. et al. *Pneumocystis* pneumonia increases the susceptibility of mice to sublethal hyperoxia. Infect Immun 71, 5970-5978 (2003).
113. Alphonse, R. S. et al. Existence, functional impairment, and lung repair potential of endothelial colony-forming cells in oxygen-induced arrested alveolar growth. Circulation 129, 2144-2157, doi:10.1161/CIRCULATIONAHA.114.009124 (2014).
114. Rawlins, E. L., Ostrowski, L. E., Randell, S. H. & Hogan, B. L. Lung development and repair: contribution of the ciliated lineage. Proc Natl Acad Sci USA 104, 410-417, doi:10.1073/pnas.0610770104 (2007).
115. Borthwick, D. W., Shahbazian, M., Krantz, Q. T., Dorin, J. R. & Randell, S. H. Evidence for stem-cell niches in the tracheal epithelium. Am J Respir Cell Mol Biol 24, 662-670, doi:10.1165/ajrcmb.24.6.4217 (2001).
116. O'Koren, E. G., Hogan, B. L. & Gunn, M. D. Loss of basal cells precedes bronchiolitis obliterans-like pathological changes in a murine model of chlorine gas inhalation. Am J Respir Cell Mol Biol 49, 788-797, doi:10.1165/rcmb.2012-0369OC (2013).
117. Guha, A. et al. Neuroepithelial body microenvironment is a niche for a distinct subset of Clara-like precursors in the developing airways. Proc Natl Acad Sci USA 109, 12592-12597, doi:10.1073/pnas.1204710109 (2012).
118. Guha, A. et al. Analysis of Notch signaling-dependent gene expression in developing airways reveals diversity of Clara cells. PLoS One 9, e88848, doi:10.1371/journal.pone.0088848 (2014).
119. Song, H. et al. Functional characterization of pulmonary neuroendocrine cells in lung development, injury, and tumorigenesis. Proc Natl Acad Sci USA 109, 17531-17536, doi:10.1073/pnas.1207238109 (2012).
120. Rock, J. R. et al. Notch-dependent differentiation of adult airway basal stem cells. Cell Stem Cell 8, 639-648, doi:S1934-5909(11)00168-8 [pii] 10.1016/j.stem.2011.04.003 (2011).

121. Rosen, C. et al. Preconditioning allows engraftment of mouse and human embryonic lung cells, enabling lung repair in mice. Nat Med 21, 869-879, doi:10.1038/nm.3889 (2015).
122. Verhoeven, D., Teijaro, J. R. & Farber, D. L. Pulse-oximetry accurately predicts lung pathology and the immune response during influenza infection. Virology 390, 151-156, doi:10.1016/j.virol.2009.05.004 (2009).
123. Bot, A. et al. Cellular mechanisms involved in protection and recovery from influenza virus infection in immunodeficient mice. J Virol 70, 5668-5672 (1996).
124. Huang, S. X. et al. The in vitro generation of lung and airway progenitor cells from human pluripotent stem cells. Nature protocols 10, 413-425, doi:10.1038/nprot.2015.023 (2015).
125. Huang, S. X. et al. Efficient generation of lung and airway epithelial cells from human pluripotent stem cells. Nature biotechnology 32, 84-91, doi:10.1038/nbt.2754 (2014).
126. Green, M. D. et al. Generation of anterior foregut endoderm from human embryonic and induced pluripotent stem cells. Nature biotechnology 29, 267-272, doi:10.1038/nbt.1788 (2011).
127. Firth, A. L. et al. Generation of multiciliated cells in functional airway epithelia from human induced pluripotent stem cells. Proc Natl Acad Sci USA 111, E1723-1730, doi:10.1073/pnas.1403470111 (2014).
128. Chen, Y. W. et al. A three-dimensional model of human lung development and disease from pluripotent stem cells. Nature cell biology 19, 542-549, doi:10.1038/ncb3510 (2017).
129. Gotoh, S. et al. Generation of alveolar epithelial spheroids via isolated progenitor cells from human pluripotent stem cells. Stem cell reports 3, 394-403, doi:10.1016/j.stemcr.2014.07.005 (2014).
130. Konishi, S. et al. Directed Induction of Functional Multi-ciliated Cells in Proximal Airway Epithelial Spheroids from Human Pluripotent Stem Cells. Stem cell reports 6, 18-25, doi:10.1016/j.stemcr.2015.11.010 (2016).
131. Wong, A. P. et al. Directed differentiation of human pluripotent stem cells into mature airway epithelia expressing functional CFTRTR protein. Nature biotechnology 30, 876-882, doi:10.1038/nbt.2328 (2012).
132. Mou, H. et al. Generation of Multipotent Lung and Airway Progenitors from Mouse ESCs and Patient-Specific Cystic Fibrosis iPSCs. Cell Stem Cell 10, 385-397, doi:S1934-5909(12)00056-2 [pii] 10.1016/j.stem.2012.01.018 (2012).
133. Matute-Bello, G., Frevert, C. W. & Martin, T. R. Animal models of acute lung injury. American journal of physiology. Lung cellular and molecular physiology 295, L379-399, doi:00010.2008 [pii] 10.1152/ajplung.00010.2008 (2008).
134. Dorrello, N. V. et al. Functional vascularized lung grafts for lung bioengineering. Sci Adv 3, e1700521, doi:10.1126/sciadv.1700521 (2017).
135. Lynch, T. J. et al. Submucosal Gland Myoepithelial Cells Are Reserve Stem Cells That Can Regenerate Mouse Tracheal Epithelium. Cell Stem Cell 22, 779, doi:10.1016/j.stem.2018.04.007 (2018).
136. Tata, A. et al. Myoepithelial Cells of Submucosal Glands Can Function as Reserve Stem Cells to Regenerate Airways after Injury. Cell Stem Cell 22, 668-683 e666, doi:10.1016/j.stem.2018.03.018 (2018).
137. Lynch, T. J. et al. Submucosal Gland Myoepithelial Cells Are Reserve Stem Cells That Can Regenerate Mouse Tracheal Epithelium. Cell Stem Cell, doi:10.1016/j.stem.2018.03.017 (2018).
138. Xie, Y. et al. Mucociliary Transport in Healthy and Cystic Fibrosis Pig Airways. Ann Am Thorac Soc 15, S171-S176, doi:10.1513/AnnalsATS.201805-308AW (2018).
139. McCarron, A., Donnelley, M. & Parsons, D. Airway disease phenotypes in animal models of cystic fibrosis. Respiratory research 19, 54, doi:10.1186/s12931-018-0750-y (2018).

Further Methods and Reagents

Development of LBO occurs in basically three stages:

Stage 1: suspension cultures of in vitro generated anterior foregut cells to form LBOs that are spherical structures with folded epithelium and mesenchynal component (up to d25).

Stage 2: In 3D Matrigel culture, which starts at about d25, the unbranched LBO spheres start branching within one week. After xenotransplantation under the kidney capsule of immune deficient mice, branching takes longer and is observed about 2 months after grafting.

Stage 3: lastly, when cultured long-term as xenotransplant or 3D Matrigel culture, the BLBOs begin to show dilated tips similar to alveolar structures.

The longer the LBOs are cultured (in either 3D or xenotransplants) the more developed is the branching morphogenesis. BLBO-3D cultures have been grown for as long as 180 days and BLBO-xeno have been followed up to 7 months. There are more mature alveolar cells the longer the BLBO are grown and the organoids are larger.

Whether BLBO-3D or BLBO-xeno are used, drug screening will typically be done in vitro, using BLBO-3D followed by validation in vivo using BLBO-xeno.

The term "lung-disease related mutation" as used herein relates to a gene mutation or polymorphism known to cause a lung disease phenotype. For example, certain lung diseases are caused by gene mutations in the following, non-exhaustive list of genes: HPS1, 2, 4, hTERT, hTERC, dyskerin, CFTR, DKC1, SFPTB, SFTPC, SFTPA1, SFTPA2, MUC5B, SHH, PTCH, SMO, ABCA3. The gene ID Nos for these genes is provided below:

| gene name | gene ID | alternative name |
|---|---|---|
| CFTR | 1080 | |
| HPS1 | 3257 | |
| HPS2 | 7031 | TFF1 |
| HPS4 | 89781 | |
| TERT | 7015 | |
| TERC | 7012 | |
| DKC1 | 1736 | |
| SFTPB | 6439 | |
| SFTPC | 6440 | |
| SFTPA1 | 653509 | |
| SFTPA2 | 729238 | |
| MUC5B | 727897 | |
| SHH | 6469 | |
| PTCH1 | 5727 | |
| SMO | 6608 | |
| ABCA3 | 21 | |

In addition, cystic fibrosis is associated with gene mutations in the cystic fibrosis transmembrane conductance regulator (CFTR) and polymorphisms associated sodium channel epithelial 1 alpha (SCNN1A) genes, and such mutations/polymorphisms are highly variable. With reference to the expressed proteins of such genes, the mutations include F508 in the a CFTR protein, G551 in a CFTR protein, G542 in a CFTR protein, N1303 in a CFTR protein, R117 in a CFTR protein, W1282 in a CFTR protein, R553 in a CFTR protein, c.3849+10 kb in a CFTR protein, c.2657+5 in a CFTR protein, c.3140-26 in a CFTR protein, and V114 in a SCNN1A protein. In addition, the publication entitled *Differentiation of Human Pluripotent Stem Cells into Functional Lung Alveolar Epithelial Cells* by Anjali Jacob, et al., Cell Stem Cell 21, 1-17, Oct. 5, 2017 uses such Crispr/cas system to correct the homozygous surfactant mutation (SFTPB121ins2) to restore surfactant processing in alveolar epithelial type 2 cells. Another publication entitled *Efficient Derivation of Functional Human Airway Epithelium from Pluripotent Stem Cells via Temporal Regulation of Wnt Signaling* by Katherine B. McCauley, et al., 2017, Cell Stem Cell 20, 844-857 uses CRISPR to correct a defect in forskolin-induced swelling that is rescued by gene editing to correct the disease mutation associated with a compound heterozygous CFTR genotype DF508/DF508.

Cells harboring mutated gene including, but not limited to, those described above can be subjected to a CRISPR/Cas system according to techniques known in the art (see, e.g., US Patent Pub. 20170022507) and described herein. Typically, the cells are subjected to the CRISPR/Cas induced genetic correction at a stage of growth and expansion such at a pluripotent stage. These cells would then be developed into LBOs and observed for changes in phenotype and/or biomarker expression.

Central Role of Type II Alveolar Epithelial Cells in IPF and Familial PF

The respiratory system originates from buds that arise on the ventral aspect of the anterior foregut endoderm (AFE) and develop through a stereotyped branching process into proximal airways and distal alveolar progenitors (pseudoglandular stage). During the canalicular stage, cell cycle activity decreases, and specialization of the airway epithelium occurs in the stalks, with the emergence of basal, goblet, club, ciliated, and other cell types. This stage is followed by the saccular stage, where the canaliculi widen into distal sacculations that will give rise to primitive alveoli[9,10].

We previously reported a strategy to differentiate hPSCs (embryonic stem cells (ESCs) and reprogrammed induced pluripotent stem cells (iPSCs)) in 2D through sequential developmental steps from definitive endoderm (DE) to AFE, lung field progenitors, and, finally, lung and airway epithelial cells. These developments are disclosed in U.S. Pat. Nos. 9,719,067; 9,234,170 and 9,988,606, the contents of which are incorporated herein by reference in their entirety.

Formation of Lung Tissue with Branching Morphogenesis

Lung bud organoids are produced according to the techniques of as described below. The protocol involves three stages. First, human pluripotent cells, such as induced pluripotent stem cells or embryonic stem cells (or any stem or progenitor cells as described herein), are subjected to Embryoid bodies/primitive streak formation media under conditions to induce differentiation of the pluripotent cells to definitive endoderm (DE). This first stage typically takes 4 days (d0-d4) and forms embryoid bodies having endoderm as determined through expression of CXCR4 and c-kit. Second, (d5-d6) embryoid bodies are subjected to Anteriorization media under conditions for the embryoid bodies to form anterior foregut patterning. Third, (d6-d20-25) cells are then subjected to ventralization media/branching media under conditions that induce ventralization and ultimate production of lung bud organoids (LBOs). LBO formation is determined by sonic hedgehog (SHH) expression on the tips of budding epithelial structures.

Upon production of LBOs between d20-d25 of the culture process, organoids that have folding structures are then selected and embedded into Matrigel in a sandwich configuration. Folding structures includes folding sheets of EPCAM+KRT8+ECAD±FOXA1/2+AFE cells (FOXA2: 89.07%±3.36%, EPCAM+: 92.08%±1.88%, n=3; RUES2 ESCs). Forming the sandwich involves adding a first amount of Matrigel in a well or other suitable container and allowed to solidify to form the bottom portion of the sandwich. The selected organoids having folding structures are mixed with Matrigel and placed on top of the bottom portion and allowed to solidify to form the center cell layer. Another amount of Matrigel without cells is placed on top of the embedded cell layer and allowed to solidify to form the top portion of the sandwich. Ventralization media/Branching media is placed in the well and replenished periodically. Generation of branching buds from organoids occurs one week after embedding into Matrigel. Extensive branching organoids is observed 2-3 weeks post embedding.

Reagents and Methods

Reagents Reagents used are listed in Table 1 below.

Human Samples

The use of human fetal tissues procured by the Human Studies Core at Columbia Center for Translational Immunology was approved by the Columbia University Medical Center (CUMC) Human research review committee and the experiments were performed in accordance with the approved protocols.

Media hPSC maintenance media consisted of DMEM/F12 (1:1) supplemented with 20% knockout serum replacement, 0.1 mM β-mercaptoethanol, 1 ml Primocin, 5 ml Non-essential amino acids, 5 ml GlutaMax, and 20 ng/ml FGF-2. Serum-free differentiation (SFD) media consisted of IMDM/Ham's F12 (3:1) supplemented with N2, B27, 0.05% bovine serum albumin, 1% penicillin-streptomycin, 50 ug/ml ascorbic acid, 2 mM Glutamax, 0.4 μM monothioglycerol and different growth factor cocktails as indicated in Table 2.

hPSCs Maintenance

Rockefeller University Embryonic Stem Cell Line 2 (RUES2, NIH approval number NIHhESC-09-0013, Registration number 0013, passage 17-28), Sendai Virus and modified mRNA generated hiPSC lines from healthy human dermal fibroblasts[11,12] (passage 16-25) and IRF7-deficient C12 hiPSC lines[13] were maintained on mouse embryonic fibroblasts (MEFs) plated at 15,000-18,000 cells/cm$^2$. Cells were cultured in hPSC maintenance media and medium was changed daily. hPSCs were passaged with Accutase/EDTA washed and replated at a dilution of 1:48. Cultures were maintained in a humidified 5% $CO_2$ atmosphere at 37° C. Lines are karyotyped and verified for *Mycoplasma* contamination using PCR every 6 months.

Endoderm Induction

Induction of endoderm was carried as previous described[11]. Briefly, MEFs were depleted by passaging onto Matrigel for 24 h supplied with hPSC maintenance media and maintained in a humidified 5% $CO_2$ atmosphere at 37° C. After MEF depletion, primitive streak and embryoid body induction was performed in embryoid bodies/primitive streak formation media (Table 2) in low attachment plates for 12-16 h followed by switching to endoderm induction media (Table 2) for 36-40 h. Embryoid bodies were fed every day and maintained in a humidified 5% $CO_2$/5% $O_2$ atmosphere at 37° C. Endoderm yield was determined by the expression of CXCR4 and c-KIT. For iPS lines, endodermal cells were purified using human CD184 (CXCR4) MicroBead kit. Cells used in all experiments had >90% endoderm yield.

Anterior Foregut Endoderm Induction

Anterior foregut endoderm was induced as previous described[11]. On day 4, embryoid bodies were dissociated with 0.05% Trypsin/EDTA and plated on fibronectin-coated multiple well plates with a density at 80,000-105,000 cells/cm$^2$. Cells were incubated in Anteriorization media-1 for 24 h followed by switching to Anteriorization media-2 for another 24 h.

Formation of Lung Bud Organoids

At the end of anterior foregut endoderm induction, cells were treated with Ventralization media (Branching media) for 48 h and three-dimensional clump formation was observed. The clumps were then suspended by gently pipetting around the wells. The suspended clumps are called lung bud organoids (LBOs) hereafter. LBOs were maintained in non-tissue culture treated multiple-well plates submerged in Branching media and were fed every other day until d20-d25.

Branching Morphogenesis in Matrigel

The d20-d25 LBOs were embedded in 100% Matrigel in 24-well transwell inserts and incubated in incubator until the Matrigel solidified. Branching media were added to the well, after which the transwell was inserted, branching media added into the transwell insert as well. Media were changed every other day. A step-by-step protocol describing the generation of LBOs and LBO-derived branching colonies in Matrigel can be found in Example 2.

Immunofluorescence Staining

LBOs and branching Matrigel cultures were freshly embedded in Optimal Cutting Temperature (OCT). Samples were sectioned between 5-8 μm, and then air dried for 2 hours. The sections were fixed with 4% paraformaldehyde for 20 minutes at room temperature (RT) and washed with DPBS for 5 minutes. The sections were permeabilized with 0.3% Triton X-100/PBS for 30 minutes followed by blocking in 5% donkey serum for 1 hour. Primary antibodies (Table 3) were incubated at 4° C. overnight. The next day, sections were washed with DPBS 3×5 minutes followed by secondary antibody (Table 3) incubation for 2 hours at RT, washed 3×10 minutes with DPBS then mounted with DAPI contained fluorescent mounting medium. For 3D imaging, D25 LBOs were stained as described above, but were stained as intact organoids.

Isolation of EPCAM and EPCAM$^-$ Population from LBOs

LBOs were dissociated by 0.05% Trypsin/EDTA. The cells were stained with APC-conjugated EPCAM for 20 minutes at 4° C. EPCAM$^+$ and EPCAM$^-$ cells were isolated by Fluorescence activated cell sorting (FACS) using a BD Influx Cell Sorter (San Jose, Calif.).

Dot Blots

Three microliter of fluid aspirated from the tubular structures of 5 month grafts was deposited onto a nitrocellulose blotting membrane (GE Healthcare Life Sciences). The dot-blot membrane was air-dried for 5 minutes, and blocked in 5% milk/PBS for 1 hour and then probed with the indicated primary antibodies (Table 3) overnight at 4° C. HRP-conjugated secondary antibodies was applied to the membranes followed by signal detection with ECL Western Blotting Detection Reagents and exposure to X-ray film.

Imaging

Samples were imaged using motorized Leica DMI6000 B (Leica Microsystems, Buffalo Grove, Ill.) or DMi8 (Leica Microsystems, Buffalo Grove, Ill.) inverted microscopes or 2-photon confocal laser scanning microscope Leica TCS SP8 (Leica Microsystems, Buffalo Grove, Ill.). Macroscopic images (FIG. 3A and FIG. 5A) were taken using iPhone 6 (Model: MG5A2LL/A, Apple, Cupertino, Calif.).

Uptake of SPB-BODIPY in Live LBOs and Quantification d170 LBOs were stained with CellMask' Deep Red Plasma membrane Stain for 10 minutes and washed for 5 times followed by imaging prior loading SPB-BODIPY to obtained background fluorescence levels (0 min). The cultures then were loaded with 20 ng/ml purified human SPB-BODIPY protein (10 ng in total per culture) directly on top of the Matrigel. Images were taken every 2 minutes using a 2-photon confocal laser scanning microscope (Leica TCS SP8) and the fluorescent intensities were quantified using Leica Application Suite X. The background fluorescence values were subtracted from all measurements before statistical analysis.

Quantification of Immunofluorescence

Images for each nuclear marker were quantified using ImageJ. Briefly, images were converted to 8-bit images and the threshold was adjusted to correspond with the nuclear stain, which allows for measurement of total area. The total area was analyzed by the "Analyze Particles" function of ImageJ. Percentage of positive cells were calculated by dividing the total area of positive cells over the total area of DAPI. For extracellular matrix quantification, fluorescence intensity was quantified using Leica Application Suite X. The values were normalized to the RUES2 control for each individual experiment before statistical analysis.

Transmission Electron Microscopy

Transmission Electron Microscopy (TEM) was performed at the NYU Langone Medical Center Microscopy Core. LBOs were fixed with 2.5% glutaraldehyde in 0.1M sodium cacodylate buffer (pH7.2) for 2 hours and post-fixed with 1% osmium tetroxide for 1.5 hours at room temperature, then processed in a standard manner and embedded in EMbed 812 (Electron Microscopy Sciences, Hatfield, Pa.). Semi-thin sections were cut at 1 mm and stained with 1% Toluidine Blue to evaluate the quality of preservation and find the area of interest. Ultrathin sections (60 nm) were cut, mounted on copper grids and stained with uranyl acetate and lead citrate by standard methods. Stained grids were examined under Philips CM-12 electron microscope and photographed with a Gatan (4 k×2.7 k) digital camera (Gatan, Inc., Pleasanton, Calif.).

Detailed Protocol for Generation of Three-Dimensional Lung Bud Organoid and its Derived Branching Colonies.

This protocol describes the directed differentiation of human pluripotent stem cells (hPSCs) into three-dimensional lung bud organoids (LBOs) capable of branching morphogenesis. Based on the 2D protocol previously published by our group^^, we have designed a 3D system, in which hPSCs are sequentially differentiated into definitive endoderm (DE), to anterior foregut endoderm (AFE) and, ventral AFE in adherent 2D culture, followed by suspension culture to allow for LBO formation. When plated in Matrigel at d25, the LBOs underwent extensive outward branching and eventually formed dilated tips, reminiscent of saccules formed during the saccular stage of lung development. These cultures can be used to study human lung development and branching morphogenesis.

Organoids are structures comprised of multiple cell types that are spatially organized similarly to an organ and recapitulate at least some specific organ functions^15^. Several types of organoids have been described, derived both from adult tissue and from pluripotent stem cells. This technology will likely have a major impact on the study of developmental biology, organ physiology and function, and disease modeling^. However, a true human lung organoid model has not yet been realized. The respiratory system consists of a complex branched system of progressively smaller airways that terminate in alveoli where gas exchange takes place. Generation of human lung organoids has previously been reported^[18, 19]^. However, the organoids described did not show branching morphogenesis or proximodistal specification, while function was not documented. The lung bud organoid (LBO) model described in the current protocol displays branching morphogenesis, proximodistal specification and evidence of early alveologenesis both in vivo and in vitro. Their development reaches a stage equivalent to the second trimester of human development. LBO-derived branching structures in Matrigel contain type 2 alveolar epithelial cells (AT2) with abundant lamellar bodies and are capable of uptake and release of surfactant protein in vitro. Furthermore, secretion of mucins and surfactant proteins, as well as ciliary movement, were demonstrated after xenografting. The LBOs generated by this protocol therefore fulfill the definition of true organoids, and will be useful for studying human lung development and potentially for modeling human lung disease.

Reagents

| Name | Catalog number | Manufacturer |
|---|---|---|
| 1. 0.05% Trypsin/EDTA | 25300120 | Gibco |
| 2. 10 cm² tissue-culture dish | 353003 | BD Falcon |
| 3. 15 ml tube | 352097 | BD Falcon |
| 4. 24-well transwell insert | 8770 | BD Falcon |
| 5. 50 ml tube | 352098 | BD Falcon |
| 6. 7.5% Bovine serum albumin | 15260037 | Gibco |
| 7. Accutase/EDTA | AT104 | Innovative Cell Technologies |
| 8. Activin A | 338-AC | R&D System |
| 9. All-trans Retinoic acid | 0695 | R&D System |
| 10. Ascorbic acid | A4544 | Sigma |
| 11. B27 | 17504044 | Gibco |
| 12. β-mercaptoethanol | M6250 | Sigma |
| 13. BMP4 | 214-BP | R&D System |
| 14. CHIR 99021 | 4423 | R&D System |
| 15. c-KIT-PE | 313204 | Biolegend |
| 16. CXCR4-APC | 306510 | Biolegend |
| 17. FGF10 | 345-FG | R&D System |
| 18. FGF2 | 233-FB | R&D System |
| 19. FGF7 | 251-KG | R&D System |
| 20. Fibronectin | 1918-FN | R&D System |
| 21. Glutamax | 35050061 | Gibco |
| 22. Growth factor reduced matrigel | 354230 | Corning |
| 23. Ham's F12 | 10-080-CV | Cellgro |
| 24. Iscove's Modified Dulbecco's Medium (IMDM) | 10-016-CV | Cellgro |
| 25. IWP2 | 3533 | R&D System |
| 26. knockout serum replacement | 10828028 | Gibco |
| 27. low-adherin plate | 3471 | costar |
| 28. MEM Non-Essential Amino Acids Solution | 11140050 | Gibco |
| 29. Monothioglycerol | M6145 | Sigma |
| 30. Mouse embryonic fibroblasts | GSC-6201G | GlobalStem |
| 31. N2 | 17502048 | Gibco |
| 32. Noggin | 6057-NG | R&D System |
| 33. Non-tissue culture-treated plate | 351146 | BD Falcon |
| 34. Penicillin-streptomycin | 30-002-CI | Cellgro |
| 35. Primocin | ant-pm-2 | InvivoGen |
| 36. SB 431542 | 1614 | R&D System |
| 37. Y-27632 | 1254 | R&D System |

| Media | Base media | Components | |
|---|---|---|---|
| Stop media | | IMDM | 500 ml |
| | | FBS | 25 ml |
| | | GultaMax | 5 ml |
| | | Penicillin-streptomycin | 5 ml |
| hPSC maintenance media | | DMEM/F12 | 400 ml |
| | | Knockout serum | 100 ml |
| | | β-mercaptoethanol | 0.1 mM |
| | | Primocin | 1 ml |
| | | FGF2 | 20 ng/ml |
| | | GlutaMax | 5 ml |
| Serum-free differentiation (SFD) media | | IMDM | 750 ml |
| | | Ham's F-12 | 250 ml |
| | | N2 | 5 ml |
| | | B27 | 10 ml |
| | | 7.5% BSA | 7.5 ml |
| | | Penicillin-streptomycin | 1% |
| | | GultaMax | 10 ml |
| | | Ascorbic acid | 50 µg/ml |
| | | Monothioglycerol | 0.4 µM |
| Embryoid bodies/primitive streak formation media | SFD | Y-27632 | 10 µM |
| | | BMP4 | 3 ng/ml |
| Endoderm induction media | SFD | Y-27632 | 10 µM |
| | | BMP4 | 0.5 ng/ml |
| | | FGF2 | 2.5 ng/ml |
| | | Activin A | 100 ng/ml |
| Anteriorization media-1 | SFD | Noggin | 100 ng/ml |
| | | SB431542 | 10 µM |
| Anteriorization media-2 | SFD | SB431542 | 10 µM |
| | | IWP2 | 1 µM |
| Ventralization media/Branching media | SFD | CHIR99021 | 3 µM |
| | | FGF10 | 10 ng/ml |
| | | FGF7 | 10 ng/ml |
| | | BMP4 | 10 ng/ml |
| | | all-trans Retinoic acid | 50 nM |

Equipment:
Normoxic incubator (95% air/5% $CO_2$), low oxygen incubator (5% $O_2$/5% $CO_2$), centrifuge, hemocytometer, picking hood.

Procedure:
MEF Depletion on Matrigel (d-1)
1. Thaw Matrigel on ice and leave the ice bucket with the Matrigel at 4° C. overnight.
2. Dilute Matrigel in cold IMDM (1:30).
3. Add 6 ml of diluted Matrigel solution to each 10 cm² tissue culture-treated dishes and let them sit for at least 3 hours at room temperature or overnight at 4° C.
4. To make one 6-well plate embryoid bodies (EBs), dissociate two confluent wells (from a 6-well plate) of human pluripotent stem cells (hPSCs) using 1 ml/well Accutase and incubate in a normoxic incubator for 2-3 minutes.
5. Aspirate the Accutase.
6. Neutralize the enzyme by stop media.
7. Pellet the dissociated cells by centrifugation at 1,400 r.p.m. for 4 minutes.
8. Aspirate enzyme and stop media as much as possible.
9. Re-suspend the cells with 10-12 ml hPSC maintenance media.
10. Plate the cells in a Matrigel-coated dish (see step 3) after aspiration of the supernatant from the dish.

11. Incubate the cells in a normoxic incubator overnight.

Endoderm Induction (d0-d4)

1. On d0, remove the hPSC maintenance media from the Matrigel-coated dish and add 3 ml trypsin. Incubate the dish for 1-1.5 minutes in a normoxic incubator.
2. Aspirate trypsin solution and stop the remaining enzyme by adding 10 ml stop media.
3. Collect the detached cells and pellet by centrifugation at 1,400 r.p.m. for 4 minutes.
4. Aspirate the enzyme and stop media.
5. Re-suspend the cells with 12 ml Embryoid bodies/primitive streak formation media and distribute to a 6-well low-attachment plate (2 ml/well).
6. Place the low-attachment plate in a low oxygen incubator to allow embryoid body (EB) formation.
7. After 12-16 hours, collect all EBs in a 15-ml tube and centrifuge at 800 r.p.m. for 1 minute.
8. Aspirate the Embryoid bodies/primitive streak formation media.
9. Gently re-suspend the EBs with 12 ml Endoderm induction media and distribute them equally back to the low-attachment plate (2 ml/well).
10. Return the plate back to a low oxygen incubator.
11. On d2, add 1 ml fresh Endoderm induction media to each well.
12. On d3, add 2 ml fresh Endoderm induction media to each well.
13. On d4.1-d4.3, check endoderm yield by flow cytometric analysis of CXCR4 and c-kit expression. If the endoderm yield is >90%, continue the differentiation.

Anteriorization (d5-d6)

1. Prepare fibronectin-coated 6-well plates by diluting fibronectin to 0.2% (vol/vol, 1:500, 4 µg/ml) in DPBS. Add 2 ml fibronectin/DPBS solution to each well and incubate the plates in a normoxic incubator for at least 30 minutes or 4° C. overnight.
2. Dissociate the EBs into single cells with trypsin (3 ml of trypsin per 6-well plate of EBs for a maximum 4-minute digestion).
3. Neutralize the enzyme by stop media.
4. Count the cells using a hemocytometer.
5. Pellet the dissociated cells by centrifugation at 1,400 r.p.m. for 4 minutes.
6. Aspirate the stop media.
7. Re-suspend the cells with Anteriorization media-1 at $7.5 \times 10^{5}$ cells/2 ml.
8. Add 2 ml of cell mixture to each well (6-well plate, fibronectin-coated, see step 1).
9. Incubate the plates in a normoxic incubator.
10. After 24 hours (±1 hour), replace the Anteriorization media-1 with Anteriorization media-2 (2 ml/well).
11. Return the plates back to a normoxic incubator.

Ventralization and Lung Bud Organoid (LBO) Formation (d6-d25)

1. After 24 hours (±1 hour), replace the Anteriorization media-2 with Ventralization media/Branching media (2 ml/well).
2. Return the plates back to a normoxic incubator.
3. Forty-eight hours later, aspirate all the Ventralization media/Branching media and add 2 ml fresh Ventralization media/Branching media to each well.
4. Suspend the organoids by gently pipetting up and down throughout the well with P1000 tips.
5. Transfer the suspended organoids to non-tissue culture-treated plates.
6. Return the plates back to a normoxic incubator.
7. Feed the organoids every other day by tilting the plate and allowing the organoids to sink to the bottom edge. Remove the old media while avoiding touching the organoids. Add 2 ml fresh Ventralization media/Branching media to each well.

Branching Organoid (d20-End of Experiment)

1. Between d20-d25, select the organoids with folding structures under picking hood.
2. Put the desired number of organoids per insert into each well (96-well U-bottom plate containing 100 µl of fresh Ventralization media/Branching media per well). Typically, one to four organoids are plated per insert (24-well insert).
3. Place 24-well inserts into non-tissue culture treated plates.
4. Lay 50 µl of 100% cold Matrigel into the bottom of each insert.
5. Wait 5 minutes or until the Matrigel has solidified.
6. Remove the Ventralization media/Branching media one well at a time.
7. Mix the organoids with 30 µl of 100% cold Matrigel gently to avoid creating bubbles.
8. Immediately put the organoid-Matrigel mixture in the center of an insert.
9. Wait for 5 minutes for the Matrigel to solidify to secure the organoids in the center of the insert.
10. Add another 50 µl of 100% cold Matrigel to the insert to create a Matrigel sandwich.
11. Put the plates in a normoxic incubator for 10 minutes to make sure all Matrigel has solidified.
12. Add 500 µl of Ventralization media/Branching media to the insert and another 500 µl of Ventralization media/Branching media into the wells.
13. Incubate the cultures in a normoxic incubator and replace the media every 2-3 days.

Timing:

Hands-on time for each step:

MEF depletion on Matrigel (d-1): 20 minutes

Endoderm induction (d0-d4): 2 hours

Anteriorization (d5-d6): 1 hour

Ventralization and Lung Bud Organoid (LBO) formation: 30 minutes plus suspension of organoids: 5 minutes/plate Branching organoid: Roughly 2 hours to finish embedding 24 inserts and supplying them with media.

ADDITIONAL REFERENCES FOR METHODS SECTION

1 Green, M. D. et al. Generation of anterior foregut endoderm from human embryonic and induced pluripotent stem cells. *Nat Biotechnol* 29, 267-272, doi:10.1038/nbt.1788 (2011).
2 Huang, S. X. et al. The in vitro generation of lung and airway progenitor cells from human pluripotent stem cells. *Nat Protoc* 10, 413-425, doi:10.1038/nprot.2015.023 (2015).
3 Huang, S. X. et al. Efficient generation of lung and airway epithelial cells from human pluripotent stem cells. *Nat Biotechnol* 32, 84-91, doi:10.1038/nbt.2754 (2014).
4 Lancaster, M. A. & Knoblich, J. A. Organogenesis in a dish: modeling development and disease using organoid technologies. *Science* 345, 1247125, doi:10.1126/science.1247125 (2014).
5 Fatehullah, A., Tan, S. H. & Barker, N. Organoids as an in vitro model of human development and disease. *Nat Cell Biol* 18, 246-254, doi:10.1038/ncb3312 (2016).

6 Clevers, H. Modeling Development and Disease with Organoids. *Cell* 165, 1586-1597, doi:10.1016/j.cell.2016.05.082 (2016).
7 Herriges, M. & Morrisey, E. E. Lung development: orchestrating the generation and regeneration of a complex organ. *Development* 141, 502-513, doi:10.1242/dev.098186 (2014).
8 Morrisey, E. E. & Hogan, B. L. Preparing for the first breath: genetic and cellular mechanisms in lung development. *Dev Cell* 18, 8-23, doi:10.1016/j.devcel.2009.12.010 (2010).
9 Dye, B. R. et al. A bioengineered niche promotes in vivo engraftment and maturation of pluripotent stem cell derived human lung organoids. *Elife* 5, doi:10.7554/eLife.19732 (2016).
10 Dye, B. R. et al. In vitro generation of human pluripotent stem cell derived lung organoids. *Elife* 4, doi:10.7554/eLife.05098 (2015).

TABLE 1

Reagents

| Name | Catalog Number | Vendor | Location |
|---|---|---|---|
| Agilent RNA 6000 Nano Kit | 5067-1511 | Agilent Technologies | Santa Clara, CA |
| T7 MAXIscript kit | AM1314 | Ambion | Waltham, MA |
| 20X SSC Buffer | AM9763 | Ambion | Waltham, MA |
| formamide | AB00600-00100 | American Bioanalytical | Natick, MA |
| APC BrdU Flow Kit | 552598 | BD Bioscience | San Jose, CA |
| 24-well transwell insert | 8770 | BD Falcon | Tewksbury, MA |
| CXCR4 | 306510 | Biolegend | San Diego, CA |
| c-KIT | 313204 | Biolegend | San Diego, CA |
| EPCAM-APC | 324208 | Biolegend | San Diego, CA |
| dextran sulfate | 40400040-2 | Bioworld | Dublin, OH |
| Dulbecco's Modified Eagle Medium | 10-013-CV | Cellgro | Manassas, VA |
| Ham's F12 | 10-080-CV | Cellgro | Manassas, VA |
| Iscove's Modified Dulbecco's Medium | 10-016-CV | Cellgro | Manassas, VA |
| DMEM/F12 | 10-092-CV | Cellgro | Manassas, VA |
| Penicillin-streptomycin | 30-002-CI | Cellgro | Manassas, VA |
| DPBS | 21-031-CM | Cellgro | Manassas, VA |
| Growth factor reduced matrigel | 354230 | Corning | Corning, NY |
| low-adherin plate | 3471 | costar | Tewksbury, MA |
| 16% Paraformaldehyde | 15710 | Electron Microscopy Sciences | Hatfield, PA |
| donkey serum | S30-100ML | EMD Millipore | Billerica, MA |
| Triton X-100 | BP151 | Fisher Scientific | Hampton, NH |
| nitrocellulose blotting membrane | 10600062 | GE Healthcare Life Sciences | Pittsburgh, PA |
| knockout serum replacement | 10828028 | Gibco | Grand Island, NY |
| N2 | 17502048 | Gibco | Grand Island, NY |
| B27 | 17504044 | Gibco | Grand Island, NY |
| 7.5% Bovine serum albumin | 15260037 | Gibco | Grand Island, NY |
| Glutamax | 35050061 | Gibco | Grand Island, NY |
| 0.05% Trypsin/EDTA | 25300120 | Gibco | Grand Island, NY |
| 0.25% Trypsin/EDTA | 25200056 | Gibco | Grand Island, NY |
| Mouse embryonic fibroblasts | GSC-6201G | GlobalStem | Rockville, MD |
| Fluorescent mounting medium with DAPI | E19-18 | IHC World | Ellicott City, MD |
| Accutase/EDTA | AT104 | Innovative Cell Technologies | San Diego, CA |
| UltraPure ™ Salmon Sperm DNA Solution | 15632011 | Invitrogen | Waltham, MA |
| Primocin | ant-pm-2 | InvivoGen | San Diego, CA |
| CXCR4 MicroBead kit | 130-100-070 | Miltenyi Biotec | San Diego, CA |
| Sheep Serum | 092936149 | MP Biomedicals | Santa Ana, CA |
| RNeasy micro kit | 74004 | Qiagen | Valencia, CA |
| fibronectin | 1918-FN | R&D System | St. Louis, MO |
| BMP4 | 314-BP | R&D System | St. Louis, MO |
| FGF2 | 233-FB | R&D System | St. Louis, MO |
| Activin A | 338-AC | R&D System | St. Louis, MO |
| FGF10 | 345-FG | R&D System | St. Louis, MO |
| FGF7 | 251-KG | R&D System | St. Louis, MO |
| all-trans Retinoic acid | 0695 | R&D System | St. Louis, MO |
| Noggin | 6057-NG | R&D System | St. Louis, MO |
| SB 431542 | 1614 | R&D System | St. Louis, MO |
| IWP2 | 3533 | R&D System | St. Louis, MO |
| Digoxigenin-11-UTP | 11209256910 | Sigma | St. Louis, MO |
| triethanolamine | 90279 | Sigma | St. Louis, MO |

TABLE 1-continued

Reagents

| Name | Catalog Number | Vendor | Location |
|---|---|---|---|
| Denhardt's Solution 50x | D2532 | Sigma | St. Louis, MO |
| Anti-digoxigenin AP-conjugate | 50-100-3276 | Sigma | St. Louis, MO |
| BM-purple | 50-100-3285 | Sigma | St. Louis, MO |
| b-mercaptoethanol | M6250 | Sigma-Aldrich | St. Louis, MO |
| Ascorbic acid | A4544 | Sigma-Aldrich | St. Louis, MO |
| Monothioglycerol | M6145 | Sigma-Aldrich | St. Louis, MO |
| NSG mice | 005557 | The Jacoson Laboratory | Bar Harbor, ME |
| OCT | 4583 | Tissue-Tek | Torrance, CA |
| Y-27632 | 1254 | Tocris | Bristol, BS, UK |
| CHIR 99021 | 4423 | Tocris | Bristol, BS, UK |
| Dexamethasone | 1126 | Tocris | Bristol, BS, UK |
| 8-bromo-cAMP | 1140 | Tocris | Bristol, BS, UK |
| Direct-zol RNA MicroPrep kit | R2062 | Zymo Research | Irvine, CA |
| Hydroxyproline assay kit | MAK008-1KT | Sigma-Aldrich | St. Louis, MO |
| fetal bovine serum | 10082-147 | Gibco | Grand Island, NY |
| pDsRed | 632412 | Clontech | Palo Alto, CA |
| OptiMEM | 11058-021 | Gibco | Grand Island, NY |
| methyl cellulose | HSC001 | R&D System | St. Louis, MO |
| crystal violet | HT90132 | Sigma-Aldrich | St. Louis, MO |
| L-glutamine | 25030-081 | Gibco | Grand Island, NY |
| CellMaskTM Deep Red Plasma membrane Stain | C10046 | ThermoFisher | Waltham, MA |
| MEM Non-Essential Amino Acids Solution (100X) | 11140050 | Gibco | Grand Island, NY |

TABLE 2

Culture media

| Time | Basal media: SFD | |
|---|---|---|
| d-1 | MEF depletion | |
| | Endoderm induction | |
| d0 | Embryoid bodies/primitive streak formation media | Working concentration |
| | Y-27632 | 10 µM |
| | BMP4 | 3 ng/ml |
| d1-d4 | Endoderm induction media | Working concentration |
| | Y-27632 | 10 µM |
| | BMP4 | 0.5 ng/ml |
| | FGF2 | 2.5 ng/ml |
| | Activin A | 100 ng/ml |
| d4 | Anteriorization media-1 | |
| | Noggin | 100 ng/ml |
| | SB431542 | 10 µM |
| d5 | Anteriorization media-2 | |
| | SB431542 | 10 µM |
| | IWP2 | 1 µM |
| d6- | Ventralization media/Branching media | |
| | CHIR99021 | 3 µM |
| | FGF10 | 10 ng/ml |
| | FGF7 | 10 ng/ml |
| | BMP4 | 10 ng/ml |
| | all-trans Retinoic acid | 50 nM |

TABLE 3

Antibodies and dilutions

| Name | Host species | Clone number | Manufacturer | Catalog number | Dilution factor |
|---|---|---|---|---|---|
| Antibodies used for immunofluorscent staining | | | | | |
| EPCAM | mouse | 9C4 | Biolegend | 324202 | 1:500 |
| EPCAM | rabbit | D1B3 | Cell Signaling | 2626 | 1:1500 |
| EPCAM | goat | | R&D systems | AF960 | 10 µg/ml |
| Keratin 8 | mouse | A-9 | Santa Cruz | sc-374275 | 1:500 |
| NKK2.1 (TTF1) | mouse | 8G7G3/1 | Life Technologies | 180221 | 1:100 |
| NKK2.1 (TTF1) | rabbit | | Seven Hills | WRAB-1231 | 1:1000 |
| FOXA1 (HNF-3α) | mouse | Q-6 | Santa Cruz | sc-101058 | 1:50 |

TABLE 3-continued

Antibodies and dilutions

| Name | Host species | Clone number | Manufacturer | Catalog number | Dilution factor |
|---|---|---|---|---|---|
| FOXA2 (HNF-3β) | goat | M-20 | Santa Cruz | sc-6554 | 1:50 |
| FOXA2 (HNF-3β) | rabbit | | Seven Hills | WRAB-1200 | 1:2000 |
| P63 | mouse | 4A4 | Santa Cruz | sc-8431 | 1:100 |
| P63α | rabbit | H-129 | Santa Cruz | sc-8344 | 1:100 |
| PDGFRa | rabbit | D13C6 | Cell Signaling | 5241 | 1:800 |
| E-cadherin | Rat | DECMA-1 | Biolegend | 147303 | 1:200 |
| SOX2 | goat | Y-17 | Santa Cruz | sc-17320 | 1:100 |
| SOX2 | rabbit | | Seven Hills | WRAB-1236 | 1:2000 |
| SOX9 | rabbit | | Millipore | AB5535 | 1:1000 |
| THY1 (CD90) | mouse | 5E10 | Biolegend | 328102 | 1:50 |
| MUC1 | armenian hamster | MH1 (CT2) | NeoMarkers | HM-1630-P | 1:100 |
| MUC2 | rabbit | H-300 | Santa Cruz | sc-15334 | 1:100 |
| MUC5AC | mouse | 45M1 | Abcam | ab79082 | 1:100 |
| MUC5B | rabbit | H-300 | Santa Cruz | sc-20119 | 1:100 |
| FOXJ1 | mouse | 2A5 | eBioscience | 14-9965-82 | 1:100 |
| SFTPB | rabbit | | Seven Hills | WRAB-48604 | 1:1000 |
| SFTPC | rabbit | | Seven Hills | WRAB-76694 | 1:1000 |
| ABCA3 | rabbit | | Seven Hills | WRAB-70565 | 1:1000 |
| HOPX | rabbit | FL-73 | Santa Cruz | sc-30216 | 1:250 |
| Caveolin 1 | rabbit | D46G3 | Cell Signaling | 3267 | 1:400 |
| PDPN | rabbit | FL-162 | Santa Cruz | sc-134482 | 1:100 |
| Vimentin | rabbit | D21H3 | Cell Signaling | 5741 | 1:100 |
| Collagen IV | mouse | COL-94 | Abcam | ab6311 | 1:500 |
| Human nuclei | mouse | 235-1 | Millipore | MAB1281 | 1:200 |
| hCD31 | mouse | WM59 | Biolegend | 303102 | 1:200 |
| mCD31 | rat | MEC 13.3 | BD Biosciences | 550274 | 1:100 |
| SMA | rabbit | E184 | Abcam | ab32575 | 1:500 |
| SCGB3A2 | goat | K-12 | Santa Cruz | sc-48320 | 1:50 |
| Ki67 | mouse | B56 | BD Biosciences | 550609 | 1:200 |
| CC10 | goat | C-20 | Santa Cruz | sc-9770 | 1:100 |
| CC10 | goat | S-20 | Santa Cruz | sc-9773 | 1:100 |
| AQP5 | goat | G-19 | Santa Cruz | sc-9890 | 1:100 |
| NGFR | mouse | ME20.4 | Millipore | 05-446 | 1:100 |
| CLIC5 | rabbit | | ThermoFisher | PA5-14533 | 1:100 |
| AKAP5 | rabbit | | ThermoFisher | PA5-38594 | 1:100 |
| SCNN1A | rabbit | | ThermoFisher | PA5-29136 | 1:100 |
| H11-56 | mouse | | Terrace Biotech | TB-29AHT1-56 | 1:150 |
| HT2-280 | mouse | | Terrace Biotech | TB-27AHT2-280 | 1:150 |
| CGRP | mouse | CD8 | Sigma | C9487 | 1:100 |
| PGP9.5 | mouse | 31A3 | Abcam | ab20559 | 1:200 |
| Collagen I | rabbit | | Abcam | ab34710 | 1:1000 |
| Collagen III | rabbit | | Abcam | ab7778 | 1″200 |
| Vimentin-Alexa Fluor 488 | rabbit | D21H3 | Cell Signaling | 9854 | 1:800 |
| PDGFRb | rabbit | 28E1 | Cell Signaling | 3169 | 1:100 |
| Fibronectin | mouse | IST-9 | Abcam | ab6328 | 1:200 |
| Ki67-488 | mouse | | Biolegend | 350508 | 1:50 |
| RSV antigen | goat | | Meridian Life Science | B65860G | 1:200 |
| CellMask™ Deep Red Plasma membrane Stain | | | ThermoFisher | C10046 | 1:1000 |

Antibodies used for Western Blot

| Name | Host species | Clone number | Manufacturer | Catalog number | Dilution factor |
|---|---|---|---|---|---|
| CC10 | goat | C-20 | Santa Cruz | sc-9770 | 1:100 |
| MUC5AC | mouse | 45M1 | Abcam | ab79082 | 1:100 |
| MUC5B | rabbit | H-300 | Santa Cruz | sc-20119 | 1:100 |
| MUC2 | rabbit | H-300 | Santa Cruz | sc-15334 | 1:100 |
| SFTPB | rabbit | | Seven Hills | WRAB-48604 | 1:1000 |
| SFTPC | rabbit | | Seven Hills | WRAB-76694 | 1:1000 |
| MUC1 | armenian hamster | MH1 (CT2) | NeoMarkers | HM-1630-P | 1:100 |

ADDITIONAL REFERENCES

1. Noble, P. W., Barkauskas, C. E. & Jiang, D. Pulmonary fibrosis: patterns and perpetrators. *J Clin Invest* 122, 2756-2762 (2012).
2. Ryu, J. H. et al. Idiopathic pulmonary fibrosis: evolving concepts. *Mayo Clinic proceedings* 89, 1130-1142 (2014).
3. McCurry, K. R. et al. Lung transplantation in the United States, 1998-2007.*Am J Transplant* 9, 942-958 (2009).
4. Orens, J. B. & Garrity, E. R., Jr. General overview of lung transplantation and review of organ allocation. *Proc Am Thorac Soc* 6, 13-19 (2009).
5. Murry, C. E. & Keller, G. Differentiation of embryonic stem cells to clinically relevant populations: lessons from embryonic development. *Cell* 132, 661-680 (2008).
6. Miller, A. J. et al. In Vitro Induction and In Vivo Engraftment of Lung Bud Tip Progenitor Cells Derived from Human Pluripotent Stem Cells. *Stem cell reports* 10, 101-119 (2018).
7. Yang, Y. et al. Spatial-Temporal Lineage Restrictions of Embryonic p63(+) Progenitors Establish Distinct Stem Cell Pools in Adult Airways. *Dev Cell* 44, 752-761 e754 (2018).
8. Dorrello, N. V. et al. Functional vascularized lung grafts for lung bioengineering. *Sci Adv* 3, e1700521 (2017).
9. Herriges, M. & Morrisey, E. E. Lung development: orchestrating the generation and regeneration of a complex organ. *Development* 141, 502-513 (2014).
10. Morrisey, E. E. & Hogan, B. L. Preparing for the first breath: genetic and cellular mechanisms in lung development. *Dev Cell* 18, 8-23 (2010).
11. Huang, S. X. et al. The in vitro generation of lung and airway progenitor cells from human pluripotent stem cells. *Nature protocols* 10, 413-425 (2015).
12. Huang, S. X. et al. Efficient generation of lung and airway epithelial cells from human pluripotent stem cells. *Nature biotechnology* 32, 84-91 (2014).
13. Ciancanelli, M. J. et al. Life-threatening influenza and impaired interferon amplification in human IRF7 deficiency. *Science* (2015).
14. Green, M. D. et al. Generation of anterior foregut endoderm from human embryonic and induced pluripotent stem cells. *Nature biotechnology* 29, 267-272 (2011).
15. Lancaster, M. A. & Knoblich, J. A. Organogenesis in a dish: modeling development and disease using organoid technologies. *Science* 345, 1247125 (2014).
16. Fatehullah, A., Tan, S. H. & Barker, N. Organoids as an in vitro model of human development and disease. *Nat Cell Biol* 18, 246-254 (2016).
17. Clevers, H. Modeling Development and Disease with Organoids. *Cell* 165, 1586-1597 (2016).
18. Dye, B. R. et al. A bioengineered niche promotes in vivo engraftment and maturation of pluripotent stem cell derived human lung organoids. *eLife* 5 (2016).
19. Dye, B. R. et al. In vitro generation of human pluripotent stem cell derived lung organoids. *eLife* 4 (2015).

All references cited herein are incorporated by reference to the same extent as if each individual publication, database entry (e.g. Genbank sequences or GeneID entries), patent application, or patent, was specifically and individually indicated to be incorporated by reference. This statement of incorporation by reference is intended by Applicants, pursuant to 37 C.F.R. § 1.57(b)(1), to relate to each and every individual publication, database entry (e.g. Genbank sequences or GeneID entries), patent application, or patent, each of which is clearly identified in compliance with 37 C.F.R. § 1.57(b)(2), even if such citation is not immediately adjacent to a dedicated statement of incorporation by reference. The inclusion of dedicated statements of incorporation by reference, if any, within the specification does not in any way weaken this general statement of incorporation by reference. Citation of the references herein is not intended as an admission that the reference is pertinent prior art, nor does it constitute any admission as to the contents or date of these publications or documents. The entire disclosure of each of the patent documents, including certificates of correction, patent application documents, scientific articles, governmental reports, websites, and other references referred to herein is incorporated by reference herein in its entirety for all purposes. In case of a conflict in terminology, the present specification controls.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

The foregoing written specification is considered to be sufficient to enable one skilled in the art to practice the invention. Various modifications of the invention in addition to those shown and described herein will become apparent to those skilled in the art from the foregoing description and fall within the scope of the appended claims.

The invention can be embodied in other specific forms without departing from the spirit or essential characteristics thereof. The foregoing embodiments are to be considered in all respects illustrative rather than limiting on the invention described herein. In the various embodiments of the methods and systems of the present invention, where the term comprises is used with respect to the recited steps or components, it is also contemplated that the methods and systems consist essentially of, or consist of, the recited steps or components. Further, it should be understood that the order of steps or order for performing certain actions is immaterial so long as the invention remains operable. Moreover, two or more steps or actions can be conducted simultaneously.

In the specification, the singular forms also include the plural forms, unless the context clearly dictates otherwise. Unless defined otherwise, all technical and scientific terms used herein have the same meaning as commonly understood by one of ordinary skill in the art to which this invention belongs. In the case of conflict, the present specification will control.

All percentages and ratios used herein, unless otherwise indicated, are by weight.

What is claimed is:

1. A method for generating lung progenitor cells, the method comprising:
   (a) producing anterior foregut endoderm cells from mammalian pluripotent stem cells (PSCs),
   (b) culturing the anterior foregut endoderm cells in a suspension culture comprising bone morphogenic protein 4 (BMP4), FGF10, FGF7, retinoic acid and a glycogen synthase kinase (GSK) inhibitor, to generate at least one lung bud organoid (LBO), wherein the LBO comprises (i) lung epithelial cells expressing FOXA2, FOXA1, NKX2.1 and EPCAM, and (ii) mesenchymal progenitors expressing PDGFRa, CD90, TBX4 and HOXA5;
   (c) embedding the LBO within a 3D matrix,
   (d) culturing the embedded LBO in presence of a GSK inhibitor, BMP4, FGF10, FGF7 and retinoic acid to induce branching to form branched LBO (BLBO), and
   (e) dissociating the BLBO and culturing the dissociated BLBO on feeder cells in a first culture medium, wherein the first culture medium comprises an inhibitor of Rho kinase (ROCK), a GSK inhibitor, FGF7, FGF10, BMP4, and retinoic acid.

2. The method of claim 1, wherein the inhibitor of ROCK is Y27632.

3. The method of claim 1, wherein the inhibitor of ROCK is at a concentration ranging from about 5 µM to about 15 µM.

4. The method of claim 1, wherein the inhibitor of ROCK is at a concentration of about 5 µM to about 10 µM.

5. The method of claim 1, wherein the GSK inhibitor is CHIR99021.

6. The method of claim 1, wherein the GSK inhibitor is at a concentration ranging from about 1 µM to about 10 µM.

7. The method of claim 1, wherein FGF7, FGF10, or BMP4 is at a concentration of about 10 ng/ml.

8. The method of claim 1, wherein retinoic acid is at a concentration of about 50 nM.

9. The method of claim 1, further comprising (f) culturing the dissociated BLBO on feeder cells in a second culture medium, wherein the second culture medium comprises insulin, EGF, hydrocortisone, cholera toxin, and an inhibitor of ROCK.

10. The method of claim 1, wherein the 3D matrix is a solubilized basement membrane preparation from the Engelbreth-Holm-Swarm (EHS) mouse sarcoma.

11. The method of claim 1, wherein the feeder cells are fibroblasts.

12. The method of claim 11, wherein the fibroblasts are irradiated 3T3-J2 cells.

13. The method of claim 1, wherein the BLBO is dissociated to single cells.

14. The method of claim 1, wherein the mammalian pluripotent stem cells (PSCs) are human pluripotent stem cells (hPSCs).

15. The method of claim 1, wherein the mammalian pluripotent stem cells (PSCs) are embryonic stem cells (ESCs) and/or induced pluripotent stem cells (iPSCs).

16. A method for generating lung progenitor cells, the method comprising:
(a) producing anterior foregut endoderm cells from mammalian pluripotent stem cells (PSCs);
(b) culturing the anterior foregut endoderm cells in a suspension culture comprising bone morphogenic protein 4 (BMP4), FGF10, FGF7, retinoic acid and a glycogen synthase kinase (GSK) inhibitor, to generate at least one lung bud organoid (LBO), wherein the LBO comprises (i) lung epithelial cells expressing FOXA2, FOXA1, NKX2.1 and EPCAM, and (ii) mesenchymal progenitors expressing PDGFRa, CD90, TBX4 and HOXA5; and
(c) dissociating the LBO and culturing the dissociated LBO on feeder cells in a first culture medium, wherein the first culture medium comprises an inhibitor of Rho kinase (ROCK), a GSK inhibitor, FGF7, FGF10, BMP4, and retinoic acid.

17. A method for generating lung progenitor cells, the method comprising:
(a) producing anterior foregut endoderm cells from mammalian pluripotent stem cells (PSCs),
(b) culturing the anterior foregut endoderm cells in a suspension culture comprising bone morphogenic protein 4 (BMP4), FGF10, FGF7, retinoic acid and a glycogen synthase kinase (GSK) inhibitor, to generate at least one lung bud organoid (LBO), wherein the LBO comprises (i) lung epithelial cells expressing FOXA2, FOXA1, NKX2.1 and EPCAM, and (ii) mesenchymal progenitors expressing PDGFRa, CD90, TBX4 and HOXA5;
(c) embedding the LBO within a 3D matrix,
(d) culturing the embedded LBO in presence of a GSK inhibitor, BMP4, FGF10, FGF7 and retinoic acid to form branched LBO (BLBO), and
(e) dissociating the BLBO and culturing the dissociated BLBO on feeder cells in a second culture medium, wherein the second culture medium comprises insulin, EGF, hydrocortisone, cholera toxin, and an inhibitor of ROCK.

18. A method for generating lung progenitor cells, the method comprising:
(a) producing anterior foregut endoderm cells from mammalian pluripotent stem cells (PSCs);
(b) culturing the anterior foregut endoderm cells in a suspension culture comprising bone morphogenic protein 4 (BMP4), FGF10, FGF7, retinoic acid and a glycogen synthase kinase (GSK) inhibitor, to generate at least one lung bud organoid (LBO), wherein the LBO comprises (i) lung epithelial cells expressing FOXA2, FOXA1, NKX2.1 and EPCAM, and (ii) mesenchymal progenitors expressing PDGFRa, CD90, TBX4, and HOXA5; and
(c) dissociating the LBO and culturing the dissociated LBO on feeder cells in a second culture medium, wherein the second culture medium comprises insulin, EGF, hydrocortisone, cholera toxin, and an inhibitor of ROCK.

* * * * *